United States Patent
Naganawa et al.

(10) Patent No.: US 8,138,335 B2
(45) Date of Patent: *Mar. 20, 2012

(54) CARBOXYLIC ACID COMPOUNDS AND MEDICINAL COMPOSITIONS CONTAINING THE SAME AS THE ACTIVE INGREDIENT

(75) Inventors: Atsushi Naganawa, Mishima-gun (JP); Maki Iwahashi, Mishima-gun (JP); Atsushi Kinoshita, Mishima-gun (JP); Atsushi Shimabukuro, Mishima-gun (JP); Seiji Ogawa, Mishima-gun (JP); Koji Yano, Mishima-gun (JP); Kaoru Kobayashi, Mishima-gun (JP); Yutaka Okada, Mishima-gun (JP); Yoko Kishida, Goleta, CA (US); Shouji Kawauchi, Neyagawa (JP); Kohki Tsukamoto, Mishima-gun (JP); Yoko Matsunaga, Mishima-gun (JP); Fumio Nambu, Mishima-gun (JP)

(73) Assignee: Ono Pharmaceutical Co., Ltd, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/551,860

(22) Filed: Sep. 1, 2009

(65) Prior Publication Data
US 2010/0029631 A1 Feb. 4, 2010

Related U.S. Application Data

(62) Division of application No. 10/572,578, filed on Mar. 17, 2006, now Pat. No. 7,601,712.

(30) Foreign Application Priority Data

Sep. 17, 2003 (JP) ............................. P. 2003-325198
Mar. 31, 2004 (JP) ............................. P. 2004-101863

(51) Int. Cl.
*C07D 265/36* (2006.01)
*A61K 31/535* (2006.01)
(52) U.S. Cl. ..................................... 544/105; 514/230.5
(58) Field of Classification Search ........................ None
See application file for complete search history.

(56) References Cited

U.S. PATENT DOCUMENTS

| 7,351,705 B2 * | 4/2008 | Iwahashi et al. ........... 514/230.5 |
| 2005/0222216 A1 | 10/2005 | Iwahashi et al. |
| 2007/0167498 A1 | 7/2007 | Asada et al. |

FOREIGN PATENT DOCUMENTS

| CA | 2524235 A1 | 11/2004 |
| WO | 86/05779 A1 | 10/1986 |
| WO | 01/66520 A1 | 9/2001 |
| WO | 03/078409 A1 | 9/2003 |

OTHER PUBLICATIONS

West, Anthony R., Solid State Chemistry and its Applications, Wiley, New York, 1988, pp. 358 & 365.*
"The use of DP receptor antagonists to treat allergic rhinitis", Merck Frosst Canada & Co.: WO0179169, (2002), 12 (4): 597-599.*
Nagai, H. Allergology International 2008, 57,187-96.*
Silva, A.T. et al Advances in Prodrug Design in Mini Revs in Med. Chem., 2005, vol. 5, 893-914.*
Silverman, R. "The Organic Chemistry of Drug Design and Drug Action," 2004, Elsevier, pp. 29-32.*
Nagai, H., Allergology International 2008, vol. 57, pp. 187-196.*
West, Anthony R., Solid State Chemistry and its Applications, Wiley, New York, 1988, pp. 358 and 365.
Wolff, Manfred E. "Burger's Medicinal Chemistry, 5 Ed., Part I", John Wiley & Sons, 1995, pp. 975-977.
Banker, G. S. et al., "Modern Pharmaceutics, 3 Ed.", Marcel Dekker, New York, 1996, pp. 451 and 596.

(Continued)

*Primary Examiner* — Janet L. Andres
*Assistant Examiner* — Heidi Reese
(74) *Attorney, Agent, or Firm* — Sughrue Mion, PLLC

(57) ABSTRACT

A compound represented by formula (I)

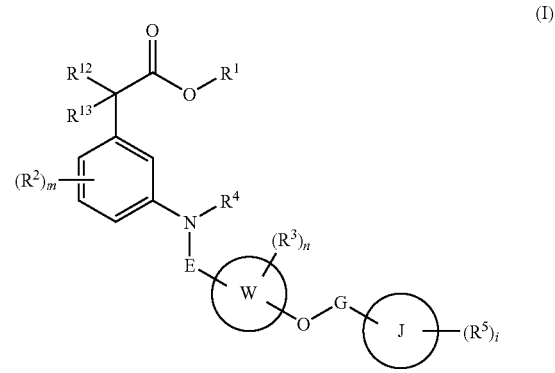

wherein the symbols in the formula are the same meanings as those in specification, salts thereof, solvates thereof, or prodrugs thereof binds to DP receptor and shows antagonistic activity for DP receptor. Thus, it is useful for prevention and/or treatment of diseases such as allergic disease (e.g., allergic rhinitis, allergic conjunctivitis, atopic dermatitis, bronchial asthma and food allergy), systemic mastocytosis, disorders accompanied by systemic mast cell activation, anaphylaxis shock, bronchoconstriction, urticaria, eczema, diseases accompanied by itch (e.g., atopic dermatitis and urticaria), diseases (e.g., cataract, retinal detachment, inflammation, infection and sleeping disorders) which is generated secondarily as a result of behavior accompanied by itch (e.g., scratching and beating), inflammation, chronic obstructive pulmonary diseases, ischemic reperfusion injury, cerebrovascular accident, chronic rheumatoid arthritis, pleurisy, ulcerative colitis, etc. Since it specifically binds to DP receptor and binds weakly to other prostaglandins receptors, they can be pharmaceuticals having little side effect.

2 Claims, No Drawings

OTHER PUBLICATIONS

Notification of Defects issued in counterpart Israeli Patent Application No. 174336 dated Feb. 3, 2010.
Office Action issued on Sep. 1, 2010 in counterpart European Application No. 04773373.8.
Canadian Office Action issued on Nov. 24, 2010 in the corresponding Canadian Patent Application No. 2,539,070.
Matsuoka, T. et., al. "Prostaglandin $D_2$ as a Mediator of Allergic Asthma", Science, vol. 287, Mar. 17, 2000, pp. 2013-2017.
Arimura, A. et., al. "Prevention of Allergic Inflammation by a Novel Prostaglandin Receptor Antagonist, S-5751", The Journal of Pharmacology and Experimental Therapeutics, vol. 298, No. 2, 2001, pp. 411-419.
Kabashima, K. et., al. "The DP receptor, allergic inflammation and asthma", Elsevier Science Ltd., 2003, pp. 187-194.
Office Action dated Feb. 21, 2010 from the Mexican Patent Office in Mexican counterpart application No. PA/a/2006/002945.
Patent Office of the People's Republic of China, Office Action dated Apr. 21, 2011 issued in counterpart Chinese application No. 200480033868.6.

* cited by examiner

CARBOXYLIC ACID COMPOUNDS AND MEDICINAL COMPOSITIONS CONTAINING THE SAME AS THE ACTIVE INGREDIENT

This is a continuation of application Ser. No. 10/572,578 filed Mar. 17, 2006. The entire disclosure(s) of the prior application(s), application number(s) 10/572,578 is hereby incorporated by reference.

TECHNICAL FIELD

The present invention relates to (1) a carboxylic acid compound represented by formula (I)

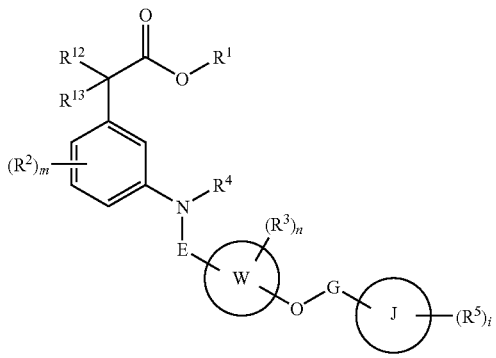

wherein all symbols have the same meanings as follows, salts thereof, solvates thereof, and prodrugs thereof,
(2) a process for producing the same,
(3) a pharmaceutical composition containing the same as an active ingredient, and
(4) a usage for the same.

BACKGROUND OF THE INVENTION

Prostaglandin $D_2$ (abbreviated as $PGD_2$) has been known as one of metabolites produced via an arachidonic acid cascade and is considered to be one of chemical mediators participating in allergic diseases such as allergic rhinitis, bronchial asthma and allergic conjunctivitis. It has been known that $PGD_2$ is mainly produced in and released from mast cells and that the $PGD_2$ released shows contraction of bronchus, promotion of vascular permeability, dilation or contraction of blood vessels, promotion of mucus secretion and inhibition of platelet aggregation. It has been also reported that PGD2 induces bronchoconstriction and nasal obstruction in vivo as well and increased amounts of production of $PGD_2$ in pathological lesion of patients suffering from systemic mastocytosis, allergic rhinitis, bronchial asthma, atopic dermatitis, urticaria, etc. (N. Engl. J. Med. 1989; 303: 1400-4, Am. Rev. Respir. Dis. 1983; 128: 597-602, J. Allergy Clin. Immunol. 1991; 88: 33-42, Arch. Otolaryngol. Head Neck Surg. 1987; 113: 179-83, J. Allergy Clin. Immunol. 1988; 82: 869-77, J. Immunol. 1991; 146: 671-6, J. Allergy Clin. Immunol. 1989; 83: 905-12, N. Eng. J. Med. 1986; 315: 8004, Am. Rev. Respir. Dis. 1990; 142, 126-32, J. Allergy Clin. Immunol. 1991; 87: 540-8, J. Allergy Clin. Immunol 1986; 78: 458-61). $PGD_2$ has been also reported to participate in nerve activity, particularly in sleeping, hormone secretion and pain. Furthermore, it has been also reported that it participates in platelet aggregation, glycogen metabolism and adjustment of intraocular pressure.

$PGD_2$ exerts its biological activity via binding to a DP receptor, which is one of $PGD_2$ receptors. Since DP receptor antagonists bind to its receptor and show antagonistic activity, DP receptor antagonists have been believed to be useful for prevention and/or treatment of diseases such as allergic diseases (e.g., allergic rhinitis, allergic conjunctivitis, atopic dermatitis, bronchial asthma and food allergy), systemic mastocytosis, disorders accompanied by systemic mast cell activation, anaphylactic shock, bronchoconstriction, urticaria, eczema, acne, allergic bronchial pulmonary aspergillosis, sinusitis, migraine, nasal polypus, anaphylactic vasculitis, eosinophilic syndrome, contact dermatitis, diseases accompanied by itch (e.g., atopic dermatitis, urticaria, allergic conjunctivitis, allergic rhinitis and contact dermatitis), diseases (e.g., cataract, retinal detachment, inflammation, infection and sleeping disorders) which are generated secondarily as a result of behavior accompanied by itch (e.g., scratching and beating), inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis, irritable bowel syndrome, interstitial cystitis, muscular dystrophy, polymyositis, multiple sclerosis, etc. It also participates in sleep and platelet aggregation and is believed to be useful for those diseases as well.

For example, in the specification of WO86/05779, compounds represented by formula (T)

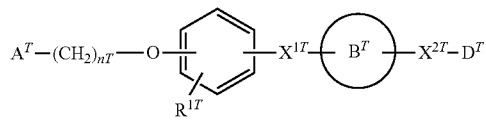

(in the formula, $A^T$ is a hydrogen atom, phenyl or phenoxy; $n^T$ is an integer from 3 to 10; $R^{1T}$ is a hydrogen atom or a lower alkoxy; $X^{1T}$ is —$CH_2$—$Y^{1T}$— (in the group, $Y^{1T}$ is —O—, —S— or —NH—), —CO—$Y^{2T}$-(in the group, $Y^{2T}$ is —O—, —S— or —NH—) etc.;

is a group represented by the formula

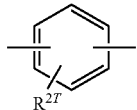

etc.; $R^{2T}$ is a hydrogen atom, a halogen atom, nitro, hydroxyl, lower alkoxy, cyano, lower alkyl, lower alkoxy lower alkyl, halo lower alkyl or a group represented by —$NR^{4T}R^{5T}T$—, etc.; $X^{2T}$ is a formula —$Y^{3T}$—$Y^{4T}$-(in the group, $Y^{3T}$ is a single bond, —O—, —S— or —NH— and $Y^{4T}$ is a C1-6 alkylene which may be interrupted by sulfur atom) etc.; and DT is carboxyl or a lower alkoxycarbonyl and the like) are useful as antagonists for SRS-A (slow reacting substance of anaphylaxis).

DISCLOSURE OF THE INVENTION

In prostaglandin receptors, there are many receptors including subtypes and each of them has a different pharmacological action. Now, if novel compounds that specifically bind to DP receptors and bind weakly to other prostaglandin receptors can be found, they can be pharmaceuticals having little side effect since no other functions are not exerted. Therefore, such pharmaceuticals are requested to be found.

The inventors of the present invention have carried out intensive studies for finding compounds that specifically bind to DP receptors and exert antagonistic activity, and as a result, they have found that carboxylic acid compounds represented by formula (I) resolve the problem to accomplish the present invention.

Thus, the present invention relates to the followings.

1. A carboxylic acid compound represented by formula (I)

(I)

wherein $R^1$ represents (1) a hydrogen atom, (2) C1-4 alkyl, (3) C2-4 alkenyl, or (4) benzyl;

E represents —CO—, —SO$_2$—, or —CH$_2$—;

$R^2$ represents (1) a halogen atom, (2) C1-6 alkyl, (3) C1-6 alkoxy, (4) hydroxyl, (5) trihalomethyl, (6) cyano, (7) phenyl, (8) pyridyl, (9) nitro, (10) —NR$^6$R$^7$, or (11) C1-4 alkyl substituted with —OR$^8$, (12) oxidized C1-6 alkyl, (13) —SO$_2$R$^{11}$, (14) —SOR$^{11}$, or (15) —SR$^{11}$, or two $R^2$'s substituting for the adjacent carbon atom are taken together to represent (1) C2-5 alkylene which may be substituted by a substituent wherein one carbon atom thereof may be replaced with an oxygen atom, a nitrogen atom, or a sulfur atom which may be oxidized, or (2) C2-5 alkenylene which may be substituted by a substituent, wherein one carbon atom thereof may be replaced with an oxygen atom, a nitrogen atom, or a sulfur atom;

$R^3$ represents (1) a halogen atom, (2) C1-6 alkyl, (3) C1-6 alkoxy, (4) hydroxyl, (5) trihalomethyl, (6) cyano, (7) phenyl, (8) pyridyl, (9) nitro, (10) —NR$^6$R$^7$ or (11) C1-4 alkyl substituted with —OR$^8$, (12) oxidized C1-6 alkyl, (13) —SO$_2$R$^{11}$, (14) —SOR$^{11}$, or (15) —SR$^{11}$;

$R^6$ and $R^7$ each independently represent a hydrogen atom or C1-4 alkyl;

$R^8$ represents C1-4 alkyl, phenyl, or pyridyl;

$R^4$ represents (1) a hydrogen atom, (2) C1-6 alkyl, (3) benzyl, or (4) oxidized C1-6 alkyl;

$R^5$ represents (1) C1-6 alkyl, (2) C1-10 alkoxy, (3) C1-6 alkyl substituted with C1-6 alkoxy, (4) a halogen atom, (5) hydroxyl, (6) trihalomethyl, (7) nitro, (8) —NR$^9$R$^{10}$, (9) phenyl, (10) phenoxy, (11) oxo, (12) C2-6 acyl, (13) cyano or (14) —SO$_2$R$^{11}$, (15) —SOR$^{11}$, (16) —SR$^{11}$, (12) oxidized C1-6 alkyl;

$R^9$ and $R^{10}$ each independently represent a hydrogen atom or C1-4 alkyl; and $R^{11}$ represents C1-6 alkyl or phenyl which may be substituted;

wherein $R^6$'s to $R^{11}$'s in $R^2$'s to $R^5$'s may be the same or each independently different:

represents a C5-12 monocyclic or bicyclic carbocyclic ring or a 5- to 12-membered monocyclic or bicyclic heterocycle;

G represents (1) C1-6 alkylene having 0 to 2 hetero atoms selected from a nitrogen atom, an oxygen atom, and a sulfur atom, (2) C2-6 alkenylene having 0 to 2 hetero atoms selected from a nitrogen atom, an oxygen atom, and a sulfur atom, or (3) C2-6 alkynylene having 0 to 2 hetero atoms selected from a nitrogen atom, an oxygen atom, and a sulfur atom;

represents a C5-12 monocyclic or bicyclic carbocyclic ring or a 5- to 12-membered monocyclic or bicyclic heterocycle;

m represents 0 or an integer of 1 to 4, n represents 0 or an integer of 1 to 4, and i represents 0 or an integer of 1 to 11, wherein $R^2$'s may be the same or different when m is 2 or more, $R^3$'s may be the same or different when n is 2 or more, and $R^5$'s may be the same or different when i is 2 or more; and $R^{12}$ and $R^{13}$ each independently represent (1) C1-4 alkyl which may be oxidized, (2) a halogen atom, (3) trihalomethyl, (4) hydroxyl which may be protected, (5) amino which may be protected, (6) phenyl which may be substituted, (7) pyridyl which may be substituted, or (8) a hydrogen atom, or $R^{12}$ and $R^{13}$ are taken together to represent (1) oxo, (2) C2-5 alkylene which may be substituted by a substituent, wherein one carbon atom thereof may be replaced with an oxygen atom, a nitrogen atom, or a sulfur atom, or (3) C1-6 alkylidene which may be substituted, and wherein when $R^{12}$ and $R^{13}$ each simultaneously represent a hydrogen atom, the carboxylic acid compound represented by formula (I) represents a compound selected from the group consisting of the following compounds (1)-(32);

(1) (3-((2,3-dimethyl-4-(((2S)-4-methyl-3,4-dihydro-2H-1, 4-benzoxazin-2-ly)methoxy)benzoyl)amino)-4-fluorophenyl)acetic acid, (2) (4-chloro-3-((2,3-dimethyl-4-(((2S)-4-methyl-3,4-dihydro-2H-1,4-benzoxazin-2-ly)methoxy)benzoyl)amino) phenyl)acetic acid, (3) (4-chloro-3-((2,6-dimethyl-4-(((2S)-4-methyl-3,4-dihydro-2H-1,4-benzoxazin-2-yl)methoxy)benzoyl)amino) phenyl)acetic acid, (4) (4-chloro-3-((5-chloro-2-fluoro-4-(((2S)-4-methyl-3,4-dihydro-2H-1,4-benzoxazin-2-ly)methoxy)benzoyl) amino)phenyl)acetic acid, (5) (4-chloro-3-((2,5-dimethyl-4-(((2S)-4-methyl-3,4-dihydro-2H-1,4-benzoxazin-2-ly)methoxy)benzoyl)amino) phenyl)acetic acid, (6) (4-chloro-3-((2-fluoro-5-methyl-4-(((2S)-4-methyl-3,4-dihydro-2H-1,4-benzoxazin-2-ly)methoxy)benzoyl) amino)phenyl)acetic acid, (7) (4-chloro-3-((2,5-difluoro-4-(((2S)-4-methyl-3,4-dihydro-2H-1,4-benzoxazin-2-ly)methoxy)benzoyl)amino)phenyl)acetic acid,
(8) (3-((2,3-dimethyl-4-(((2S)-4-methyl-3,4-dihydro-2H-1,4-benzoxazin-2-ly)methoxy)benzoyl)amino)-4-methylphenyl)acetic acid,
(9) (3-((2,3-dimethyl-4-(((2S)-4-methyl-3,4-dihydro-2H-1,4-benzoxazin-2-ly)methoxy)benzoyl)amino)-5-methylphenyl)acetic acid,
(10) (3-((2,3-dimethyl-4-(((2S)-4-methyl-3,4-dihydro-2H-1,4-benzoxazin-2-ly)methoxy)benzoyl)amino)phenyl)acetic acid,
(11) (3-((2,6-dimethyl-4-(((2S)-4-methyl-3,4-dihydro-2H-1,4-benzoxazin-2-ly)methoxy)benzoyl)amino)phenyl)acetic acid,
(12) (3-((2,6-dimethyl-4-(((2S)-4-methyl-3,4-dihydro-2H-1,4-benzoxazin-2-ly)methoxy)benzoyl)amino)-5-methylphenyl)acetic acid,
(13) (5-((2,6-dimethyl-4-(((2S)-4-methyl-3,4-dihydro-2H-1,4-benzoxazin-2-ly)methoxy)benzoyl)amino)-2-fluorophenyl)acetic acid,
(14) (5-((2,5-dimethyl-4-(((2S)-4-methyl-3,4-dihydro-2H-1,4-benzoxazin-2-ly)methoxy)benzoyl)amino)-2-methylphenyl)acetic acid,
(15) (5-((2,5-dimethyl-4-(((2S)-4-methyl-3,4-dihydro-2H-1,4-benzoxazin-2-ly)methoxy)benzoyl)amino)-2-fluorophenyl)acetic acid,
(16) (3-((2,5-dimethyl-4-(((2S)-4-methyl-3,4-dihydro-2H-1,4-benzoxazin-2-ly)methoxy)benzoyl)amino)phenyl)acetic acid,
(17) (5-((2,3-dimethyl-4-(((2S)-4-methyl-3,4-dihydro-2H-1,4-benzoxazin-2-ly)methoxy)benzoyl)amino)-2-fluorophenyl)acetic acid,
(18) (5-((2,3-dimethyl-4-(((2S)-4-methyl-3,4-dihydro-2H-1,4-benzoxazin-2-ly)methoxy)benzoyl)amino)-2-methylphenyl)acetic acid,
(19) (5-((2,6-dimethyl-4-(((2S)-4-methyl-3,4-dihydro-2H-1,4-benzoxazin-2-ly)methoxy)benzoyl)amino)-2-methylphenyl)acetic acid,
(20) (3-((2,6-dimethyl-4-(((2S)-4-methyl-3,4-dihydro-2H-1,4-benzoxazin-2-ly)methoxy)benzoyl)amino)-4-methylphenyl)acetic acid,
(21) (3-((2,6-dimethyl-4-(((2S)-4-methyl-3,4-dihydro-2H-1,4-benzoxazin-2-ly)methoxy)benzoyl)amino)-4-fluorophenyl)acetic acid,
(22) (3-((2,5-dimethyl-4-(((2S)-4-methyl-3,4-dihydro-2H-1,4-benzoxazin-2-ly)methoxy)benzoyl)amino)-4-fluorophenyl)acetic acid,
(23) (3-((2,5-dimethyl-4-(((2S)-4-methyl-3,4-dihydro-2H-1,4-benzoxazin-2-ly)methoxy)benzoyl)amino)-4-methylphenyl)acetic acid,
(24) (3-((2,5-dimethyl-4-(((2S)-4-methyl-3,4-dihydro-2H-1,4-benzoxazin-2-ly)methoxy)benzoyl)amino)-5-methylphenyl)acetic acid,
(25) (4-chloro-3-((4-((2R)-2,3-dihydro-1,4-benzodioxin-2-lymethoxy)-2,6-dimethylbenzoyl)amino)phenyl)acetic acid,
(26) (2-chloro-5-((2,3-dimethyl-4-(((2S)-4-methyl-3,4-dihydro-2H-1,4-benzoxazin-2-ly)methoxy)benzoyl)amino)phenyl)acetic acid,
(27) (2-chloro-5-((2,6-dimethyl-4-(((2S)-4-methyl-3,4-dihydro-2H-1,4-benzoxazin-2-ly)methoxy)benzoyl)amino)phenyl)acetic acid,
(28) (2-chloro-5-((2,5-dimethyl-4-(((2S)-4-methyl-3,4-dihydro-2H-1,4-benzoxazin-2-ly)methoxy)benzoyl)amino)phenyl)acetic acid,
(29) (4-chloro-3-((4-((3R)-2,3-dihydro-1-benzofuran-3-lymethoxy)-2,6-dimethylbenzoyl)amino)phenyl)acetic acid,
(30) (4-chloro-3-((2,6-dimethyl-4-(((3R)-5-methyl-2,3-dihydro-1-benzofuran-3-ly)methoxy)benzoyl)amino)phenyl)acetic acid,
(31) (4-chloro-3-((4-((2S)-2,3-dihydro-1-benzofuran-2-lymethoxy)-2,6-dimethylbenzoyl)amino)phenyl)acetic acid, and
(32) (3-((4-(1,3-benzodioxol-2-lymethoxy)-2,6-dimethylbenzoyl)amino)-4-chlorophenyl)acetic acid, a salt thereof, a solvate thereof, or a prodrug thereof.

2. The compound according to 1 above, wherein

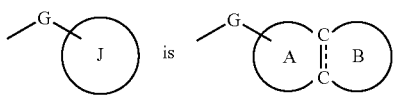

wherein

represents C5-6 saturated carbocyclic ring, or 5- to 6-membered saturated heterocycle containing one or two nitrogen atoms, one or two oxygen atoms, and/or a sulfur atom;

represents C5-6 saturated carbocyclic ring, or 5- to 6-membered saturated heterocycle containing one or two nitrogen atoms, one or two oxygen atoms, and/or a sulfur atom;
----- represents a single bond or a double bond; and
the other symbols have the same meanings as defined in 1 above, a salt thereof, a solvate thereof, or a prodrug thereof.

3. The compound according to 2 above, wherein

is a group selected from dihydrobenzoxazin-2-yl, benzodioxan-2-yl, benzoxathiane-2-yl, dihydrobenzofuran-2-yl, dihydrobenzofuran-3-yl, benzodioxol-2-yl, indolin-2-yl, and indolin-3-yl.

4. The compound according to 2 above, wherein n is an integer of 2 to 4.

5. The compound according to 4 above, wherein

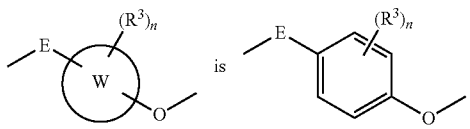

wherein all symbols have the same meanings as defined in 1 above.

6. The compound according to 5 above, wherein

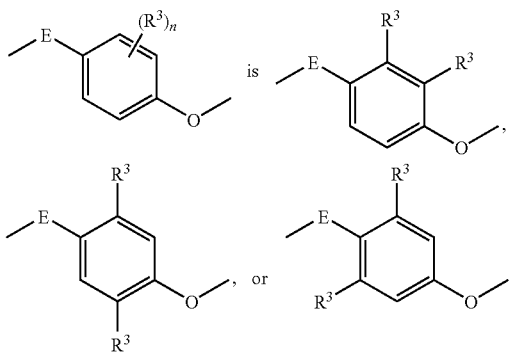

wherein all symbols have the same meanings as defined in 1 above.

7. The compound according to 6 above, wherein $R^3$'s each independently represent (1) a halogen atom, (2) C1-6 alkyl, (3) C1-6 alkoxy, or (4) trihalomethyl.

8. The compound according to 2 above, wherein $R^{12}$ and $R^{13}$ each independently represent (1) C1-4 alkyl, (2) a halogen atom, (3) hydroxyl which may be protected, or (4) a hydrogen atom, or $R^{12}$ and $R^{13}$ are taken together to represent (1) oxo or (2) C2-5 alkylene which may be substituted by a substituent, wherein one carbon atom thereof may be replaced with an oxygen atom, a nitrogen atom, or a sulfur atom.

9. The compound according to 7 above, which is selected from:
(1) 2-(4-chloro-3-((2-chloro-4-(((2S)-4-methyl-3,4-dihydro-2H-1,4-benzoxazin-2-ly)methoxy)benzoyl)amino)phenyl)-2-methylpropanoic acid,
(2) (4-chloro-3-((2-chloro-4-(((2S)-4-methyl-3,4-dihydro-2H-1,4-benzoxazin-2-ly)methoxy)benzoyl)amino)phenyl)(difluoro)acetic acid,
(3) (4-chloro-3-((2-chloro-4-(((2S)-4-methyl-3,4-dihydro-2H-1,4-benzoxazin-2-ly)methoxy)benzoyl)amino)phenyl)(oxo)acetic acid,
(4) 2-(4-chloro-3-((2,5-dimethyl-4-(((2S)-4-methyl-3,4-dihydro-2H-1,4-benzoxazin-2-ly)methoxy)benzoyl)amino)phenyl)-2-methylpropanoic acid,
(5) 2-(4-chloro-3-((2,6-dimethyl-4-(((2S)-4-methyl-3,4-dihydro-2H-1,4-benzoxazin-2-ly)methoxy)benzoyl)amino)phenyl)-2-methylpropanoic acid,
(6) 2-(3-((2,5-dimethyl-4-(((2S)-4-methyl-3,4-dihydro-2H-1,4-benzoxazin-2-ly)methoxy)benzoyl)amino)-4-methylphenyl)-2-methylpropanoic acid,
(7) 1-(4-chloro-3-((2,6-dimethyl-4-(((2S)-4-methyl-3,4-dihydro-2H-1,4-benzoxazin-2-ly)methoxy)benzoyl)amino)phenyl)cyclopropanecarboxylic acid,
(8) 1-(4-chloro-3-((2,5-dimethyl-4-(((2S)-4-methyl-3,4-dihydro-2H-1,4-benzoxazin-2-ly)methoxy)benzoyl)amino)phenyl)cyclopropanecarboxylic acid,
(9) 1-(4-chloro-3-((2-ethyl-4-(((2S)-4-methyl-3,4-dihydro-2H-1,4-benzoxazin-2-ly)methoxy)benzoyl)amino)phenyl)cyclopropanecarboxylic acid,
(10) (4-chloro-3-((2,6-dimethyl-4-(((2S)-4-methyl-3,4-dihydro-2H-1,4-benzoxazin-2-ly)methoxy)benzoyl)amino)phenyl)acetic acid, and
(11) (3-((2,6-dimethyl-4-(((2S)-4-methyl-3,4-dihydro-2H-1,4-benzoxazin-2-ly)methoxy)benzoyl)amino)-5-methylphenyl)acetic acid.

10. A pharmaceutical composition comprising a compound represented by formula (I)

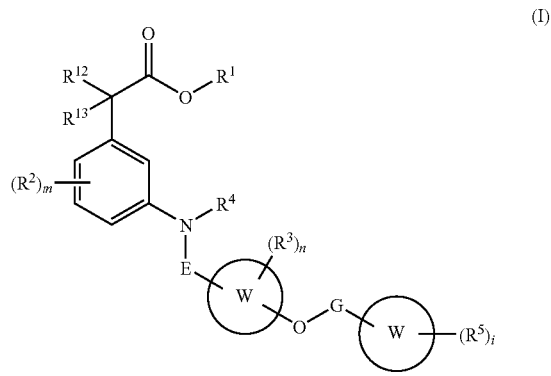

wherein all symbols have the same meanings as defined in 1 above, a salt thereof, a solvate thereof, or a prodrug thereof.

11. The pharmaceutical composition according to 10 above, which is an antagonist of DP receptor.

12. The pharmaceutical composition according to 10 above, which is an agent for prevention and/or treatment of diseases mediated by DP receptor.

13. The pharmaceutical composition according to 12 above, wherein the disease mediated by DP receptor is allergic disease, systemic mastocytosis, disorders accompanied by systemic mast cell activation, anaphylaxis shock, bronchoconstriction, urticaria, eczema, acne, allergic bronchial pulmonary aspergillosis, sinusitis, migraine, nasal polypus, anaphylactic vasculitis, eosinophilic syndrome, contact dermatitis, diseases accompanied by itch, diseases generated secondarily as a result of behavior accompanied by itch, inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis, irritable bowel syndrome, interstitial cystitis, muscular dystrophy, polymyositis, multiple sclerosis, sleeping disorders or disease related to platelet aggregation.

14. The pharmaceutical composition according to 13 above, wherein the allergic disease is allergic rhinitis, allergic conjunctivitis, atopic dermatitis, bronchial asthma or food allergy.

15. A pharmaceutical composition comprising a combination of the compound represented by formula (I) according to 1 above, a salt thereof, a solvate thereof, or a prodrug thereof; and one or more kinds selected from antihistaminic agent, suppressor for mediator liberation, thromboxane synthetase inhibitor, antagonist for thromboxane A2 receptor, antagonist for leukotriene receptor, steroid agent, alpha-adrenergic receptor stimulator, xanthine derivative, anticholinergic agent, and nitric oxide synthase inhibitor.

16. Use of the compound represented by formula (I) according to 1 above, a salt thereof, a solvate thereof, or a prodrug thereof for the production of a pharmaceutical composition for prevention and/or treatment of diseases mediated by DP receptor.

17. Use of the compound represented by formula (I) according to 1 above, a salt thereof, a solvate thereof, or a prodrug thereof for the production of an antagonist of DP receptor.

18. A method for prevention and/or treatment of diseases mediated by DP receptor, which comprises administering to a mammal an effective amount of the compound represented by formula (I) according to 1 above, a salt thereof, a solvate thereof, or a prodrug thereof.

In the present specification, C1-4 alkyl includes linear and branched alkyl such as methyl, ethyl, propyl, isopropyl, butyl, isobutyl, sec-butyl, and tert-butyl.

In the present specification, C1-6 alkyl includes linear and branched alkyl such as methyl, ethyl, propyl, isopropyl, butyl, isobutyl, sec-butyl, tert-butyl, pentyl, isopentyl, neopentyl, hexyl, and isohexyl.

In the present specification, C2-4 alkenyl includes linear and branched alkenyl such as ethenyl, propenyl, and butenyl.

In the present specification, C1-6 alkoxy includes linear and branched alkoxy such as methoxy, ethoxy, propoxy, isopropoxy, butoxy, isobutoxy, sec-butoxy, tert-butoxy, pentyloxy, isopentyloxy, neopentyloxy, hexyloxy, and isohexyloxy.

In the present specification, C1-10 alkoxy includes linear and branched alkoxy selected from methoxy, ethoxy, propoxy, isopropoxy, butoxy, isobutoxy, sec-butoxy, tert-butoxy, pentyloxy, isopentyloxy, neopentyloxy, hexyloxy, isohexyloxy, heptyloxy, octyloxy, nonyloxy, and decyloxy.

In the present specification, C2-6 acyl includes linear and branched acyl such as ethanoyl, propanoyl, butanoyl, 2-methylpropanoyl, pentanoyl, 2-methylbutanoyl, 3-methylbutanoyl, hexanoyl, 2-methylpentanoyl, 3-methylpentanoyl, 4-methylpentanoyl, 2-ethylbutanoyl, and 2,3-dimethylbutanoyl.

In the present specification, a halogen atom includes such as a fluorine atom, a chlorine atom, a bromine atom, and an iodine atom.

In the present specification, trihalomethyl is methyl substituted by three halogen atoms.

In the present specification, C1-4 alkylene includes linear or branched alkylene such as methylene, ethylene, propylene, isopropylene, butylenes, and isobutylene.

In the present specification, C2-4 alkenylene includes linear or branched alkenylene such as vinylene, propenylene, 1- or 2-butenylene, and butadienylene. In the present specification, C2-4 alkynylene includes linear or branched alkynylene such as ethynylene, 1- or 2-propynylene and 1- or 2-butynylene.

In the present specification, C1-6 alkylene containing 0 to 2 hetero atom(s) selected from a nitrogen atom, an oxygen atom, and a sulfur atom includes linear or branched alkylene such as: methylene, ethylene, propylene, isopropylene, butylene, isobutylene, pentylene, and hexylene, or linear or branched C1-6 alkylene in which one or two carbon atom(s) in methylene, ethylene, propylene, isopropylene, butylene, isobutylene, pentylene, and hexylene is/are substituted by one or two hetero atom(s) selected from a nitrogen atom (a residual bond in the said nitrogen atom binds to a hydrogen atom, C1-6 alkyl, C2-6 acyl, or C1-6 alkoxycarbonyl (e.g., methoxycarbonyl, ethoxycarbonyl, tert-butoxycarbonyl etc.)), an oxygen atom, and a sulfur atom, e.g., linear or branched C1-6 alkylene containing one or two hetero atom(s) selected from a nitrogen atom, an oxygen atom, and a sulfur atom in —(CH$_2$)$_2$—NH—, —(CH$_2$)$_2$—N(CH$_3$)—, —(CH$_2$)$_2$—O—, —(CH$_2$)$_2$—S—, —(CH$_2$)$_3$—NH—, —CH$_2$)$_3$—N(CH$_3$)—, —CH$_2$—CH(CH$_3$)—CH$_2$—NH—, —CH$_2$—CH(CH$_3$)—CH$_2$—N(CH$_3$)—, —(CH$_2$)$_3$—O— and —(CH$_2$)$_3$—S—, wherein only a carbon atom in the alkylene binds to an adjacent —O—.

In the present specification, C2-6 alkenylene having 0 to 2 hetero atom(s) selected from a nitrogen atom, an oxygen atom, and a sulfur atom includes linear or branched alkenylene such as vinylene, propenylene, 1- or 2-butenylene, butadienylene, pentenylene and hexenylene, or C2-6 alkenylene in which one or two carbon atom(s) in vinylene, propenylene, 1- or 2-butenylene, butadienylene, pentenylene, and hexenylene is/are substituted with one or two hetero atom(s) selected from a nitrogen atom (a residual bond in the said nitrogen atom binds to a hydrogen atom, C1-6 alkyl, C2-6 acyl, or the C1-6 alkoxycarbonyl (e.g., methoxycarbonyl and ethoxycarbonyl, tert-butoxycarbonyl etc.)), an oxygen atom, and a sulfur atom, e.g., linear or branched C2-6 alkenylene containing one or two hetero atom(s) selected from a nitrogen atom, an oxygen atom, and a sulfur atom in —CH═CH—NH—, —CH═CH—N(CH$_3$)—, —CH═CH—O—, —CH═CH—S—, —CH═CH—CH$_2$—NH—, —CH═CH—CH$_2$—N(CH$_3$)—, —CH═CH—CH$_2$—O—, and —CH═CH—CH$_2$—S—, wherein only a carbon atom in the alkenylene binds to an adjacent —O—.

In the present specification, C2-6 alkynylene having 0 to 2 hetero atom(s) selected from an nitrogen atom, an oxygen atom, and a sulfur atom includes linear or branched alkynylene such as ethynylene, 1- or 2-propynylene, 1- or 2-butynylene, pentynylene, and hexynylene or C2-6 alkynylene in which one or two carbon atom(s) in ethynylene, 1- or 2-propynylene, 1- or 2-butynylene, pentynylene, hexynylene, and hexynylene is/are substituted with one or two hetero atom(s) selected from a nitrogen atom (a residual bond in the said nitrogen atom binds to a hydrogen atom, C1-6 alkyl, C2-6 acyl, or the C1-6 alkoxycarbonyl (e.g., methoxycarbonyl, ethoxycarbonyl, tert-butoxycarbonyl etc.)), an oxygen atom, and a sulfur atom, e.g., linear or branched C2-6 alkynylene containing one or two hetero atom(s) selected from a nitrogen atom, an oxygen atom, and a sulfur atom in —C≡C—NH—, —C≡C—N(CH$_3$)—, —C≡C—O—, —C≡C—S—, —C≡C—CH$_2$—NH—, —C≡C—CH$_2$—N(CH$_3$)—, —C≡C—CH$_2$—O—, and —C≡C—CH$_2$—S—, wherein only a carbon atom in the alkenylene binds to an adjacent —O—.

In the present specification, oxidized C1-6 alkyl includes C1-6 alkyl substituted by 1 to 3 hydroxyl group(s) and/or 1 to 3 oxo group(s), wherein the carbon atom to which two or more hydroxyl groups and/or oxo groups bind is limited to the carbon atom in the terminal position, such as hydroxymethyl, formyl, carboxy, 2-hydroxyethyl, 2-oxoethyl, carboxymethyl, 1-hydroxyethyl, acetyl, 3-hydroxypropyl, 3-oxopropyl, 2-carboxyethyl, 2-hydroxypropyl, 2-oxopropyl, 1-hydroxy-1-methylethyl, 4-hydroxybutyl, 4-oxobutyl, 3-carboxypropyl, 3-hydroxybutyl, 3-oxobutyl, 3-hydroxy-2-methylpropyl, 2-methyl-3-oxopropyl, 2-carboxypropyl, 2-hydroxy-2-methylpropyl, 3-hydroxy-1-methylpropyl, 1-methyl-3-oxopropyl, 2-carboxy-1-methylethyl, 2-hydroxy-1-methylpropyl, 1-methyl-2-oxopropyl, 1-hydroxy-1-methylpropyl, 1-hydroxymethylpropyl, 1-formylpropyl, 1-carboxypropyl, 2-hydroxy-1,1-dimethylethyl, 1,1-dimethyl-2-oxoethyl, and 1-carboxy-1-methylethyl etc.

In the present specification, C1-4 alkyl that may be oxidized includes C1-4 alkyl that may be substituted by 1 to 3 hydroxyl group(s) and/or 1 to 3 oxo group(s), wherein the carbon atom to which two or more hydroxyl groups and/or oxo groups bind is limited to the carbon atom in the terminal position, such as linear or branched C1-4 alkyl such as methyl, ethyl, propyl, isopropyl, butyl, isobutyl, sec-butyl, and tert-butyl, hydroxymethyl, formyl, carboxy, 2-hydroxyethyl, 2-oxoethyl, carboxymethyl, 1-hydroxyethyl, acetyl, 3-hydroxypropyl, 3-oxopropyl, 2-carboxyethyl, 2-hydroxypropyl, 2-oxopropyl, 1-hydroxy-1-methylethyl, 4-hydroxybutyl, 4-oxobutyl, 3-carboxypropyl, 3-hydroxybutyl, 3-oxobutyl, 3-hydroxy-2-methylpropyl, 2-methyl-3-oxopropyl, 2-carboxypropyl, 2-hydroxy-2-methylpropyl, 3-hydroxy-1-methylpropyl, 1-methyl-3-oxopropyl, 2-carboxy-1-methylethyl, 2-hydroxy-1-methylpropyl, 1-methyl-2-oxopropyl, 1-hydroxy-1-methylpropyl, 1-hydroxymethylpropyl, 1-formylpropyl, 1-carboxypropyl, 2-hydroxy-1,1-dimethylethyl, 1,1-dimethyl-2-oxoethyl, 1-carboxy-1-methylethyl, etc.

In the present specification, a protective group in "hydroxyl that may be protected" and "amino that may be protected" includes, e.g., alkyl that may have substituents, carbocyclic ring that may have substituent(s), heterocycle that may have substituent(s), alkylsulfonyl (e.g., C1-4 alkylsulfonyl etc., such as methylsulfonyl, ethylsulfonyl, etc.), aromatic ring sulfonyl (e.g., C6-10 aromatic ring sulfonyl etc., such as phenylsulfonyl etc.), acyl groups, etc. Alkyl in "alkyl that may have substituent(s)" includes, e.g, linear or branched C1-20 alkyl such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, etc. Here, the substituent in "alkyl that may have substituent(s)" includes hydroxyl, amino, carboxy, nitro, azide, mono- or di-C1-6 alkylamino group (e.g., methylamino, ethylamino, propylamino, dimethylamino, diethylamino, etc.), N-aromatic ring-amino group (e.g., N-phenylamino etc.), N-aromatic ring-N-alkylamino group (e.g., N-phenyl-N-methylamino, N-phenyl-N-ethylamino, N-phenyl-N-propylamino, N-phenyl-N-butylamino, N-phenyl-N-pentyl amino, N-phenyl-N-hexyl amino, etc.), C1-6 alkoxy (e.g., methoxy, ethoxy, propoxy, isopropoxy, hexyloxy, etc.), C3-7 cycloalkyl-C1-6 alkoxy group (e.g., cyclohexylmethyloxy, cyclopentylethyloxy, etc.), C3-7 cycloalkyloxy (e.g., cyclohexyloxy etc.), C7-15 aralkyloxy (e.g., benzyloxy, phenethyoxy, phenylpropyloxy, naphthylmethyloxy, naphthylethyloxy, etc.), phenoxy, C1-6 alkoxycarbonyl (e.g., tut methoxycarbony, ethoxycarbonyl, tert-butoxycarbonyl, etc.), C1-6 alkylcarbonyloxy (e.g., acetoxy, ethyl carbonyloxy, etc.), C1-4 alkylthio (e.g., methylthio, ethylthio, propylthio, butylthio, etc.), a halogen atom (a fluorine atom, a chlorine atom, a bromine atom, and an iodine atom), alkylsulfonyl (e.g., C1-4 alkylsulfonyl etc., such as methylsulfonyl, ethylsulfonyl, etc.), aromatic ring-sulfonyl group (e.g., C6-10 aromatic ring-sulfonyl group etc., such as phenylsulfonyl etc.), acyl (e.g., C1-6 alkanoyl etc., such as formyl, acetyl, propanoyl, and pivaloyl, and C6-10 aromatic ring-carbonyl group etc., such as benzoyl etc.), etc. The alkyl may be substituted by 1 to 4 arbitrary substituent(s) in the replaceable position. The carbocyclic ring in "carbocyclic ring that may have substituent(s)" includes C3-15 monocyclic, dicyclic, or tricyclic aromatic carbocyclic ring that may be saturated either wholly or partially.

C3-15 monocyclic, dicyclic, or tricyclic aromatic carbocyclic ring that may be saturated either wholly or partially includes cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopropene, cyclobutene, cyclopentene, cyclohexene, cycloheptene, cyclooctene, cyclopentadiene, cyclohexadiene, cycloheptadiene, cyclooctadiene, benzene, pentalene, azulene, perhydroazulene, perhydropentalene, indene, perhydroindene, indane, naphthalene, tetrahydronaphthalene, perhydronaphthalene, heptalene, biphenylene, as-indacene, s-indacene, acenaphthylene, acenaphthene, fluorene, phenalene, phenanthrene, anthracene, etc.

C3-15 monocyclic, dicyclic, or tricyclic aromatic carbocyclic ring that may be saturated either wholly or partially includes bicyclic carbocyclic ring containing spiro bond and constructed bicyclic carbocyclic ring such as spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.3.1]hept-2-ene, bicyclo[2.2.2]octane, bicyclo[2.2.2]oct-2-ene, adamantine, noradamantane ring, etc.

Here, the substituent in "carbocyclic ring that may have substituent(s)" includes C1-8 alkyl (e.g., methyl, ethyl, n-propyl, isopropyl, n-butyl, isobutyl, sec-butyl, tert-butyl, pentyl, hexyl, heptyl, octyl, etc.), hydroxyl, amino, carboxyl, nitro, mono- or di-C1-6 alkylamino (e.g., methylamino, ethylamino, propylamino, dimethylamino, diethylamnino, etc.), C1-6 alkoxy (e.g., methoxy, ethoxy, propoxy, hexyloxy, etc.), C1-6 alkoxycarbonyl (e.g., tert-methoxycarbonyl, ethoxycarbonyl, tert-butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), halogen atom (fluoro atom, chloro atom, bromo atom, and iodo atom), trihalomethyl (e.g., trifluoromethyl etc.), etc. The carbocyclic ring may be substituted by 1 to 4 arbitrary substituent(s) in the replaceable position. The heterocycle in "heterocycle that may have substituent(s)" includes 3- to 15-membered monocyclic, dicyclic, or tricyclic aromatic heterocycle that may be saturated either wholly or partially, containing 1 to 5 hetero atom(s) selected from a nitrogen atom, an oxygen atom, and a sulfur atom. Among 3- to 15-membered monocyclic, dicyclic, or tricyclic heterocycle that may be saturated either wholly or partially containing 1 to 5 hetero atom(s) selected from an oxygen atom, a nitrogen atom or a sulfur atom, 3- to 15-membered monocyclic, dicyclic, or tricyclic aromatic heterocycle containing 1 to 5 hetero atom(s) selected from an oxygen atom, a nitrogen atom, or a sulfur atom includes, e.g., pyrrole, imidazole, triazole, tetrazole, pyrazol, pyridine, pyrazine, pyrimidine, pyridazine, azepine, diazepine, furan, pyran, oxepin, thiophene, thiin, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepin, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiine, thianthrene, phenanthridine, phenanthroline, perimidine ring, etc. Among 3- to 15-membered monocyclic, dicyclic, or tricyclic heterocycle that may be saturated either wholly or partially containing 1 to 5 hetero atom(s) selected from an oxygen atom, a nitrogen atom or a sulfur atom, 3- to 15-membered monocyclic, dicyclic, or tricyclic heterocycle that was saturated either wholly or partially containing 1 to 5 hetero atom(s) selected from an oxygen atom, a nitrogen atom or a sulfur atom includes aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazin, tetrahydropyridazine, perhydropyridazine, dihydroazepine; tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiin(dihydrothiopyran), tetrahydrothiin (tetrahydrothiopyran), dihydrothiepin, tetrahydrothiepin, perhydrothiepin, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydroxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, indoline, isoindolin, dihydrobenzofuran, perhydrobenzofuran, dihydroisobenzofuran, perhydroisobenzofuran, dihydrobenzothiophene, perhydrodibenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzooxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzooxazepine, tetrahydrobenzooxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxan, chroman, benzodithiolane, and benzodithiane ring, etc. Here, the substituent in "heterocycle that may have substituent(s)" includes C1-8 alkyl (e.g., methyl, ethyl, n-propyl, isopropyl, n-butyl, isobutyl, sec-butyl, tert-butyl, pentyl, hexyl, heptyl, octyl, etc.), hydroxyl, amino, carboxyl, nitro, mono- or di-C1-6 alkylamino (e.g., methylamino, ethylamino, propylamino, dimethylamino, diethylamino, etc.), C1-6 alkoxy (e.g., methoxy, ethoxy, propoxy, hexyloxy, etc.), C1-6 alkoxycarbonyl (e.g., tert-methoxycarbonyl, ethoxycarbonyl, tert-butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), a halogen atom (a fluorine atom, a chlorine atom, a bromine atom, and an iodine atom), triharomethyl (e.g., trifluoromethyl etc.), etc. The heterocycle may be substituted by 1 to 4 arbitrary substituent(s) in the replaceable position. The acyl includes (1) alkylcarbonyl that may have substituent(s), (2) alkenylcarbonyl that may have substituent(s), (3) alkynylcarbonyl that may have substituent(s), (4) carbocyclic carbonyl group that may have substituent(s), (5) heterocyclic carbonyl group that may have substituent(s). The acyl may be substituted by 1 to 4 arbitrary substituent(s) in the replaceable position. The alkyl that may have substituent(s) in "alkylcarbonyl that may have substituent(s)" means the same as "alkyl that may have the substituent(s)". The alkenyl that may have substituent(s) in "alkenylcarbonyl that may have substituent(s)" includes, e.g., linear or branched C2-20 alkenyl group etc., such as ethenyl, propenyl, butenyl, pentenyl, hexenyl, etc. Here, the substituent in the alkenyl means the same as the substituent in the aforementioned "alkyl that may have substituent(s)". The alkynyl that may have substituent(s) in "alkynylcarbonyl that may have substituent(s)" includes, e.g., linear or branched C2-20 alkynyl group etc., such as ethynyl, propynyl, butynyl, pentynyl, hexynyl, etc. Here, the substituent in the alkynyl means the same as the substituent in the aforementioned "alkynyl that may have substituent(s)". The carbocyclic ring that may have substituent(s) in "carbocyclic carbonyl group that may have substituent(s)" means the same as the aforementioned "carbocyclic ring that may have substituent(s)". The carbocyclic ring that may have substituent(s) in "heterocyclic carbonyl that may have substituent(s)" means the same as the aforementioned "carbocyclic ring that may have substituent(s)".

In the present specification, the substituent in "phenyl that may have substituent(s)" includes C1-8 alkyl (e.g., methyl, ethyl, n-propyl, isopropyl, n-butyl, isobutyl, sec-butyl, tert-butyl, pentyl, hexyl, heptyl, octyl, etc.), hydroxyl, amino, carboxyl, nitro, mono- or di-C1-6 alkylamino (e.g., methylamino, ethylamino, propylamino, dimethylamino, diethylamino, etc.), C1-6 alkoxy (e.g., methoxy, ethoxy, propoxy, hexyloxy, etc.), C1-6 alkoxycarbonyl (e.g., tert-methoxycarbonyl, ethoxycarbonyl, tert-butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), a halogen atom (a fluorine atom, a chlorine atom, a bromine atom, and an iodine atom), trihalomethyl (e.g., trifluoromethyl etc.), etc. The phenyl may be substituted by 1 to 4 arbitrary substituent(s) in the replaceable position. In the present specification, the substituent in "pyridyl that may have substituent(s)" includes C1-8 alkyl (e.g., methyl, ethyl, n-propyl, isopropyl, n-butyl, isobutyl, sec-butyl, tert-butyl, pentyl, hexyl, heptyl, octyl, etc.), hydroxyl, amino, carboxyl, nitro, mono- or di-C1-6 alkylamino (e.g., methylamino, ethylamino, propylamino, dimethylamino, diethylamino, etc.), C1-6 alkoxy (e.g., methoxy, ethoxy, propoxy, hexyloxy, etc.), C1-6 alkoxycarbonyl (e.g., tert-methoxycarbonyl, ethoxycarbonyl, tert-butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), a halogen atom (a fluorine atom, a chlorine atom, a bromine atom, and an iodine atom), trihalomethyl (e.g., trifluoromethyl etc.), etc. The pyridyl may be substituted by 1 to 4 arbitrary substituent(s) in the replaceable position.

In the present specification, the C2-5 alkylene in which the carbon atom may replace an oxygen atom, a nitrogen atom, or a sulfur atom includes linear or branched C2-5 alkylene such as ethylene, propylene, iso-propylene, butylene, iso-butylene, pentylene, etc., C2-5 alkylene, etc., in which the carbon atom in ethylene, propylene, iso-propylene, butylene, iso-butylene, or pentylene may be replaced with an oxygen atom, a nitrogen atom, or a sulfur atom.

The residual bond in the nitrogen atom binds to a hydrogen atom, C1-6 alkyl, C2-6 acyl, or C1-6 alkoxycarbonyl (e.g., methoxycarbonyl, ethoxycarbonyl, tert-butoxycarbonyl, etc.). The C2-5 alkylene may be substituted by substituent(s). Here, the substituent includes C1-8 alkyl (e.g., methyl, ethyl, n-propyl, isopropyl, n-butyl, isobutyl, sec-butyl, tert-butyl, pentyl, hexyl, heptyl, octyl, etc.), hydroxyl, amino, carboxyl, nitro, mono- or di-C1-6 alkylamino (e.g., methylamino, ethylamino, propylamino, dimethylamino, diethylamino, etc.), C1-6 alkoxy (e.g., methoxy, ethoxy, propoxy, hexyloxy, etc.), C1-6 alkoxycarbonyl (e.g., tert-methoxycarbonyl, ethoxycarbonyl, tert-butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), a halogen atom (a fluorine atom, a chlorine atom, a bromine atom, and an iodine atom), trihalomethyl (e.g., trifluoromethyl etc.), etc. The C2-5 alkylene may be substituted by 1 to 4 arbitrary substituent(s) in the replaceable position.

The C2-5 alkylene includes, e.g., —(CH$_2$)$_2$—, —(CH$_2$)$_3$—, —(CH$_2$)$_4$—, —(CH$_2$)$_5$—, —O—CH$_2$—, —O—(CH$_2$)$_2$—, —O—(CH$_2$)$_3$—, —O—(CH$_2$)$_4$—, —CH$_2$—O—CH$_2$—, —CH$_2$—O—(CH$_2$)$_2$—, —CH$_2$—O—(CH$_2$)$_3$—, —(CH$_2$)$_2$—O—(CH$_2$)$_2$—, —NH—CH$_2$—, —NH—(CH$_2$)$_2$—, —NH—(CH$_2$)$_3$—, —NH—(CH$_2$)$_4$—, —CH$_2$—NH—CH$_2$—, —CH$_2$—NH—(CH$_2$)$_2$—, —CH$_2$—NH—(CH$_2$)$_3$—, —(CH$_2$)$_2$—NH—(CH$_2$)$_2$—, —N(CH$_3$)—CH$_2$—, —N(CH$_3$)—(CH$_2$)$_2$—, —N(CH$_3$)—(CH$_2$)$_3$—, —N(CH$_3$)—(CH$_2$)$_4$—, —CH$_2$—N(CH$_3$)—CH$_2$—, —CH$_2$—N(CH$_3$)—(CH$_2$)$_2$—, —CH$_2$—N(CH$_3$)—(CH$_2$)$_3$—, —(CH$_2$)$_2$—N(CH$_3$)—(CH$_2$)$_2$—, —S—CH$_2$—, —S—(CH$_2$)$_2$—, —S—(CH$_2$)$_3$—, —S—(CH$_2$)$_4$—, —CH$_2$—S—CH$_2$—, —CH$_2$—S—(CH$_2$)$_2$—, —CH$_2$—S—(CH$_2$)$_3$—, —(CH$_2$)$_2$—S—(CH$_2$)$_2$—, etc.

In the present specification, the C2-5 alkenylene in which the carbon atom may replace an oxygen atom, a nitrogen atom, or a sulfur atom includes linear or branched C2-5 alkenylene such as vinylene, propenylene, iso-propenylene, butenylene, iso-butenylene, pentenylene, etc., or C2-5 alkenylene etc., in which the carbon atom in vinylene, propenylene, iso-propenylene, butenylene, iso-butenylene, or pentenylene replaces an oxygen atom, a nitrogen atom, or a sulfur atom. The residual bond in the nitrogen atom binds to a hydrogen atom, C1-6 alkyl, C2-6 acyl, or C1-6 alkoxycarbonyl (e.g., methoxycarbonyl, ethoxycarbonyl, tert-butoxycarbonyl, etc.). The C2-5 alkenylene may be substituted by substituent(s). Here, the substituent includes C1-8 alkyl (e.g., methyl, ethyl, n-propyl, isopropyl, n-butyl, isobutyl, sec-butyl, tert-butyl, pentyl, hexyl, heptyl, octyl, etc.), hydroxyl, amino, carboxyl, nitro, mono- or di-C1-6 alkylamino (e.g., methylamino, ethylamino, propylamino, dimethylamino, diethylamino, etc.), C1-6 alkoxy (e.g., methoxy, ethoxy, propoxy, hexyloxy, etc.), C1-6 alkoxycarbonyl (e.g., tert-methoxycarbonyl, ethoxycarbonyl, tert-butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), a halogen atom (a fluorine atom, a chlorine atom, a bromine atom, and an iodine atom), trihalomethyl (e.g., trifluoromethyl etc.), etc. The C2-5 alkenylene may be substituted by 1 to 4 arbitrary substituent(s) in the replaceable position. The C2-5 alkenylene includes, e.g., —CH=CH—CH=CH—, —CH=CH—CH=N—, —CH=CH—NH—, —CH=CH—S—, —CH=CH—O—, —N=CH—NH—, etc.

In the present specification, the C1-6 alkylidene in "C1-6 alkylidene may be substituted" includes, e.g., methylidene, ethylidene, propylidene, butylidene, pentylidene, hexylidene, etc. Here, the substituent in "C1-6 alkylidene may be substituted" includes hydroxyl, amino, carboxyl, nitro, azido, mono- or di-C1-6 alkylamino (e.g., methylamino, ethylamino, propylamino, dimethylamino, diethylamino, etc.), N-aromatic ring-amino group (e.g., N-phenylamino etc.), N-aromatic ring-N-alkylamino group (e.g., N-phenyl-N-methylamino, N-phenyl-N-ethylamino, N-phenyl-N-propylamino, N-phenyl-N-butylamino, N-phenyl-N-pentyl amino, N-phenyl-N-hexyl amino, etc.), C1-6 alkoxy (e.g., methoxy, ethoxy, propoxy, isopropoxy, hexyloxy, etc.), C3-7 cycloalkyl-C1-6 alkoxy (e.g., cyclohexylmethyloxy, cyclopentylethyloxy, etc.), C3-7 cycloalkyloxy (e.g., cyclohexyloxy etc.), C7-15 aralkyloxy (e.g., benzyloxy, phenethyloxy, phenylpropyloxy, naphthylmethyloxy, naphthylethyloxy, etc.), phenoxy, C1-6 alkoxycarbonyl (e.g., tert-methoxycarbonyl, ethoxycarbonyl, butoxycarbonyl, etc.), C1-6 alkylcarbonyloxy (e.g., acetoxy, ethylcarbonyloxy, etc.), C1-4 alkylthio (e.g., methylthio, ethylthio, propylthio, butylthio, etc.), a halogen atom (a fluorine atom, a chlorine atom, a bromine atom, and an iodine atom), alkylsulfonyl (e.g., C1-4 alkylsulfonyl etc., such as methylsulfonyl, ethylsulfonyl, etc.), aromatic ring-sulfonyl (e.g., C6-10 aromatic ring sulfonyl etc., such as phenylsulfonyl etc.), acyl (e.g., C1-6 alkanoyl etc., such as formyl, acetyl, propanoyl, pivaloyl, etc., and C6-10 aromatic ring carbonyl etc., such as benzoyl etc.) etc. The C1-6 alkylidene may be substituted by 1 to 4 arbitrary substituent(s) in the replaceable position.

In the present specification, the C5-12 monocyclic or bicyclic carbocyclic ring includes a monocyclic or bicyclic C5-12 carbocyclic ring aryl or carbocyclic ring which is saturated either wholly or partially such as cyclopentane, cyclohexane, cycloheptane, cyclopentene, cyclohexene, cycloheptene, cyclopentadiene, cyclohexadiene, cycloheptadiene, benzene, pentalene, perhydropentalene, azulene, perhydroazulene, indene, perhydroindene, indane, naphthalene, dihydronaphthalene, tetrahydronaphthalene, and perhydronaphthalene.

In the present specification, the 5- to 12-membered monocyclic or bicyclic heterocycle includes a 5- to 12-membered monocyclic or bicyclic heterocyclic aryl containing hetero atom(s) selected from 1 to 4 nitrogen atom(s), one or two oxygen atom(s) and/or one or two sulfur atom(s) and the heterocycle that is saturated either wholly or partially. Such heterocycle includes, e.g., pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, oxazine, thiazine, indole, isoindole, benzofuran, isobenzofuran, benzothiophene, isobenzothiophene, dithianaphthalene, indazole, quinoline, isoquinoline, quinolidine, phthalazine, naphthylidine, quinoxaline, quinazoline, cinnoline, benzoxazole, benzothiazole, benzimidazole, chromene, benzoxepine, benzoxazepine, benzothiepine, benzothiazepine, benzoazepine, benzodiazepine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole(oxazolidine), dihydroisoxazole, tetrahydroisoxazole(isoxazolidine), dihydrothiazole, tetrahydrothiazole (thiazolidine), dihydroisothiazole, tetrahydroisothiazole (isothiazolidine), dihydrooxazine, tetrahydrooxazine, dihydrooxazepine, tetrahydrooxazepine, perhydrooxazepine, dihydrothiazine, tetrahydrothiazine, dihydrothiazepine, tetrahydrothiazepine, perhydrothiazepine, morpholine, thiomorpholine, oxathiane, dioxolane, dioxane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine; tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathian, dihydrobenzoxazine, dihydrobenzothiazine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepan, dihydrobenzoxazepine, and tetrahydrobenzoxazepine.

In the present specification, the C5-6 saturated carbocyclic ring includes cyclopentane and cyclohexane.

In the present specification, the 5- to 6-membered saturated heterocycle containing one or two nitrogen atom(s), one or two oxygen atom(s) and/or a sulfur atom includes, e.g., pyrrolidine, imidazolidine, pyrazolidine, piperidine, piperazine, perhydropyrimidine, perhydropyridazine, tetrahydrofuran, tetrahydropyran, tetrahydrothiophene, tetrahydrothiopyran, tetrahydrooxazole(oxazolidine), tetrahydroisoxazole(isoxazolidine), tetrahydrothiazole(thiazolidine), tetrahydroisothiazole(isothiazolidine), tetrahydrooxazine, tetrahydrothiazine, morpholine, thiomorpholine, oxathiane, dioxolane, dioxane, etc. In the present specification, the C5-6 carbocyclic ring includes, e.g., cyclopentane, cyclohexane, cyclopentene, cyclohexene, cyclopentadiene, cyclohexadiene, benzene, etc.

In the present specification, the 5- to 6-membered heterocycle containing one or two nitrogen atom(s), one or two oxygen atom(s) and/or a sulfur atom includes, e.g., pyrrole, imidazole, pyrazole, pyridine, pyrazine, pyrimidine, pyridazine, furan, pyran, thiophene, thiopyran, oxazole, isoxazole, thiazole, isothiazole, oxazine, thiazine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydroxazine, tetrahydroxazine, dihydrothiazine, tetrahydrothiazine, morpholine, thiomorpholine, oxathiane, dioxolane, dioxane, etc.

In the present specification, the substituent in the phenyl that may be substituted means the same as the substituent in the alkyl that may be substituted.

In the present specification, the sulfur atom that may be oxidized includes sulfone, sulfoxide, and sulfide.

Unless otherwise specifically mentioned, all isomers are included in the present specification. For example, linear and branched alkyl, alkenyl, alkynyl, alkoxy, alkylthio, alkylene, alkenylene, and alkynylene are included. Further, all of isomers due to double bond, ring and fused ring (E-, Z-, cis- and trans-substances), isomers due to presence of asymmetric carbon etc. (R-, S-, α- and β-substances, enantiomer, and diastereomer), optically active substances having optical rotation (D-, L-, d-, and l-substances), polar substances by chromatographic separation (high-polar substance and low-polar substance), equilibrium compounds, rotational isomers, a mixture thereof in any proportion and a racemic mixture are included in the present invention.

Unless otherwise specifically mentioned in the present specification, as will be obvious for persons skilled in the art, a symbol ⋯⋯ means a bond to the opposite side of the paper (i.e., α-configuration), ▰ means a bond to this side of the paper (i.e., β-configuration), ⁓ means α-configuration, β-configuration, or a mixture thereof, and ╱ means α-configuration or β-configuration.

The compounds represented by formula (I) are converted to salts by known methods. The salts include alkali metal salt, alkaline earth metal salt, ammonium salt, amine salt, acid addition salt, etc. The salts are preferably pharmaceutically acceptable.

The salts are preferably water-soluble. Appropriate salts are alkaline metal salt (potassium, sodium, etc.), alkaline earth metal salt (calcium, magnesium, etc.), ammonium salt, organic amine salt that is pharmaceutically acceptable (tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.).

The acid addition salts are preferably water-soluble. Appropriate acid addition salts include inorganic acid salts such as hydrochloride, hydrobromide, hydroiodide, sulfate, phosphate, and nitrate, and organic acid salt such as acetate, lactate, tartrate, oxalate, benzoate, citrate, methanesulfonate, ethanesulfonate, benzenesulfonate, toluenesulfonate, isothionate, glucuronate, and gluconate.

The compounds represented by formula (I) and salts thereof are converted to solvates.

The solvates are preferably non-toxic and water-soluble. Appropriate solvates include solvates such as water and alcoholic solvent (e.g., ethanol etc.).

The prodrug of the compound represented by formula (I) means a compound that is converted to the compound represented by formula (I) by reaction with enzymes, gastric acid etc in vivo. The prodrug of the compound represented by formula (I) include compounds in which the amino group was, e.g., acylated, alkylated, or phosphorylated (e.g., compounds in which the amino group of the compound represented by formula (I) was eicosanoylated, alanylated, pentylaminocarbonylated, (5-methyl-2-oxo-1,3-dioxolen-4-yl) methoxycarbonylated, tetrahydrofuranylated, pyrrolidyimethylated, pivaloyloxymethylated, acetoxymethylated, tert-butylated, etc.) when the compound represented by formula (I) has an amino group; compounds in which the hydroxyl group was, e.g., acylated, alkylated, phosphorylated or borated (e.g., compounds in which the hydroxyl group of the compound represented by formula (I) was acetylated, palmitoylated, propanoylated, pivaloylated, succinylated, fumarylated, alanylated, or dimethylaminomethylcarbonylated) when the compound represented by formula (I) has a hydroxyl group; the carboxyl group of the compound represented by formula (I) was, e.g., esterified or amidated (e.g., compounds in which the carboxyl group of the compound represented by formula (I) was made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide) when the compound represented by formula (I) has a carboxy group; compounds in which the carboxy group replaces with hydroxymethyl group. Those compounds may be produced by a known method per se. The prodrug of the compound represented by formula (I) may be either a hydrate or a non-hydrate.

$R^1$ in formula (I) is preferably a hydrogen atom, C1-4 alkyl or benzyl and, more preferably, a hydrogen atom or C1-4 alkyl.

$R^2$ in formula (I) is preferably a halogen atom, C1-6 alkyl, C1-6 alkoxy, hydroxyl, trihalomethyl, cyano, phenyl, pyridyl, nitro, or $NR^6R^7$ and more preferably a halogen atom, C1-6 alkyl, C1-6 alkoxy, or hydroxyl.

$R^3$ in formula (I) is preferably a halogen atom, C1-6 alkyl, C1-6 alkoxy, hydroxyl, trihalomethyl, or cyano, and more preferably a halogen atom, C1-6 alkyl, C1-6 alkoxy, or trihalomethyl.

$R^8$ in formula (I) is preferably C1-4 alkyl or phenyl.

$R^4$ in formula (I) is preferably a hydrogen atom, C1-4 alkyl or benzyl, and more preferably a hydrogen atom or C1-4 alkyl.

$R^5$ in formula (I) is preferably C1-6 alkyl, C1-10 alkoxy, a halogen atom, hydroxyl, trihalomethyl, phenyl or cyano, and more preferably C1-6 alkyl, C1-10 alkoxy, or a halogen atom.

$R^{12}$ in formula (I) is preferably C1-4 alkyl, a halogen atom, hydroxyl which may be protected, or a hydrogen atom, and more preferably C1-4 alkyl or a halogen hydrogen atom.

$R^{13}$ in formula (I) is preferably C1-4 alkyl, a hydrogen atom, hydroxyl which may be protected, or a hydrogen atom, and more preferably C1-4 alkyl or a halogen atom.

A group represented by a combination with $R^{12}$ and $R^{13}$ in formula (I) is preferably a group in which either is one except a hydrogen atom, and more preferably a group in which both are one except a hydrogen atom.

The group represented by the combination with $R^{12}$ and $R^{13}$ in formula (I) is preferably oxo or C2-5 alkylene in which one carbon atom may be replaced with an oxygen atom, a nitrogen atom, or a sulfur atom, and more preferably oxo, ethylene, or —(CH$_2$)$_2$—O—(CH$_2$)$_2$—.

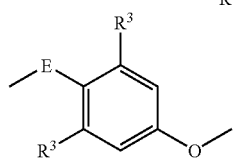

in formula (I) is preferably C5-6 monocyclic carbocyclic ring or 5- to 6-membered monocyclic heterocycle containing one or two nitrogen atom(s), one or two oxygen atom(s) and/or a sulfur atom such as cyclopentane, cyclohexane, benzene, pyrrole, imidazole, pyrazole, pyridine, pyrazine, pyrimidine, pyridazine, furan, pyran, thiophene, thiopyran, oxazole, isoxazole, thiazole, isothiazole, pyrrolidine, imidazolidine, piperidine, or piperazine ring, and is more preferably benzene or pyridine ring.

It is furthermore preferably C5-6 monocyclic carbocyclic ring such as benzenes represented by

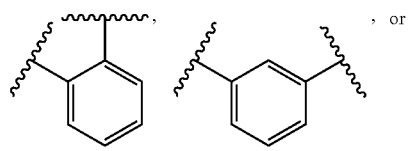

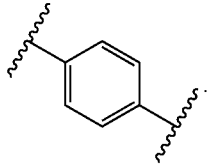

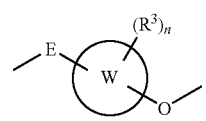

in formula (I) is preferably

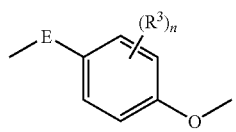

(in the formula, all symbols present the same meanings as the aforementioned) and is more preferably

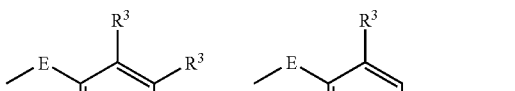

(in the formula, all symbols present the same meanings as the aforementioned, wherein two $R^3$'s may be same or different.)

G in formula (I) is preferably (1) C1-6 alkylene containing 0 to 2 hetero atom(s) selected from a nitrogen atom, an oxygen atom, and a sulfur atom, (2) C2-6 alkenylene or (3) C2-6 alkynylene and is more preferably (1) C1-6 alkylene containing 0 to 2 hetero atom(s) selected from a nitrogen atom, an oxygen atom, and a sulfur atom, (2) C2-4 alkenylene or (3) C2-4 alkynylene, and is furthermore preferably (1) C1-4 alkylene, (2) C2-4 alkenylene, or (3) C2-4 alkynylene.

in formula (I) is preferably (in the formula,

is C5-6 saturated carbocyclic ring or 5- to 6-membered saturated heterocycle containing one or two nitrogen atom(s), one or two oxygen atom(s) and/or a sulfur atom; and

is C5-6 carbocyclic ring or 5- to 6-membered heterocycle containing one or two nitrogen atom(s), one or two oxygen atom(s) and/or a sulfur atom.).

is preferably 5- to 6-membered saturated heterocycle containing one or two nitrogen atom(s), one or two oxygen atom(s) and/or a sulfur atom, and is more preferably 5- to 6-membered saturated heterocycle containing one or two nitrogen atom(s) and/or one or two oxygen atom(s). For example, it is preferably morpholine, dioxane, oxathiane, tetrahydrofuran, pyrrolidine, tetrahydrooxazole(oxazolidine), or imidazolidine and is more preferably morpholine, tetrahydrofuran, or pyrrolidine.

is preferably C5-6 carbocyclic ring or 5- to 6-membered heterocycle containing one or two nitrogen atom(s) and/or one or two oxygen atom(s), and more preferably a C5-6 carbocyclic ring or a 5- to 6-membered heterocycle containing one or two nitrogen atom(s). For example, it is preferably cyclopentane, cyclohexane, cyclopentadiene, benzene, pyridine, pyrazine, pyrimidine, pyridazine, oxazine, piperidine, or piperazine and is more preferably cyclohexane, benzene, pyridine, pyrazine, or pyrimidine ring, and is furthermore preferably benzene.

is preferably dihydrobenzoxazine, benzodioxane, benzoxathiane, dihydrobenzofuran, or indoline and more preferably dihydrobenzoxazine, dihydrobenzofuran, or indoline, and furthermore preferably dihydrobenzoxazine.

is preferably dihydrobenzoxazin-2-yl, benzodioxan-2-yl, benzoxathian-2-yl, dihydrobenzofuran-2-yl, dihydrobenzofuran-3-yl, benzodioxol-2-yl, indolin-2-yl, or indolin-3-yl, and is more preferably dihydrobenzoxazin-2-yl, dihydrobenzofuran-2-yl, dihydrobenzofuran-3-yl, indolin-2-yl, or indolin-3-yl, and is furthermore preferably dihydrobenzoxazin-2-yl.

Symbol "m" is preferably 0, 1, or 2.

Symbol "n" is preferably 2, 3, or 4, and is more preferably 2.

Symbol "i" is preferably 0 or an integer of 1 to 5.

With regard to the compound represented by formula (I), a preferred compound is a compound represented by formula (I-a)

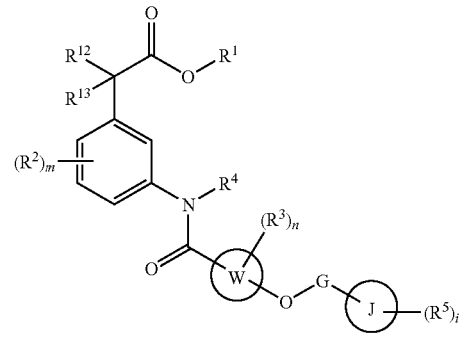

(I-a)

wherein all symbols have the same meanings as the aforementioned, a compound represented by formula (I-b)

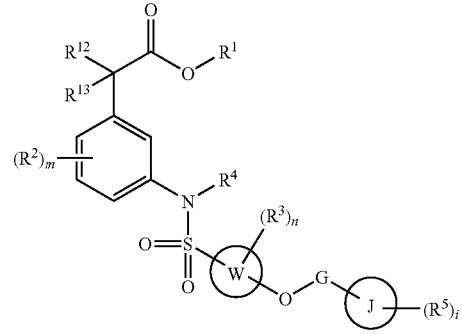

(I-b)

wherein all symbols have the same meanings as the aforementioned, or a compound represented by formula (I-c)

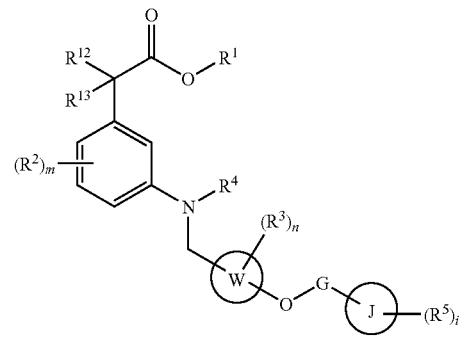

(I-c)

wherein all symbols have the same meanings as the aforementioned.

As concrete compounds, the present invention includes
(3-((2,5-dimethyl-4-(((2S)-4-methyl-3,4-dihydro-2H-1,4-benzoxazin-2-yl)methoxy)benzoyl)amino)phenyl)acetic acid,
(3-((2,6-dimethyl-4-(((2S)-4-methyl-3,4-dihydro-2H-1,4-benzoxazin-2-yl)methoxy)benzoyl)amino)phenyl)acetic acid,
(3-((2,3-dimethyl-4-(((2S)-4-methyl-3,4-dihydro-2H-1,4-benzoxazin-2-yl)methoxy)benzoyl)amino)phenyl)acetic acid,
(3-((2,5-dimethyl-4-(((2S)-4-methyl-3,4-dihydro-2H-1,4-benzoxazin-2-yl)methoxy)benzoyl)amino)-4-fluorophenyl)acetic acid,
(3-((2,6-dimethyl-4-(((2S)-4-methyl-3,4-dihydro-2H-1,4-benzoxazin-2-yl)methoxy)benzoyl)amino)-4-fluorophenyl)acetic acid,
(3-((2,3-dimethyl-4-(((2S)-4-methyl-3,4-dihydro-2H-1,4-benzoxazin-2-yl)methoxy)benzoyl)amino)-4-fluorophenyl)acetic acid,
(4-chloro-3-((2,5-dimethyl-4-(((2S)-4-methyl-3,4-dihydro-2H-1,4-benzoxazin-2-yl)methoxy)benzoyl)amino)phenyl)acetic acid,
(4-chloro-3-((2,6-dimethyl-4-(((2S)-4-methyl-3,4-dihydro-2H-1,4-benzoxazin-2-yl)methoxy)benzoyl)amino)phenyl)acetic acid,
(4-chloro-3-((2,3-dimethyl-4-(((2S)-4-methyl-3,4-dihydro-2H-1,4-benzoxazin-2-yl)methoxy)benzoyl)amino)phenyl)acetic acid,
(3-((2,5-dimethyl-4-(((2S)-4-methyl-3,4-dihydro-2H-1,4-benzoxazin-2-yl)methoxy)benzoyl)amino)-4-methylphenyl)acetic acid,
(3-((2,6-dimethyl-4-(((2S)-4-methyl-3,4-dihydro-2H-1,4-benzoxazin-2-yl)methoxy)benzoyl)amino)-4-methylphenyl)acetic acid,
(3-((2,3-dimethyl-4-(((2S)-4-methyl-3,4-dihydro-2H-1,4-benzoxazin-2-yl)methoxy)benzoyl)amino)-4-methylphenyl)acetic acid,
(3-((2,5-dimethyl-4-(((2S)-4-methyl-3,4-dihydro-2H-1,4-benzoxazin-2-yl)methoxy)benzoyl)amino)-5-methylphenyl)acetic acid,
(3-((2,6-dimethyl-4-(((2S)-4-methyl-3,4-dihydro-2H-1,4-benzoxazin-2-yl)methoxy)benzoyl)amino)-5-methylphenyl)acetic acid,
(3-((2,3-dimethyl-4-(((2S)-4-methyl-3,4-dihydro-2H-1,4-benzoxazin-2-yl)methoxy)benzoyl)amino)-5-methylphenyl)acetic acid,
(5-((2,5-dimethyl-4-(((2S)-4-methyl-3,4-dihydro-2H-1,4-benzoxazin-2-yl)methoxy)benzoyl)amino)-2-fluorophenyl)acetic acid,
(5-((2,6-dimethyl-4-(((2S)-4-methyl-3,4-dihydro-2H-1,4-benzoxazin-2-yl)methoxy)benzoyl)amino)-2-fluorophenyl)acetic acid,
(5-((2,3-dimethyl-4-(((2S)-4-methyl-3,4-dihydro-2H-1,4-benzoxazin-2-yl)methoxy)benzoyl)amino)-2-fluorophenyl)acetic acid,
(2-chloro-5-((2,5-dimethyl-4-(((2S)-4-methyl-3,4-dihydro-2H-1,4-benzoxazin-2-yl)methoxy)benzoyl)amino)phenyl)acetic acid,
(2-chloro-5-((2,6-dimethyl-4-(((2S)-4-methyl-3,4-dihydro-2H-1,4-benzoxazin-2-yl)methoxy)benzoyl)amino)phenyl)acetic acid,
(2-chloro-5-((2,3-dimethyl-4-(((2S)-4-methyl-3,4-dihydro-2H-1,4-benzoxazin-2-yl)methoxy)benzoyl)amino)phenyl)acetic acid,
(5-((2,5-dimethyl-4-(((2S)-4-methyl-3,4-dihydro-2H-1,4-benzoxazin-2-yl)methoxy)benzoyl)amino)-2-methylphenyl)acetic acid,
(5-((2,6-dimethyl-4-(((2S)-4-methyl-3,4-dihydro-2H-1,4-benzoxazin-2-yl)methoxy)benzoyl)amino)-2-methylphenyl)acetic acid,
(5-((2,3-dimethyl-4-(((2S)-4-methyl-3,4-dihydro-2H-1,4-benzoxazin-2-yl)methoxy)benzoyl)amino)-2-methylphenyl)acetic acid,
2-(4-chloro-3-((2-chloro-4-(((2S)-4-methyl-3,4-dihydro-2H-1,4-benzoxazin-2-yl)methoxy)benzoyl)amino)phenyl)-2-methylpropanoic acid,
(4-chloro-3-((2-chloro-4-(((2S)-4-methyl-3,4-dihydro-2H-1,4-benzoxazin-2-yl)methoxy)benzoyl)amino)phenyl)(difluoro)acetic acid,
(4-chloro-3-((2-chloro-4-(((2S)-4-methyl-3,4-dihydro-2H-1,4-benzoxazin-2-yl)methoxy)benzoyl)amino)phenyl)(oxo)acetic acid,
(4-chloro-3-((5-chloro-2-fluoro-4-(((2S)-4-methyl-3,4-dihydro-2H-1,4-benzoxazin-2-yl)methoxy)benzoyl)amino)phenyl)acetic acid,
(4-chloro-3-((2-fluoro-5-methyl-4-(((2S)-4-methyl-3,4-dihydro-2H-1,4-benzoxazin-2-yl)methoxy)benzoyl)amino)phenyl)acetic acid,
(4-chloro-3-((2,5-difluoro-4-(((2S)-4-methyl-3,4-dihydro-2H-1,4-benzoxazin-2-yl)methoxy)benzoyl)amino)phenyl)acetic acid,
(4-chloro-3-((4-((2R)-2,3-dihydro-1,4-benzodioxin-2-ylmethoxy)-2,6-dimethylbenzoyl)amino)phenyl)acetic acid,
(4-chloro-3-((4-((3R)-2,3-dihydro-1-benzofuran-3-ylmethoxy)-2,6-dimethylbenzoyl)amino)phenyl)acetic acid,
(4-chloro-3-((2,6-dimethyl-4-(((3R)-5-methyl-2,3-dihydro-1-benzofuran-3-yl)methoxy)benzoyl)amino)phenyl)acetic acid,
(4-chloro-3-((4-((2S)-2,3-dihydro-1-benzofuran-2-ylmethoxy)-2,6-dimethylbenzoyl)amino)phenyl)acetic acid,
(3-((4-(1,3-benzodioxol-2-ylmethoxy)-2,6-dimethylbenzoyl)amino)-4-chlorophenyl)acetic acid,
(3-((4-(((2S)-4,6-dimethyl-3,4-dihydro-2H-1,4-benzoxazin-2-yl)methoxy)-2,6-difluorobenzoyl)amino)-4-fluorophenyl)acetic acid,
(3-((2,5-difluoro-4-(((2S)-6-fluoro-4-methyl-3,4-dihydro-2H-1,4-benzoxazin-2-yl)methoxy)benzoyl)amino)-5-fluorophenyl)acetic acid,
(5-((4-(((2S)-6-chloro-4-methyl-3,4-dihydro-2H-1,4-benzoxazin-2-yl)methoxy)-2,3-difluorobenzoyl)amino)-2-fluorophenyl)acetic acid,
(4-chloro-3-((2,6-dichloro-4-(((2S)-6-methoxy-4-methyl-3,4-dihydro-2H-1,4-benzoxazin-2-yl)methoxy)benzoyl)amino)phenyl)acetic acid,
(3-chloro-5-((2,5-dichloro-4-(((2S)-4,7-dimethyl-3,4-dihydro-2H-1,4-benzoxazin-2-yl)methoxy)benzoyl)amino)phenyl)acetic acid,
(2-chloro-5-((2,3-dichloro-4-(((2S)-7-fluoro-4-methyl-3,4-dihydro-2H-1,4-benzoxazin-2-yl)methoxy)benzoyl)amino)phenyl)acetic acid,
(3-((4-(((2S)-7-chloro-4-methyl-3,4-dihydro-2H-1,4-benzoxazin-2-yl)methoxy)-2-fluoro-6-methylbenzoyl)amino)-4-methylphenyl)acetic acid,
(3-((2-fluoro-4-(((2S)-7-methoxy-4-methyl-3,4-dihydro-2H-1,4-benzoxazin-2-yl)methoxy)-5-methylbenzoyl)amino)-5-methylphenyl)acetic acid, (5-((2-fluoro-3-methyl-4-(((2S)-4-methyl-3,4-dihydro-2H-1,4-benzoxazin-2-yl)methoxy)benzoyl)amino)-2-methylphenyl)acetic acid,
(3-((4-(((2S)-4,6-dimethyl-3,4-dihydro-2H-1,4-benzoxazin-2-yl)methoxy)-5-fluoro-2-methylbenzoyl)amino)-4-fluorophenyl)acetic acid,
(3-fluoro-5-((3-fluoro-4-(((2S)-6-fluoro-4-methyl-3,4-dihydro-2H-1,4-benzoxazin-2-yl)methoxy)-2-methylbenzoyl)amino)phenyl)acetic acid,
(5-((2-chloro-4-(((2S)-6-chloro-4-methyl-3,4-dihydro-2H-1,4-benzoxazin-2-yl)methoxy)-6-methylbenzoyl)amino)-2-fluorophenyl)acetic acid,
(4-chloro-3-((2-chloro-4-(((2S)-6-methoxy-4-methyl-3,4-dihydro-2H-1,4-benzoxazin-2-yl)methoxy)-5-methylbenzoyl)amino)phenyl)acetic acid,
(3-chloro-5-((2-chloro-4-(((2S)-4,7-dimethyl-3,4-dihydro-2H-1,4-benzoxazin-2-yl)methoxy)-3-methylbenzoyl)amino)phenyl)acetic acid,
(2-chloro-5-((5-chloro-4-(((2S)-7-fluoro-4-methyl-3,4-dihydro-2H-1,4-benzoxazin-2-yl)methoxy)-2-methylbenzoyl)amino)phenyl)acetic acid,
(3-((3-chloro-4-(((2S)-7-chloro-4-methyl-3,4-dihydro-2H-1,4-benzoxazin-2-yl)methoxy)-2-methylbenzoyl)amino)-4-methylphenyl)acetic acid,
(3-((2-chloro-6-fluoro-4-(((2S)-7-methoxy-4-methyl-3,4-dihydro-2H-1,4-benzoxazin-2-yl)methoxy)benzoyl)amino)-5-methylphenyl)acetic acid,
(5-((2-chloro-4-((2S)-2,3-dihydro-1,4-benzodioxin-2-ylmethoxy)-5-fluorobenzoyl)amino)-2-methylphenyl)acetic acid,
(3-((2-chloro-3-fluoro-4-(((2S)-6-methyl-2,3-dihydro-1,4-benzodioxin-2-yl)methoxy)benzoyl)amino)-4-fluorophenyl)acetic acid,
(3-((5-chloro-2-fluoro-4-(((2S)-6-fluoro-2,3-dihydro-1,4-benzodioxin-2-yl)methoxy)benzoyl)amino)-5-fluorophenyl)acetic acid,
(5-((3-chloro-4-(((2S)-6-chloro-2,3-dihydro-1,4-benzodioxin-2-yl)methoxy)-2-fluorobenzoyl)amino)-2-fluorophenyl)acetic acid,
(4-chloro-3-((4-(((2R)-6-methoxy-2,3-dihydro-1,4-benzodioxin-2-yl)methoxy)-2,6-dimethylbenzoyl)amino)phenyl)acetic acid,
(3-chloro-5-((2,5-dimethyl-4-(((2R)-7-methyl-2,3-dihydro-1,4-benzodioxin-2-yl)methoxy)benzoyl)amino)phenyl)acetic acid,
(2-chloro-5-((4-(((2R)-7-fluoro-2,3-dihydro-1,4-benzodioxin-2-yl)methoxy)-2,3-dimethylbenzoyl)amino)phenyl)acetic acid,
(3-((4-(((2R)-7-chloro-2,3-dihydro-1,4-benzodioxin-2-yl)methoxy)-2,6-dimethylbenzoyl)amino)-4-methylphenyl)acetic acid,
(3-((4-(((2R)-7-methoxy-2,3-dihydro-1,4-benzodioxin-2-yl)methoxy)-2,5-dimethylbenzoyl)amino)-5-methylphenyl)acetic acid,
(5-((4-(((2R)-1-ethyl-2,3-dihydro-1H-indol-2-yl)methoxy)-2,6-dimethylbenzoyl)amino)-2-methylphenyl)acetic acid,
(3-((4-(((2R)-1-ethyl-5-fluoro-2,3-dihydro-1H-indol-2-yl)methoxy)-2,6-dimethylbenzoyl)amino)-4-fluorophenyl)acetic acid,
(3-((4-(((2R)-5-chloro-1-ethyl-2,3-dihydro-1H-indol-2-yl)methoxy)-2,5-dimethylbenzoyl)amino)-5-fluorophenyl)acetic acid,
(5-((4-(((2R)-1-ethyl-5-methyl-2,3-dihydro-1H-indol-2-yl)methoxy)-2,3-dimethylbenzoyl)amino)-2-fluorophenyl)acetic acid,
(4-chloro-3-((4-(((2S)-5-fluoro-2,3-dihydro-1-benzofuran-2-yl)methoxy)-2,6-dimethylbenzoyl)amino)phenyl)acetic acid,
(3-chloro-5-((4-(((2S)-5-chloro-2,3-dihydro-1-benzofuran-2-yl)methoxy)-2,5-dimethylbenzoyl)amino)phenyl)acetic acid,
(2-chloro-5-((2,3-dimethyl-4-(((2S)-5-methyl-2,3-dihydro-1-benzofuran-2-yl)methoxy)benzoyl)amino)phenyl)acetic acid,
(3-((4-((3S)-2,3-dihydro-1-benzofuran-3-ylmethoxy)-2,6-dimethylbenzoyl)amino)-4-methylphenyl)acetic acid,
(3-((4-((2R)-2,3-dihydro-1,4-benzodioxin-2-ylmethoxy)-2,6-dimethylbenzoyl)amino)-4-fluorophenyl)acetic acid,
(3-((4-((2R)-2,3-dihydro-1,4-benzodioxin-2-ylmethoxy)-2,6-dimethylbenzoyl)amino)-5-fluorophenyl)acetic acid,
(5-((4-((2R)-2,3-dihydro-1,4-benzodioxin-2-ylmethoxy)-2,6-dimethylbenzoyl)amino)-2-fluorophenyl)acetic acid,
(3-chloro-5-((4-((2R)-2,3-dihydro-1,4-benzodioxin-2-ylmethoxy)-2,6-dimethylbenzoyl)amino)phenyl)acetic acid, (2-chloro-5-((4-((2R)-2,3-dihydro-1,4-benzodioxin-2-ylmethoxy)-2,6-dimethylbenzoyl)amino)phenyl)acetic acid,
(3-((4-((2R)-2,3-dihydro-1,4-benzodioxin-2-ylmethoxy)-2,6-dimethylbenzoyl)amino)-4-methylphenyl)acetic acid,
(3-((4-((2R)-2,3-dihydro-1,4-benzodioxin-2-ylmethoxy)-2,6-dimethylbenzoyl)amino)-5-methylphenyl)acetic acid,
(5-((4-((2R)-2,3-dihydro-1,4-benzodioxin-2-ylmethoxy)-2,6-dimethylbenzoyl)amino)-2-methylphenyl)acetic acid,
(3-((4-((2R)-2,3-dihydro-1,4-benzodioxin-2-ylmethoxy)-2,6-dimethylbenzoyl)amino)phenyl)acetic acid,
2-(4-fluoro-3-((2-methyl-4-(((2S)-4-methyl-3,4-dihydro-2H-1,4-benzoxazin-2-yl)methoxy)benzoyl)amino)phenyl)-2-methylpropanoic acid,
2-(4-fluoro-3-((2-fluoro-4-(((2S)-4-methyl-3,4-dihydro-2H-1,4-benzoxazin-2-yl)methoxy)benzoyl)amino)phenyl)-2-methylpropanoic acid,
2-(3-((2-chloro-4-(((2S)-4-methyl-3,4-dihydro-2H-1,4-benzoxazin-2-yl)methoxy)benzoyl)amino)-4-fluorophenyl)-2-methylpropanoic acid,
2-(4-fluoro-3-((4-(((2S)-4-methyl-3,4-dihydro-2H-1,4-benzoxazin-2-yl)methoxy)benzoyl)amino)phenyl)-2-methylpropanoic acid,
2-(3-((2,5-dimethyl-4-(((2S)-4-methyl-3,4-dihydro-2H-1,4-benzoxazin-2-yl)methoxy)benzoyl)amino)-4-fluorophenyl)-2-methylpropanoic acid,
2-(3-((2,6-dimethyl-4-(((2S)-4-methyl-3,4-dihydro-2H-1,4-benzoxazin-2-yl)methoxy)benzoyl)amino)-4-fluorophenyl)-2-methylpropanoic acid,
2-(3-((2,3-dimethyl-4-(((2S)-4-methyl-3,4-dihydro-2H-1,4-benzoxazin-2-yl)methoxy)benzoyl)amino)-4-fluorophenyl)-2-methylpropanoic acid,
2-(4-chloro-3-((2,3-dimethyl-4-(((2S)-4-methyl-3,4-dihydro-2H-1,4-benzoxazin-2-yl)methoxy)benzoyl)amino)phenyl)-2-methylpropanoic acid,
2-(4-chloro-3-((2-methyl-4-(((2S)-4-methyl-3,4-dihydro-2H-1,4-benzoxazin-2-yl)methoxy)benzoyl)amino)phenyl)-2-methylpropanoic acid,
2-(4-chloro-3-((2-fluoro-4-(((2S)-4-methyl-3,4-dihydro-2H-1,4-benzoxazin-2-yl)methoxy)benzoyl)amino)phenyl)-2-methylpropanoic acid,
2-(4-chloro-3-((4-(((2S)-4-methyl-3,4-dihydro-2H-1,4-benzoxazin-2-yl)methoxy)benzoyl)amino)phenyl)-2-methylpropanoic acid,
2-(4-chloro-3-((2,5-dimethyl-4-(((2S)-4-methyl-3,4-dihydro-2H-1,4-benzoxazin-2-yl)methoxy)benzoyl)amino)phenyl)-2-methylpropanoic acid, 2-(4-chloro-3-((2,6-dimethyl-4-(((2S)-4-methyl-3,4-dihydro-2H-1,4-benzoxazin-2-yl)methoxy)benzoyl)amino)phenyl)-2-methylpropanoic acid, 2-methyl-2-(4-methyl-3-(2-methyl-4-(((2S)-4-methyl-3,4-dihydro-2H-1,4-benzoxazin-2-yl)methoxy)benzoyl)amino)phenyl)propanoic acid, 2-(3-((2-fluoro-4-(((2S)-4-methyl-3,4-dihydro-2H-1,4-benzoxazin-2-yl)methoxy)benzoyl)amino)-4-methylphenyl)-2-methylpropanoic acid, 2-(3-((2-chloro-4-(((2S)-4-methyl-3,4-dihydro-2H-1,4-benzoxazin-2-yl)methoxy)benzoyl)amino)-4-methylphenyl)-2-methylpropanoic acid, 2-methyl-2-(4-methyl-3-((4-(((2S)-4-methyl-3,4-dihydro-2H-1,4-benzoxazin-2-yl)methoxy)benzoyl)amino)phenyl)propanoic acid, 2-(3-((2,5-dimethyl-4-(((2S)-4-methyl-3,4-dihydro-2H-1,4-benzoxazin-2-yl)methoxy)benzoyl)amino)-4-methylphenyl)-2-methylpropanoic acid, 2-(3-((2,6-dimethyl-4-(((2S)-4-methyl-3,4-dihydro-2H-1,4-benzoxazin-2-yl)methoxy)benzoyl)amino)-4-methylphenyl)-2-methylpropanoic acid, 2-(3-((2,3-dimethyl-4-(((2S)-4-methyl-3,4-dihydro-2H-1,4-benzoxazin-2-yl)methoxy)benzoyl)amino)-4-methylphenyl)-2-methylpropanoic acid, 2-(3-((2,3-dimethyl-4-(((2S)-4-methyl-3,4-dihydro-2H-1,4-benzoxazin-2-yl)methoxy)benzoyl)amino)-5-methylphenyl)-2-methylpropanoic acid, 2-methyl-2-(3-methyl-5-((2-methyl-4-(((2S)-4-methyl-3,4-dihydro-2H-1,4-benzoxazin-2-yl)methoxy)benzoyl)amino)phenyl)propanoic acid, 2-(3-((2-fluoro-4-(((2S)-4-methyl-3,4-dihydro-2H-1,4-benzoxazin-2-yl)methoxy)benzoyl)amino)-5-methylphenyl)-2-methylpropanoic acid, 2-(3-((2-chloro-4-(((2S)-4-methyl-3,4-dihydro-2H-1,4-benzoxazin-2-yl)methoxy)benzoyl)amino)-5-methylphenyl)-2-methylpropanoic acid, 2-methyl-2-(3-methyl-5-((4-(((2S)-4-methyl-3,4-dihydro-2H-1,4-benzoxazin-2-yl)methoxy)benzoyl)amino)phenyl)propanoic acid, 2-(3-((2,5-dimethyl-4-(((2S)-4-methyl-3,4-dihydro-2H-1,4-benzoxazin-2-yl)methoxy)benzoyl)amino)-5-methylphenyl)-2-methylpropanoic acid, 2-(3-((2,6-dimethyl-4-(((2S)-4-methyl-3,4-dihydro-2H-1,4-benzoxazin-2-yl)methoxy)benzoyl)amino)-5-methylphenyl)-2-methylpropanoic acid, 2-(3-fluoro-5-((2-methyl-4-(((2S)-4-methyl-3,4-dihydro-2H-1,4-benzoxazin-2-yl)methoxy)benzoyl)amino)phenyl)-2-methylpropanoic acid, 2-(3-fluoro-5-((2-fluoro-4-(((2S)-4-methyl-3,4-dihydro-2H-1,4-benzoxazin-2-yl)methoxy)benzoyl)amino)phenyl)-2-methylpropanoic acid, 2-(3-((2-chloro-4-(((2S)-4-methyl-3,4-dihydro-2H-1,4-benzoxazin-2-yl)methoxy)benzoyl)amino)-5-fluorophenyl)-2-methylpropanoic acid, 2-(3-fluoro-5-((4-(((2S)-4-methyl-3,4-dihydro-2H-1,4-benzoxazin-2-yl)methoxy)benzoyl)amino)phenyl)-2-methylpropanoic acid, 2-(3-((2,5-dimethyl-4-(((2S)-4-methyl-3,4-dihydro-2H-1,4-benzoxazin-2-yl)methoxy)benzoyl)amino)-5-fluorophenyl)-2-methylpropanoic acid, 2-(3-((2,6-dimethyl-4-(((2S)-4-methyl-3,4-dihydro-2H-1,4-benzoxazin-2-yl)methoxy)benzoyl)amino)-5-fluorophenyl)-2-methylpropanoic acid, 2-(3-((2,3-dimethyl-4-(((2S)-4-methyl-3,4-dihydro-2H-1,4-benzoxazin-2-yl)methoxy)benzoyl)amino)-5-fluorophenyl)-2-methylpropanoic acid, 2-(3-chloro-5-((2,3-dimethyl-4-(((2S)-4-methyl-3,4-dihydro-2H-1,4-benzoxazin-2-yl)methoxy)benzoyl)amino)phenyl)-2-methylpropanoic acid, 2-(3-chloro-5-((2-methyl-4-(((2S)-4-methyl-3,4-dihydro-2H-1,4-benzoxazin-2-yl)methoxy)benzoyl)amino)phenyl)-2-methylpropanoic acid, 2-(3-chloro-5-((2-fluoro-4-(((2S)-4-methyl-3,4-dihydro-2H-1,4-benzoxazin-2-yl)methoxy)benzoyl)amino)phenyl)-2-methylpropanoic acid, 2-(3-chloro-5-((2-chloro-4-(((2S)-4-methyl-3,4-dihydro-2H-1,4-benzoxazin-2-yl)methoxy)benzoyl)amino)phenyl)-2-methylpropanoic acid, 2-(3-chloro-5-((4-(((2S)-4-methyl-3,4-dihydro-2H-1,4-benzoxazin-2-yl)methoxy)benzoyl)amino)phenyl)-2-methylpropanoic acid, 2-(3-chloro-5-((2,5-dimethyl-4-(((2S)-4-methyl-3,4-dihydro-2H-1,4-benzoxazin-2-yl)methoxy)benzoyl)amino)phenyl)-2-methylpropanoic acid, 2-(3-chloro-5-((2,6-dimethyl-4-(((2S)-4-methyl-3,4-dihydro-2H-1,4-benzoxazin-2-yl)methoxy)benzoyl)amino)phenyl)-2-methylpropanoic acid, 2-methyl-2-(2-methyl-5-(2-methyl-4-(((2S)-4-methyl-3,4-dihydro-2H-1,4-benzoxazin-2-yl)methoxy)benzoyl)amino)phenyl)propanoic acid, 2-(5-((2-fluoro-4-(((2S)-4-methyl-3,4-dihydro-2H-1,4-benzoxazin-2-yl)methoxy)benzoyl)amino)-2-methylphenyl)-2-methylpropanoic acid, 2-(5-((2-chloro-4-(((2S)-4-methyl-3,4-dihydro-2H-1,4-benzoxazin-2-yl)methoxy)benzoyl)amino)-2-methylphenyl)-2-methylpropanoic acid, 2-methyl-2-(2-methyl-5-((4-(((2S)-4-methyl-3,4-dihydro-2H-1,4-benzoxazin-2-yl)methoxy)benzoyl)amino)phenyl)propanoic acid, 2-(5-((2,5-dimethyl-4-(((2S)-4-methyl-3,4-dihydro-2H-1,4-benzoxazin-2-yl)methoxy)benzoyl)amino)-2-methylphenyl)-2-methylpropanoic acid, 2-(5-((2,6-dimethyl-4-(((2S)-4-methyl-3,4-dihydro-2H-1,4-benzoxazin-2-yl)methoxy)benzoyl)amino)-2-methylphenyl)-2-methylpropanoic acid, 2-(5-((2,3-dimethyl-4-(((2S)-4-methyl-3,4-dihydro-2H-1,4-benzoxazin-2-yl)methoxy)benzoyl)amino)-2-methylphenyl)-2-methylpropanoic acid, 2-(5-((2,3-dimethyl-4-(((2S)-4-methyl-3,4-dihydro-2H-1,4-benzoxazin-2-yl)methoxy)benzoyl)amino)-2-fluorophenyl)-2-methylpropanoic acid, 2-(2-fluoro-5-((2-methyl-4-(((2S)-4-methyl-3,4-dihydro-2H-1,4-benzoxazin-2-yl)methoxy)benzoyl)amino)phenyl)-2-methylpropanoic acid, 2-(2-fluoro-5-((2-fluoro-4-(((2S)-4-methyl-3,4-dihydro-2H-1,4-benzoxazin-2-yl)methoxy)benzoyl)amino)phenyl)-2-methylpropanoic acid, 2-(5-((2-chloro-4-(((2S)-4-methyl-3,4-dihydro-2H-1,4-benzoxazin-2-yl)methoxy)benzoyl)amino)-2-fluorophenyl)-2-methylpropanoic acid, 2-(2-fluoro-5-((4-(((2S)-4-methyl-3,4-dihydro-2H-1,4-benzoxazin-2-yl)methoxy)benzoyl)amino)phenyl)-2-methylpropanoic acid, 2-(5-((2,5-dimethyl-4-(((2S)-4-methyl-3,4-dihydro-2H-1,4-benzoxazin-2-yl)methoxy)benzoyl)amino)-2-fluorophenyl)-2-methylpropanoic acid, 2-(5-((2,6-dimethyl-4-(((2S)-4-methyl-3,4-dihydro-2H-1,4-benzoxazin-2-yl)methoxy)benzoyl)amino)-2-fluorophenyl)-2-methylpropanoic acid, 2-(2-chloro-5-(2-methyl-4-(((2S)-4-methyl-3,4-dihydro-2H-1,4-benzoxazin-2-yl)methoxy)benzoyl)amino)phenyl)-2-methylpropanoic acid, 2-(2-chloro-5-((2-fluoro-4-(((2S)-4-methyl-3,4-dihydro-2H-1,4-benzoxazin-2-yl)methoxy)benzoyl)amino)phenyl)-2-methylpropanoic acid,
2-(2-chloro-5-((2-chloro-4-(((2S)-4-methyl-3,4-dihydro-2H-1,4-benzoxazin-2-yl)methoxy)benzoyl)amino)phenyl)-2-methylpropanoic acid,
2-(2-chloro-5-((4-(((2S)-4-methyl-3,4-dihydro-2H-1,4-benzoxazin-2-yl)methoxy)benzoyl)amino)phenyl)-2-methylpropanoic acid,
2-(2-chloro-5-((2,5-dimethyl-4-(((2S)-4-methyl-3,4-dihydro-2H-1,4-benzoxazin-2-yl)methoxy)benzoyl)amino)phenyl)-2-methylpropanoic acid,
2-(2-chloro-5-((2,6-dimethyl-4-(((2S)-4-methyl-3,4-dihydro-2H-1,4-benzoxazin-2-yl)methoxy)benzoyl)amino)phenyl)-2-methylpropanoic acid,
2-(2-chloro-5-((2,3-dimethyl-4-(((2S)-4-methyl-3,4-dihydro-2H-1,4-benzoxazin-2-yl)methoxy)benzoyl)amino)phenyl)-2-methylpropanoic acid,
2-(3-((2,3-dimethyl-4-(((2S)-4-methyl-3,4-dihydro-2H-1,4-benzoxazin-2-yl)methoxy)benzoyl)amino)phenyl)-2-methylpropanoic acid,
2-methyl-2-(3-((2-methyl-4-(((2S)-4-methyl-3,4-dihydro-2H-1,4-benzoxazin-2-yl)methoxy)benzoyl)amino)phenyl)propanoic acid,
2-(3-((2-fluoro-4-(((2S)-4-methyl-3,4-dihydro-2H-1,4-benzoxazin-2-yl)methoxy)benzoyl)amino)phenyl)-2-methylpropanoic acid,
2-(3-((2-chloro-4-(((2S)-4-methyl-3,4-dihydro-2H-1,4-benzoxazin-2-yl)methoxy)benzoyl)amino)phenyl)-2-methylpropanoic acid,
2-methyl-2-(3-((4-(((2S)-4-methyl-3,4-dihydro-2H-1,4-benzoxazin-2-yl)methoxy)benzoyl)amino)phenyl)propanoic acid,
2-(3-((2,5-dimethyl-4-(((2S)-4-methyl-3,4-dihydro-2H-1,4-benzoxazin-2-yl)methoxy)benzoyl)amino)phenyl)-2-methylpropanoic acid,
2-(3-((2,6-dimethyl-4-(((2S)-4-methyl-3,4-dihydro-2H-1,4-benzoxazin-2-yl)methoxy)benzoyl)amino)phenyl)-2-methylpropanoic acid,
2-(3-((3-chloro-2-fluoro-4-(((2S)-7-methoxy-4-methyl-3,4-dihydro-2H-1,4-benzoxazin-2-yl)methoxy)benzoyl)amino)-4-fluorophenyl)-2-methylpropanoic acid,
2-(3-((5-chloro-4-(((2S)-7-chloro-4-methyl-3,4-dihydro-2H-1,4-benzoxazin-2-yl)methoxy)-2-fluorobenzoyl)amino)-5-fluorophenyl)-2-methylpropanoic acid,
2-(5-((2-chloro-3-fluoro-4-(((2S)-7-fluoro-4-methyl-3,4-dihydro-2H-1,4-benzoxazin-2-yl)methoxy)benzoyl)amino)-2-fluorophenyl)-2-methylpropanoic acid,
2-(4-chloro-3-((2-chloro-4-(((2S)-4,7-dimethyl-3,4-dihydro-2H-1,4-benzoxazin-2-yl)methoxy)-5-fluorobenzoyl)amino)phenyl)-2-methylpropanoic acid,
2-(3-chloro-5-((2-chloro-6-fluoro-4-(((2S)-6-methoxy-4-methyl-3,4-dihydro-2H-1,4-benzoxazin-2-yl)methoxy)benzoyl)amino)phenyl)-2-methylpropanoic acid,
2-(2-chloro-5-((3-chloro-4-(((2S)-6-chloro-4-methyl-3,4-dihydro-2H-1,4-benzoxazin-2-yl)methoxy)-2-methylbenzoyl)amino)phenyl)-2-methylpropanoic acid,
2-(3-((5-chloro-4-(((2S)-6-fluoro-4-methyl-3,4-dihydro-2H-1,4-benzoxazin-2-yl)methoxy)-2-methylbenzoyl)amino)-4-methylphenyl)-2-methylpropanoic acid,
2-(3-((2-chloro-4-(((2S)-4,6-dimethyl-3,4-dihydro-2H-1,4-benzoxazin-2-yl)methoxy)-3-methylbenzoyl)amino)-5-methylphenyl)-2-methylpropanoic acid,
2-(5-((2-chloro-5-methyl-4-(((2S)-4-methyl-3,4-dihydro-2H-1,4-benzoxazin-2-yl)methoxy)benzoyl)amino)-2-methylphenyl)-2-methylpropanoic acid,
2-(3-((2-chloro-4-(((2R)-7-methoxy-2,3-dihydro-1,4-benzodioxin-2-yl)methoxy)-6-methylbenzoyl)amino)-4-fluorophenyl)-2-methylpropanoic acid,
2-(3-((4-(((2S)-7-chloro-2,3-dihydro-1,4-benzodioxin-2-yl)methoxy)-3-fluoro-2-methylbenzoyl)amino)-5-fluorophenyl)-2-methylpropanoic acid,
2-(2-fluoro-5-((5-fluoro-4-(((2S)-7-fluoro-2,3-dihydro-1,4-benzodioxin-2-yl)methoxy)-2-methylbenzoyl)amino)phenyl)-2-methylpropanoic acid,
2-(3-fluoro-5-((2-fluoro-3-methyl-4-(((2R)-7-methyl-2,3-dihydro-1,4-benzodioxin-2-yl)methoxy)benzoyl)amino)phenyl)-2-methylpropanoic acid,
2-(4-fluoro-3-((2-fluoro-4-(((2R)-6-methoxy-2,3-dihydro-1,4-benzodioxin-2-yl)methoxy)-5-methylbenzoyl)amino)phenyl)-2-methylpropanoic acid,
2-(3-((4-(((2R)-6-chloro-2,3-dihydro-1,4-benzodioxin-2-yl)methoxy)-2-fluoro-6-methylbenzoyl)amino)-5-fluorophenyl)-2-methylpropanoic acid,
2-(5-((2,3-dichloro-4-(((2S)-6-fluoro-2,3-dihydro-1,4-benzodioxin-2-yl)methoxy)benzoyl)amino)-2-fluorophenyl)-2-methylpropanoic acid,
2-(3-((2,5-dichloro-4-(((2S)-6-methyl-2,3-dihydro-1,4-benzodioxin-2-yl)methoxy)benzoyl)amino)-5-fluorophenyl)-2-methylpropanoic acid,
2-(5-((2,6-dichloro-4-((2R)-2,3-dihydro-1,4-benzodioxin-2-ylmethoxy)benzoyl)amino)-2-fluorophenyl)-2-methylpropanoic acid,
2-(4-chloro-3-((4-(((2R)-1-ethyl-5-methyl-2,3-dihydro-1H-indol-2-yl)methoxy)-2,3-difluorobenzoyl)amino)phenyl)-2-methylpropanoic acid,
2-(3-chloro-5-((4-(((2R)-5-chloro-1-ethyl-2,3-dihydro-1H-indol-2-yl)methoxy)-2,5-difluorobenzoyl)amino)phenyl)-2-methylpropanoic acid,
2-(2-chloro-5-((4-(((2R)-1-ethyl-5-fluoro-2,3-dihydro-1H-indol-2-yl)methoxy)-2,6-difluorobenzoyl)amino)phenyl)-2-methylpropanoic acid,
2-(3-((4-(((2R)-1-ethyl-2,3-dihydro-1H-indol-2-yl)methoxy)-2,3-dimethylbenzoyl)amino)-4-methylphenyl)-2-methylpropanoic acid,
2-(3-((2,5-dimethyl-4-(((2S)-5-methyl-2,3-dihydro-1-benzofuran-2-yl)methoxy)benzoyl)amino)-5-methylphenyl)-2-methylpropanoic acid,
2-(5-((4-(((2S)-5-chloro-2,3-dihydro-1-benzofuran-2-yl)methoxy)-2,6-dimethylbenzoyl)amino)-2-methylphenyl)-2-methylpropanoic acid,
2-(4-fluoro-3-((2-fluoro-4-(((2S)-5-fluoro-2,3-dihydro-1-benzofuran-2-yl)methoxy)benzoyl)amino)phenyl)-2-methylpropanoic acid,
2-(4-chloro-3-((4-((2S)-2,3-dihydro-1-benzofuran-2-ylmethoxy)benzoyl)amino)phenyl)-2-methylpropanoic acid,
2-(3-((2-chloro-4-(((3S)-2,3-dihydro-1-benzofuran-3-yl)methoxy)benzoyl)amino)-4-methylphenyl)-2-methylpropanoic acid,
2-(5-((4-((2R)-2,3-dihydro-1,4-benzodioxin-2-ylmethoxy)-2,6-dimethylbenzoyl)amino)-2-fluorophenyl)-2-methylpropanoic acid,
2-(2-chloro-5-((4-(((2R)-1-ethyl-2,3-dihydro-1H-indol-2-yl)methoxy)-2,5-dimethylbenzoyl)amino)phenyl)-2-methylpropanoic acid,
2-(5-((4-((2R)-2,3-dihydro-1,4-benzodioxin-2-ylmethoxy)-2,3-dimethylbenzoyl)amino)-2-methylphenyl)-2-methylpropanoic acid,
(3-(((2,5-dimethyl-4-(((2S)-4-methyl-3,4-dihydro-2H-1,4-benzoxazin-2-yl)methoxy)phenyl)sulfonyl)amino)phenyl)acetic acid, (3-(((2,5-dimethyl-4-(((2S)-4-methyl-3,4-dihydro-2H-1,4-benzoxazin-2-yl)methoxy)phenyl)sulfonyl)(methyl)amino)phenyl)acetic acid,
(3-(((2,5-dimethyl-4-(((2S)-4-methyl-3,4-dihydro-2H-1,4-benzoxazin-2-yl)methoxy)phenyl)sulfonyl)(ethyl)amino)phenyl)acetic acid,
(3-(((2,5-dimethyl-4-(((2S)-4-methyl-3,4-dihydro-2H-1,4-benzoxazin-2-yl)methoxy)phenyl)sulfonyl)(isobutyl)amino)phenyl)acetic acid,
(3-chloro-5-(((4-(((2S)-4,7-dimethyl-3,4-dihydro-2H-1,4-benzoxazin-2-yl)methoxy)-2,3-dimethylphenyl)sulfonyl)amino)phenyl)acetic acid,
(2-chloro-5-(((4-(((2S)-7-fluoro-4-methyl-3,4-dihydro-2H-1,4-benzoxazin-2-yl)methoxy)-2,3-dimethylphenyl)sulfonyl)(methyl)amino)phenyl)acetic acid,
(3-(((4-(((2S)-7-chloro-4-methyl-3,4-dihydro-2H-1,4-benzoxazin-2-yl)methoxy)-2,3-dimethylphenyl)sulfonyl)(ethyl)amino)-4-methylphenyl)acetic acid,
(4-fluoro-3-((4-(((2S)-4-methyl-3,4-dihydro-2H-1,4-benzoxazin-2-yl)methoxy)benzoyl)amino)phenyl)(oxo)acetic acid,
(3-((4-(((2S)-4,6-dimethyl-3,4-dihydro-2H-1,4-benzoxazin-2-yl)methoxy)-2-fluorobenzoyl)amino)-5-fluorophenyl)(oxo)acetic acid,
(5-((2-chloro-4-(((2S)-6-fluoro-4-methyl-3,4-dihydro-2H-1,4-benzoxazin-2-yl)methoxy)benzoyl)amino)-2-fluorophenyl)(oxo)acetic acid,
(4-chloro-3-((4-(((2S)-6-chloro-4-methyl-3,4-dihydro-2H-1,4-benzoxazin-2-yl)methoxy)-2-methylbenzoyl)amino)phenyl)(oxo)acetic acid,
(3-chloro-5-((4-(((2S)-6-methoxy-4-methyl-3,4-dihydro-2H-1,4-benzoxazin-2-yl)methoxy)-2,6-dimethylbenzoyl)amino)phenyl)(oxo)acetic acid,
(2-chloro-5-((4-(((2S)-4,7-dimethyl-3,4-dihydro-2H-1,4-benzoxazin-2-yl)methoxy)-2,5-dimethylbenzoyl)amino)phenyl)(oxo)acetic acid,
(3-((4-(((2S)-7-fluoro-4-methyl-3,4-dihydro-2H-1,4-benzoxazin-2-yl)methoxy)-2,3-dimethylbenzoyl)amino)-4-methylphenyl)(oxo)acetic acid,
(3-((4-(((2S)-7-chloro-4-methyl-3,4-dihydro-2H-1,4-benzoxazin-2-yl)methoxy)-2,6-difluorobenzoyl)amino)-5-methylphenyl)(oxo)acetic acid,
(5-((2,5-dichloro-4-(((2S)-7-methoxy-4-methyl-3,4-dihydro-2H-1,4-benzoxazin-2-yl)methoxy)benzoyl)amino)-2-methylphenyl)(oxo)acetic acid,
(3-((4-((2R)-2,3-dihydro-1,4-benzodioxin-2-ylmethoxy)-2-fluoro-3-methylbenzoyl)amino)-4-fluorophenyl)(oxo)acetic acid,
(3-((5-chloro-4-(((2R)-1-ethyl-2,3-dihydro-1H-indol-2-yl)methoxy)-2-methylbenzoyl)amino)-5-fluorophenyl)(oxo)acetic acid,
(5-((3-chloro-4-((2S)-2,3-dihydro-1-benzofuran-2-ylmethoxy)-2-fluorobenzoyl)amino)-2-fluorophenyl)(oxo)acetic acid,
(3-((2-fluoro-6-methyl-4-(((2S)-4-methyl-3,4-dihydro-2H-1,4-benzoxazin-2-yl)methoxy)benzoyl)amino)phenyl)(oxo)acetic acid,
(3-((2-chloro-4-((2R)-2,3-dihydro-1,4-benzodioxin-2-yl)methoxy)-5-methylbenzoyl)amino)phenyl)(oxo)acetic acid,
(3-((2-chloro-4-(((2R)-1-ethyl-2,3-dihydro-1H-indol-2-yl)methoxy)-3-fluorobenzoyl)amino)phenyl)(oxo)acetic acid,
(4-chloro-3-((4-(((2S)-4-methyl-3,4-dihydro-2H-1,4-benzoxazin-2-yl)methoxy)benzoyl)amino)phenyl)(difluoro)acetic acid,
(3-chloro-5-((4-(((2S)-4,6-dimethyl-3,4-dihydro-2H-1,4-benzoxazin-2-yl)methoxy)-2-fluorobenzoyl)amino)phenyl)(difluoro)acetic acid,
(2-chloro-5-((2-chloro-4-(((2S)-6-fluoro-4-methyl-3,4-dihydro-2H-1,4-benzoxazin-2-yl)methoxy)benzoyl)amino)phenyl)(difluoro)acetic acid,
(3-((4-(((2S)-6-chloro-4-methyl-3,4-dihydro-2H-1,4-benzoxazin-2-yl)methoxy)-2-methylbenzoyl)amino)-4-methylphenyl)(difluoro)acetic acid,
difluoro(3-((4-(((2S)-6-methoxy-4-methyl-3,4-dihydro-2H-1,4-benzoxazin-2-yl)methoxy)-2,6-dimethylbenzoyl)amino)-5-methylphenyl)acetic acid,
(5-((4-(((2S)-4,7-dimethyl-3,4-dihydro-2H-1,4-benzoxazin-2-yl)methoxy)-2,5-dimethylbenzoyl)amino)-2-methylphenyl)(difluoro)acetic acid,
difluoro(4-fluoro-3-((4-(((2S)-7-fluoro-4-methyl-3,4-dihydro-2H-1,4-benzoxazin-2-yl)methoxy)-2,3-dimethylbenzoyl)amino)phenyl)acetic acid,
(3-((4-(((2S)-7-chloro-4-methyl-3,4-dihydro-2H-1,4-benzoxazin-2-yl)methoxy)-2,6-difluorobenzoyl)amino)-5-fluorophenyl)(difluoro)acetic acid,
(5-((2,5-dichloro-4-(((2S)-7-methoxy-4-methyl-3,4-dihydro-2H-1,4-benzoxazin-2-yl)methoxy)benzoyl)amino)-2-fluorophenyl)(difluoro)acetic acid,
(4-chloro-3-((4-((2R)-2,3-dihydro-1,4-benzodioxin-2-ylmethoxy)-2-fluoro-3-methylbenzoyl)amino)phenyl)(difluoro)acetic acid,
(3-chloro-5-((5-chloro-4-(((2R)-1-ethyl-2,3-dihydro-1H-indol-2-yl)methoxy)-2-methylbenzoyl)amino)phenyl)(difluoro)acetic acid,
(2-chloro-5-((3-chloro-4-((2S)-2,3-dihydro-1-benzofuran-2-ylmethoxy)-2-fluorobenzoyl)amino)phenyl)(difluoro)acetic acid,
difluoro(3-((2-fluoro-6-methyl-4-(((2S)-4-methyl-3,4-dihydro-2H-1,4-benzoxazin-2-yl)methoxy)benzoyl)amino)phenyl)acetic acid,
(3-((2-chloro-4-((2R)-2,3-dihydro-1,4-benzodioxin-2-ylmethoxy)-5-methylbenzoyl)amino)phenyl)(difluoro)acetic acid,
(3-((2-chloro-4-(((2R)-1-ethyl-2,3-dihydro-1H-indol-2-yl)methoxy)-3-fluorobenzoyl)amino)phenyl)(difluoro)acetic acid,
1-(3-((4-(((2S)-4,6-dimethyl-3,4-dihydro-2H-1,4-benzoxazin-2-yl)methoxy)-2,3-dimethylbenzoyl)amino)-4-fluorophenyl)cyclopropanecarboxylic acid,
1-(3-fluoro-5-((4-(((2S)-6-fluoro-4-methyl-3,4-dihydro-2H-1,4-benzoxazin-2-yl)methoxy)-2,5-dimethylbenzoyl)amino)phenyl)cyclopropanecarboxylic acid,
1-(5-((4-(((2S)-6-chloro-4-methyl-3,4-dihydro-2H-1,4-benzoxazin-2-yl)methoxy)-2,6-dimethylbenzoyl)amino)-2-fluorophenyl)cyclopropanecarboxylic acid,
1-(4-chloro-3-((4-(((2S)-6-methoxy-4-methyl-3,4-dihydro-2H-1,4-benzoxazin-2-yl)methoxy)-2-methylbenzoyl)amino)phenyl)cyclopropanecarboxylic acid,
1-(3-chloro-5-((2-chloro-4-(((2S)-4,7-dimethyl-3,4-dihydro-2H-1,4-benzoxazin-2-yl)methoxy)benzoyl)amino)phenyl)cyclopropanecarboxylic acid,
1-(2-chloro-5-((4-(((2S)-7-fluoro-4-methyl-3,4-dihydro-2H-1,4-benzoxazin-2-yl)methoxy)benzoyl)amino)phenyl)cyclopropanecarboxylic acid,
1-(3-((4-(((2S)-7-chloro-4-methyl-3,4-dihydro-2H-1,4-benzoxazin-2-yl)methoxy)-2-fluorobenzoyl)amino)-4-methylphenyl)cyclopropanecarboxylic acid,
1-(3-((2,6-dichloro-4-(((2S)-7-methoxy-4-methyl-3,4-dihydro-2H-1,4-benzoxazin-2-yl)methoxy)benzoyl)amino)-5-methylphenyl)cyclopropanecarboxylic acid, 1-(5-((4-((2R)-2,3-dihydro-1,4-benzodioxin-2-ylmethoxy)-2-fluoro-5-methylbenzoyl)amino)-2-methylphenyl)cyclopropanecarboxylic acid, 1-(3-((2-chloro-3-methyl-4-(((2S)-4-methyl-3,4-dihydro-2H-1,4-benzoxazin-2-yl)methoxy)benzoyl)amino)-4-fluorophenyl)cyclopropanecarboxylic acid, 1-(4-chloro-3-((5-chloro-4-(((2R)-1-ethyl-2,3-dihydro-1H-indol-2-yl)methoxy)-2-fluorobenzoyl)amino)phenyl)cyclopropanecarboxylic acid, 1-(3-((2-chloro-4-((2S)-2,3-dihydro-1-benzofuran-2-ylmethoxy)-6-methylbenzoyl)amino)-4-methylphenyl)cyclopropanecarboxylic acid, 1-(5-((2-chloro-4-((3R)-2,3-dihydro-1-benzofuran-3-ylmethoxy)-5-fluorobenzoyl)amino)-2-fluorophenyl)cyclopropanecarboxylic acid, 1-(2-chloro-5-((5-fluoro-2-methyl-4-(((2S)-4-methyl-3,4-dihydro-2H-1,4-benzoxazin-2-yl)methoxy)benzoyl)amino)phenyl)cyclopropanecarboxylic acid, 1-(5-((3-chloro-4-((2S)-2,3-dihydro-1,4-benzodioxin-2-ylmethoxy)-2-methylbenzoyl)amino)-2-methylphenyl)cyclopropanecarboxylic acid, 4-(3-((4-(((2S)-4,6-dimethyl-3,4-dihydro-2H-1,4-benzoxazin-2-yl)methoxy)-2,3-dimethylbenzoyl)amino)-4-fluorophenyl)tetrahydro-2H-pyran-4-carboxylic acid, 4-(4-chloro-3-((4-(((2S)-6-methoxy-4-methyl-3,4-dihydro-2H-1,4-benzoxazin-2-yl)methoxy)-2-methylbenzoyl)amino)phenyl)tetrahydro-2H-pyran-4-carboxylic acid, 4-(5-((4-((2R)-2,3-dihydro-1,4-benzodioxin-2-ylmethoxy)-2-fluoro-5-methylbenzoyl)amino)-2-methylphenyl)tetrahydro-2H-pyran-4-carboxylic acid, 4-(4-chloro-3-((5-chloro-4-(((2R)-1-ethyl-2,3-dihydro-1H-indol-2-yl)methoxy)-2-fluorobenzoyl)amino)phenyl)tetrahydro-2H-pyran-4-carboxylic acid, 4-(3-((2-chloro-3-methyl-4-(((2S)-4-methyl-3,4-dihydro-2H-1,4-benzoxazin-2-yl)methoxy)benzoyl)amino)-4-fluorophenyl)tetrahydro-2H-pyran-4-carboxylic acid, 2-methyl-2-(3-(((4-(((2S)-4-methyl-3,4-dihydro-2H-1,4-benzoxazin-2-yl)methoxy)phenyl)sulfonyl)amino)phenyl)propanoic acid, 2-methyl-2-(3-(methyl((2-methyl-4-(((2S)-4-methyl-3,4-dihydro-2H-1,4-benzoxazin-2-yl)methoxy)phenyl)sulfonyl)amino)phenyl)propanoic acid, (3-(((2-chloro-4-(((2S)-4-methyl-3,4-dihydro-2H-1,4-benzoxazin-2-yl)methoxy)phenyl)sulfonyl)(isobutyl)amino)phenyl)(difluoro)acetic acid, 1-(2-chloro-5-(((4-(((2S)-7-fluoro-4-methyl-3,4-dihydro-2H-1,4-benzoxazin-2-yl)methoxy)-2-methylphenyl)sulfonyl)(methyl)amino)phenyl)cyclopropanecarboxylic acid, (3-(((2-chloro-4-(((2S)-7-methoxy-4-methyl-3,4-dihydro-2H-1,4-benzoxazin-2-yl)methoxy)phenyl)sulfonyl)(isobutyl)amino)-5-methylphenyl)(oxo)acetic acid, (3-chloro-5-(((4-(((2S)-4,7-dimethyl-3,4-dihydro-2H-1,4-benzoxazin-2-yl)methoxy)phenyl)sulfonyl)amino)phenyl)(difluoro)acetic acid, 2-(2-chloro-5-(((4-((2R)-2,3-dihydro-1,4-benzodixin-2-ylmethoxy)phenyl)sulfonyl)(isobutyl)amino)phenyl)-2-methylpropanoic acid, (3-((4-((2S)-2,3-dihydro-1,4-benzodioxin-2-ylmethoxy)-2,6-dimethylbenzoyl)amino)phenyl)acetic acid, (4-chloro-3-((2,6-dimethyl-4-(((2R)-4-methyl-3,4-dihydro-2H-1,4-benzoxazin-2-yl)methoxy)benzoyl)amino)phenyl)acetic acid, (3-((4-(((2S)-5-chloro-1-ethyl-2,3-dihydro-1H-indol-2-yl)methoxy)-2,5-dimethylbenzoyl)amino)-5-fluorophenyl)acetic acid, (4-chloro-3-((4-(((2R)-5-fluoro-2,3-dihydro-1-benzofuran-2-yl)methoxy)-2,6-dimethylbenzoyl)amino)phenyl)acetic acid, (3-((4-((3R)-2,3-dihydro-1-benzofuran-3-ylmethoxy)-2,6-dimethylbenzoyl)amino)-4-methylphenyl)acetic acid, (3-((2,5-dimethyl-4-(((2S)-4-methyl-3,4-dihydro-2H-1,4-benzoxazin-2-yl)methoxy)benzoyl)amino)-4-ethylphenyl)acetic acid, (5-((2,6-dimethyl-4-(((2S)-4-methyl-3,4-dihydro-2H-1,4-benzoxazin-2-yl)methoxy)benzoyl)amino)-2-isopropylphenyl)acetic acid, (3-((2-ethyl-5-methyl-4-(((2S)-4-methyl-3,4-dihydro-2H-1,4-benzoxazin-2-yl)methoxy)benzoyl)amino)phenyl)acetic acid, (5-((5-methyl-2-methyl-4-(((2S)-4-methyl-3,4-dihydro-2H-1,4-benzoxazin-2-yl)methoxy)benzoyl)amino)-2-methoxyphenyl)acetic acid, and (2-chloro-5-((2,5-dimethoxy-4-(((2S)-4-methyl-3,4-dihydro-2H-1,4-benzoxazin-2-yl)methoxy)benzoyl)amino)phenyl)acetic acid, compounds presented in example, salts thereof, solvates thereof, and prodrugs thereof.

As more preferable compounds, the present invention includes (1) (3-((2,3-dimethyl-4-(((2S)-4-methyl-3,4-dihydro-2H-1,4-benzoxazin-2-yl)methoxy)benzoyl)amino)-4-fluorophenyl)acetic acid, (2) (4-chloro-3-((2,3-dimethyl-4-(((2S)-4-methyl-3,4-dihydro-2H-1,4-benzoxazin-2-yl)methoxy)benzoyl)amino)phenyl)acetic acid, (3) (4-chloro-3-((2,6-dimethyl-4-(((2S)-4-methyl-3,4-dihydro-2H-1,4-benzoxazin-2-yl)methoxy)benzoyl)amino)phenyl)acetic acid, (4) (4-chloro-3-((5-chloro-2-fluoro-4-(((2S)-4-methyl-3,4-dihydro-2H-1,4-benzoxazin-2-yl)methoxy)benzoyl)amino)phenyl)acetic acid, (5) (4-chloro-3-((2,5-dimethyl-4-(((2S)-4-methyl-3,4-dihydro-2H-1,4-benzoxazin-2-yl)methoxy)benzoyl)amino)phenyl)acetic acid, (6) (4-chloro-3-((2-fluoro-5-methyl-4-(((2S)-4-methyl-3,4-dihydro-2H-1,4-benzoxazin-2-yl)methoxy)benzoyl)amino)phenyl)acetic acid, (7) (4-chloro-3-((2,5-difluoro-4-(((2S)-4-methyl-3,4-dihydro-2H-1,4-benzoxazin-2-yl)methoxy)benzoyl)amino)phenyl)acetic acid, (8) (3-((2,3-dimethyl-4-(((2S)-4-methyl-3,4-dihydro-2H-1,4-benzoxazin-2-yl)methoxy)benzoyl)amino)-4-methylphenyl)acetic acid, (9) (3-((2,3-dimethyl-4-(((2S)-4-methyl-3,4-dihydro-2H-1,4-benzoxazin-2-yl)methoxy)benzoyl)amino)-5-methylphenyl)acetic acid,

(10) (3-((2,3-dimethyl-4-(((2S)-4-methyl-3,4-dihydro-2H-1,4-benzoxazin-2-yl)methoxy)benzoyl)amino)phenyl)acetic acid,

(11) (3-((2,6-dimethyl-4-(((2S)-4-methyl-3,4-dihydro-2H-1,4-benzoxazin-2-yl)methoxy)benzoyl)amino)phenyl)acetic acid,

(12) (3-((2,6-dimethyl-4-(((2S)-4-methyl-3,4-dihydro-2H-1,4-benzoxazin-2-yl)methoxy)benzoyl)amino)-5-methylphenyl)acetic acid,

(13) (5-((2,6-dimethyl-4-(((2S)-4-methyl-3,4-dihydro-2H-1,4-benzoxazin-2-yl)methoxy)benzoyl)amino)-2-fluorophenyl)acetic acid,

(14) (5-((2,5-dimethyl-4-(((2S)-4-methyl-3,4-dihydro-2H-1,4-benzoxazin-2-yl)methoxy)benzoyl)amino)-2-methylphenyl)acetic acid,

(15) (5-((2,5-dimethyl-4-(((2S)-4-methyl-3,4-dihydro-2H-1,4-benzoxazin-2-yl)methoxy)benzoyl)amino)-2-fluorophenyl)acetic acid,
(16) (3-((2,5-dimethyl-4-(((2S)-4-methyl-3,4-dihydro-2H-1,4-benzoxazin-2-yl)methoxy)benzoyl)amino)phenyl)acetic acid,
(17) (5-((2,3-dimethyl-4-(((2S)-4-methyl-3,4-dihydro-2H-1,4-benzoxazin-2-yl)methoxy)benzoyl)amino)-2-fluorophenyl)acetic acid,
(18) (5-((2,3-dimethyl-4-(((2S)-4-methyl-3,4-dihydro-2H-1,4-benzoxazin-2-yl)methoxy)benzoyl)amino)-2-methylphenyl)acetic acid,
(19) (5-((2,6-dimethyl-4-(((2S)-4-methyl-3,4-dihydro-2H-1,4-benzoxazin-2-yl)methoxy)benzoyl)amino)-2-methylphenyl)acetic acid,
(20) (3-((2,6-dimethyl-4-(((2S)-4-methyl-3,4-dihydro-2H-1,4-benzoxazin-2-yl)methoxy)benzoyl)amino)-4-methylphenyl)acetic acid,
(21) (3-((2,6-dimethyl-4-(((2S)-4-methyl-3,4-dihydro-2H-1,4-benzoxazin-2-yl)methoxy)benzoyl)amino)-4-fluorophenyl)acetic acid,
(22) (3-((2,5-dimethyl-4-(((2S)-4-methyl-3,4-dihydro-2H-1,4-benzoxazin-2-yl)methoxy)benzoyl)amino)-4-fluorophenyl)acetic acid,
(23) (3-((2,5-dimethyl-4-(((2S)-4-methyl-3,4-dihydro-2H-1,4-benzoxazin-2-yl)methoxy)benzoyl)amino)-4-methylphenyl)acetic acid,
(24) (3-((2,5-dimethyl-4-(((2S)-4-methyl-3,4-dihydro-2H-1,4-benzoxazin-2-yl)methoxy)benzoyl)amino)-5-methylphenyl)acetic acid,
(25) (4-chloro-3-((4-((2R)-2,3-dihydro-1,4-benzodioxin-2-ylmethoxy)-2,6-dimethylbenzoyl)amino)phenyl)acetic acid,
(26) (2-chloro-5-((2,3-dimethyl-4-(((2S)-4-methyl-3,4-dihydro-2H-1,4-benzoxazin-2-yl)methoxy)benzoyl)amino)phenyl)acetic acid,
(27) (2-chloro-5-((2,6-dimethyl-4-(((2S)-4-methyl-3,4-dihydro-2H-1,4-benzoxazin-2-yl)methoxy)benzoyl)amino)phenyl)acetic acid,
(28) (2-chloro-5-((2,5-dimethyl-4-(((2S)-4-methyl-3,4-dihydro-2H-1,4-benzoxazin-2-yl)methoxy)benzoyl)amino)phenyl)acetic acid,
(29) (4-chloro-3-((4-((3R)-2,3-dihydro-1-benzofuran-3-ylmethoxy)-2,6-dimethylbenzoyl)amino)phenyl)acetic acid,
(30) (4-chloro-3-((2,6-dimethyl-4-(((3R)-5-methyl-2,3-dihydro-1-benzofuran-3-yl)methoxy)benzoyl)amino)phenyl)acetic acid,
(31) (4-chloro-3-((4-((2S)-2,3-dihydro-1-benzofuran-2-ylmethoxy)-2,6-dimethylbenzoyl)amino)phenyl)acetic acid,
(32) (3-((4-(1,3-benzodioxol-2-ylmethoxy)-2,6-dimethylbenzoyl)amino)-4-chlorophenyl)acetic acid etc.

As furthermore preferable compounds, the present invention includes
(1) 2-(4-chloro-3-((2-chloro-4-(((2S)-4-methyl-3,4-dihydro-2H-1,4-benzoxazin-2-yl)methoxy)benzoyl)amino)phenyl)-2-methylpropanoic acid,
(2) (4-chloro-3-((2-chloro-4-(((2S)-4-methyl-3,4-dihydro-2H-1,4-benzoxazin-2-yl)methoxy)benzoyl)amino)phenyl)(difluoro)acetic acid,
(3) (4-chloro-3-((2-chloro-4-(((2S)-4-methyl-3,4-dihydro-2H-1,4-benzoxazin-2-yl)methoxy)benzoyl)amino)phenyl)(oxo)acetic acid,
(4) 2-(4-chloro-3-((2,5-dimethyl-4-(((2S)-4-methyl-3,4-dihydro-2H-1,4-benzoxazin-2-yl)methoxy)benzoyl)amino)phenyl)-2-methylpropanoic acid,
(5) 2-(4-chloro-3-((2,6-dimethyl-4-(((2S)-4-methyl-3,4-dihydro-2H-1,4-benzoxazin-2-yl)methoxy)benzoyl)amino)phenyl)-2-methylpropanoic acid,
(6) 2-(3-((2,5-dimethyl-4-(((2S)-4-methyl-3,4-dihydro-2H-1,4-benzoxazin-2-yl)methoxy)benzoyl)amino)-4-methylphenyl)-2-methylpropanoic acid,
(7) 1-(4-chloro-3-((2,6-dimethyl-4-(((2S)-4-methyl-3,4-dihydro-2H-1,4-benzoxazin-2-yl)methoxy)benzoyl)amino)phenyl)cyclopropanecarboxylic acid,
(8) 1-(4-chloro-3-((2,5-dimethyl-4-(((2S)-4-methyl-3,4-dihydro-2H-1,4-benzoxazin-2-yl)methoxy)benzoyl)amino)phenyl)cyclopropanecarboxylic acid,
(9) 1-(4-chloro-3-((2-ethyl-4-(((2S)-4-methyl-3,4-dihydro-2H-1,4-benzoxazin-2-yl)methoxy)benzoyl)amino)phenyl)cyclopropanecarboxylic acid,
(10) (4-chloro-3-((2,6-dimethyl-4-(((2S)-4-methyl-3,4-dihydro-2H-1,4-benzoxazin-2-yl)methoxy)benzoyl)amino)phenyl)acetic acid,
(11) (3-((2,6-dimethyl-4-(((2S)-4-methyl-3,4-dihydro-2H-1,4-benzoxazin-2-yl)methoxy)benzoyl)amino)-5-methylphenyl)acetic acid etc.

The present invention includes compounds that $R^{12}$ and $R^{13}$ in formula (I) simultaneously present hydrogen atoms and that fill at least one under conditions of the following (1)-(6);
(1) $R^2$ is oxidized C1-6 alkyl, (2) two $R^2$ substituted for the adjacent carbon atom together represent C2-5 alkenylene (the said C2-5 alkenylene may be substituted by a substituent.) in which the carbon atom may replace an oxygen atom, a nitrogen atom, or a sulfur atom that may be oxidized, (3) two $R^2$ substituted for the adjacent carbon atom together represent C2-5 alkenyne (the said C2-5 alkenyne may be substituted by a substituent.) in which the carbon atom may replace an oxygen atom, a nitrogen atom, or a sulfur atom, (4) $R^3$ is oxidized C1-6 alkyl, (5) $R^4$ is oxidized C1-6 alkyl, and (6) $R^5$ is oxidized C1-6 alkyl, salts thereof, solvates thereof, and prodrugs thereof.

Concretely, for example, they include
(3-((5-(hydroxymethyl)-2-methyl-4-(((2S)-4-methyl-3,4-dihydro-2H-1,4-benzoxazin-2-yl)methoxy)benzoyl)amino)phenyl)acetic acid,
(3-((2,6-dimethyl-4-(((2S)-4-methyl-3,4-dihydro-2H-1,4-benzoxazin-2-yl)methoxy)benzoyl)amino)-4-(hydroxymethyl)phenyl)acetic acid,
(4-chloro-3-((4-(((3R)-5-(hydroxymethyl)-2,3-dihydro-1-benzofuran-3-yl)methoxy)-2,6-dimethylbenzoyl)amino)phenyl)acetic acid,
(3-((5-formyl-2-methyl-4-(((2S)-4-methyl-3,4-dihydro-2H-1,4-benzoxazin-2-yl)methoxy)benzoyl)amino)phenyl)acetic acid,
(3-((2,6-dimethyl-4-(((2S)-4-methyl-3,4-dihydro-2H-1,4-benzoxazin-2-yl)methoxy)benzoyl)amino)-4-formylphenyl)acetic acid,
(3-((2-chloro-3-fluoro-4-(((2S)-6-(hydroxymethyl)-2,3-dihydro-1,4-benzodioxin-2-yl)methoxy)benzoyl)amino)-4-fluorophenyl)acetic acid,
(5-((4-(((2R)-1-ethyl-2,3-dihydro-1H-indol-2-yl)methoxy)-2-(hydroxymethyl)-6-methylbenzoyl)amino)-2-methylphenyl)acetic acid,
5-(((3-(carboxymethyl)phenyl)amino)carbonyl)-4-methyl-2-(((2S)-4-methyl-3,4-dihydro-2H-1,4-benzoxazin-2-yl)methoxy)benzoic acid,
4-(carboxymethyl)-2-((2,6-dimethyl-4-(((2S)-4-methyl-3,4-dihydro-2H-1,4-benzoxazin-2-yl)methoxy)benzoyl)amino)benzoic acid, or (6-((2,5-dimethyl-4-(((2S)-4-methyl-3,4-dihydro-2H-1,4-benzoxazin-2-yl)methoxy)benzoyl)amino)-2,3-dihydro-1H-inden-4-yl)acetic acid etc.

Since the compounds of the present invention specifically bind to DP receptors and bind weakly to other prostaglandins receptors, they have the excellent selectivity. Additionally, the compounds of the present invention have the excellent solubility. In physical, chemical, and pharmacological property that is most requested in drug development, the compounds of the present invention have the requirement for which they become very excellent medicines (The Merck Manual of Diagnosis and Therapy (17th Ed.), published by Merck & Co).

Process for Production of the Compounds of the Present Invention

The compounds of the present invention represented by formula (I) can be produced by known methods, e.g., methods as shown below, methods according to these method, and methods shown in examples. Further, raw material salts can be used in each following process. As such salts, the pharmaceutically allowable salts of the aforementioned formula (I) can be used.

I. Among the compounds represented by formula (I), the compound in which $R^1$ represents C1-4 alkyl, C2-4 alkenyl or benzyl, i.e., those represented by formula (IA)

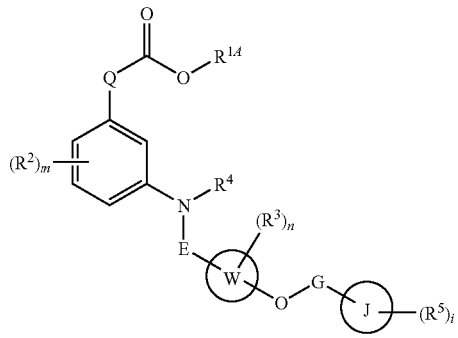

(IA)

wherein Q is $-C(R^{12})(R^{13})-$, $R^{1A}$ is C1-4 alkyl, C2-4 alkenyl or benzyl, and other symbols have the same meanings as the aforementioned, can be produced according to the process as mentioned below.

(a) The compound in which E represents $-C(=O)-$ or $-S(O)_2-$ in formula (IA), i.e., the compound represented by formula (IA-1)

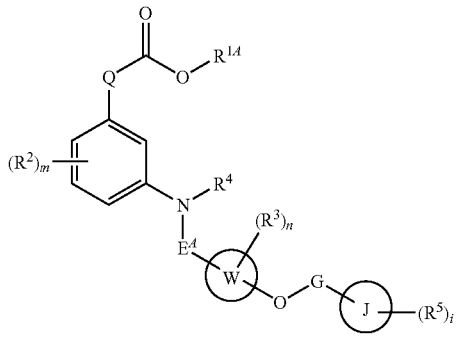

(IA-1)

wherein $E^A$ is $-C(=O)-$ or $-S(O)_2-$ and other symbols have the same meanings as the aforementioned, can be produced by subjecting the compound represented by formula (II-1)

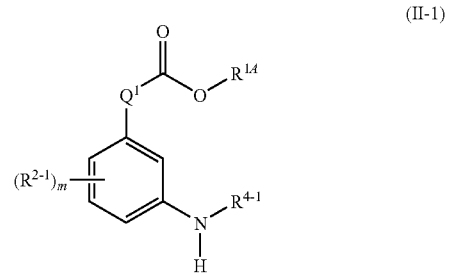

(II-1)

wherein $Q^1$ is Q, $R^{2-1}$ has the same meaning as $R^2$, if necessary, carboxyl, hydroxyl, amino, or thiol in the group represented by $R^{2-1}$ is protected, $R^{4-1}$ is a hydrogen atom, and other symbols have the same meanings as aforementioned, or the compound represented by formula (II-2)

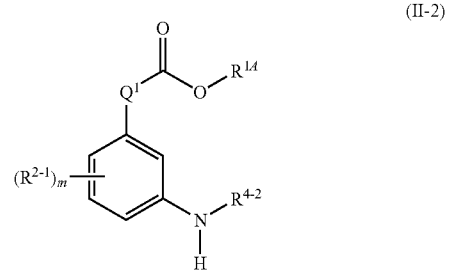

(II-2)

wherein $R^{4-2}$ is C1-6 alkyl or benzyl and other symbols have the same meanings as the aforementioned, to an amidation reaction with a compound represented by formula (III)

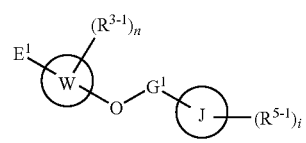

(III)

wherein $E^1$ is $-COOH$ or $-SO_3H$; $G^1$, $R^{3-1}$, and $R^{5-1}$ have the same meanings as $R^3$, and $R^5$, respectively, if necessary, carboxyl, hydroxyl, amino, nitrogen atoms, or thiol in the group represented by $G^1$, $R^{3-1}$, and $R^{5-1}$ is protected, and other symbols have the same meanings as those aforementioned, followed by subjecting to deprotection.

The amidation reaction has been known and its examples are (1) a process using an acid halide,
(2) a process using a mixed acid anhydride and
(3) a process using a condensing agent.

Such processes will be specifically illustrated as follows.

(1) A process using an acid halide is carried out, for example, in such a manner that carboxylic acid is subjected to a reaction with an acid halide (oxalyl chloride and thionyl chloride etc.) in an organic solvent (chloroform, dichloromethane, diethyl ether, tetrahydrofuran, dimethoxyethane, acetonitrile, ethyl acetate toluene, etc.) or without solvent at −20° C. to refluxing temperature and the resulting acid halide is subjected to a reaction with an amine in the presence of a base (pyridine, triethylamine, dimethylaniline, dimethylaminopyridine, diisopropylethylamine, N-methylmorpholine, 5-ethyl-2-methylpyridine (MEP), etc.) in an inert organic solvent (chloroform, dichloromethane, diethyl ether, tetrahydrofuran, acetonitrile, ethyl acetate etc.) at the temperature of 0 to 40° C. This reaction is preferably carried out under anhydrous condition under inert gas atmosphere (argon and nitrogen etc.). This reaction can be carried out by a reaction the resulting acid halide with an amine in an organic solvent (dioxane, tetrahydrofuran, dichloromethane, etc.) in the presence or absence of a phase-transfer catalyst (quaternary ammonium salts, e.g., such as tetrabutylammonium chloride, triethylbenzylammonium chloride, tri-n-octylmethylammonium chloride, trimethyldecylammonium chloride, tetramethylammonium bromide, etc.) using alkali solution (sodium bicarbonate water and sodium hydroxide solution etc.) at 0 to 40° C.

(2) A process using a mixed acid anhydride is carried out, for example, in such a manner that carboxylic acid is made to react with an acid halide (pivaloyl chloride, tosyl chloride, and mesyl chloride, etc.) or with an acid derivative (ethyl chloroformate and isobutyl chloroformate etc.) at 0 to 40° C. in the presence or absence of an organic solvent (chloroform, dichloromethane, diethyl ether, and tetrahydrofuran, etc.) or without a solvent in the presence of a base (pyridine, triethylamine, dimethylaniline, dimethylaminopyridine, and diisopropylethylamine, etc.) and the resulting mixed acid anhydride is subjected to a reaction with an amine in an organic solvent (chloroform, dichloromethane, diethyl ether, tetrahydrofuran, etc.) at 0 to 40° C. This reaction is preferably carried out under anhydrous condition under inert gas atmosphere (argon and nitrogen etc.).

(3) A process using a condensing agent is carried out, for example, in such a manner that carboxylic acid is subjected to a reaction with an amine, using a condensing agent (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propylphosphonic acid cyclic anhydride; PPA, etc., with or without 1-hydroxybenztriazole (HOBt), in the presence or absence of a base (pyridine, triethylamine, dimethylanilin, dimethylaminopyridine, etc.) in an organic solvent (chloroform, dichloromethane, dimethylformamide, diethyl ether, tetrahydrofuran, etc.) or without a solvent. at 0 to 40° C. This reaction is preferably carried out under anhydrous condition under inert gas atmosphere (argon and nitrogen etc.).

The deprotection reaction of a protective group for carboxyl, hydroxyl, amino, or thiol is known and its examples are as follows;
(1) a hydrolyzing reaction with an alkali;
(2) a deprotection reaction under an acidic condition;
(3) a deprotection reaction by hydrogenolysis;
(4) a deprotection reaction of silyl;
(5) a deprotection reaction using metal; and
(6) a deprotection reaction using an organic metal.

Those methods will be specifically illustrated as follows.

(1) A deprotection reaction using an alkali is carried out, for example, at the temperature of 0 to 80° C. using a hydroxide of alkaline metal (sodium hydroxide, potassium hydroxide, lithium hydroxide, etc.), a hydroxide of alkaline earth metal (barium hydroxide and calcium hydroxide etc.), a carbonate (sodium carbonate and potassium carbonate etc.), an aqueous solution thereof or a mixture thereof in an organic solvent (methanol, tetrahydrofuran and dioxane etc.).

(2) A deprotection reaction under an acidic condition is carried out, for example, at the temperature of 0 to 100° C. in an organic acid (acetic acid, trifluoroacetic acid, methanesulfonic acid, p-tosylic acid, etc.), an inorganic acid (hydrochloric acid and sulfuric acid, etc.) or a mixture thereof (hydrogen bromide/acetic acid etc) in an organic solvent (dichloromethane, chloroform, dioxane, ethyl acetate, and anisole, etc.) in the presence or absence of 2,2,2-trifluoroethanol.

(3) A deprotection reaction by hydrogenolysis is carried out, for example, at the temperature of 0 to 200° C., under hydrogen atmosphere of ordinary pressure or high pressure or in the presence of ammonium formate, in the presence of a catalyst (palladium-carbon, palladium black, palladium hydroxide, platinum hydroxide, platinum oxide, and Raney nickel, etc.), in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitrites (acetonitrile etc.), amides (dimethylformamide etc.), water, ethyl acetate, acetic acid, or a mixed solvent comprising two or more thereof, etc.).

(4) A deprotection reaction of silyl is carried out, for example, at the temperature of 0 to 40° C. using tetrabutylammonium fluoride in an organic solvent miscible with water (tetrahydrofuran, acetonitrile, etc.).

(5) A deprotection reaction using metal is carried out, for example, at the temperature of 0 to 40° C. with ultrasonic wave, if necessary, in the presence of powdery zinc in an acidic solvent (acetic acid, a buffer of pH 4.2 to 7.2 and a mixed solution of a solution thereof and an organic solvent such as tetrahydrofuran).

(6) A deprotection reaction using a metal complex is carried out, for example, at the temperature of 0 to 40° C. using a metal complex (tetrakistriphenylphosphine palladium (0), bis(triphenylphosphine)palladium (II) dichloride, palladium (II) acetate, tris(triphenylphosphine) rhodium (I) chloride, etc.), in the presence or absence of a phosphine agent (triphenyl phosphine etc.), in the presence of a trap reagent (tributyltin hydride, triethylsilane, dimedone, morpholine, diethylamine, pyrrolidine, etc.), an organic acid (acetic acid, formic acid, 2-ethylhexanoic acid, etc.) and/or an organic acid salt (sodium 2-ethylhexanoate, potassium 2-ethylhexanoate, etc.) in an organic solvent (dichloromethane, dimethylformamide, tetrahydrofuran, ethyl acetate, acetonitrile, dioxane, ethanol, etc.), water, or a mixed solvent thereof.

Besides the aforementioned, the deprotection is carried out by a method described in T. W. Greene, Protective Groups in Organic Synthesis, Wiley, N.Y., and 1999.

The protective group for carboxyl includes such as, e.g., methyl, ethyl, allyl, t-butyl, trichloroethyl group, benzyl (Bn), phenacyl, p-methoxybenzyl, trityl, 2-chlorotrityl, solid phase carrier thereof, etc.

The protective group for hydroxyl includes such as, e.g., methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc), etc.

The protective group of amino includes such as, e.g., benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), 2-(trimethylsilyl)ethoxymethyl (SEM), etc.

The protective group for thiol includes such as, e.g., benzyl, methoxybenzyl, methoxymethyl (MOM), 2-tetrahydropyranyl (THP), diphenylmethyl, acetyl (Ac), etc.

With regard to the protective group for carboxyl, hydroxyl, amino, and thiol, there is no particular limitation to the above ones so far as it is a group which can be easily and selectively detached. For example, the one described in "T. W. Greene, Protective Groups in Organic Synthesis, Wiley, N.Y., 1999" can be used.

As a person skilled in the art can easily understand it, the aimed compound of the present invention can be easily produced by using appropriate ones among those deprotection reactions.

(b) A compound of formula (IA) in which E represents —$CH_2$—, i.e., a compound represented by formula (IA-2)

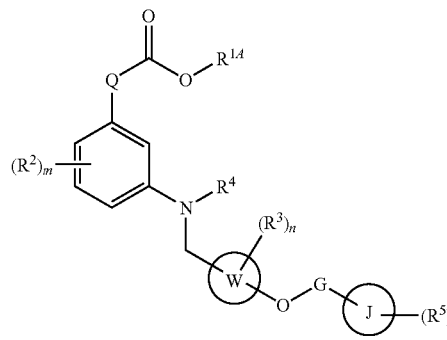

(IA-2)

wherein all symbols have the same meanings as the aforementioned, can be produced by subjecting a compound represented by formula (II-1) or formula (II-2) and a compound represented by formula (IV)

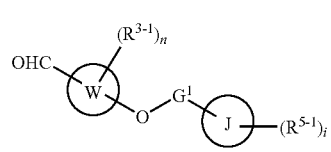

(IV)

wherein all symbols have the same meanings as the aforementioned, to a reductive amination reaction, followed by subjecting to deprotection, if necessary.

The reductive amination reaction has been known, for example, it is carried out at the temperature of 0 to 40° C. in the presence of a reducing agent (sodium triacetoxyborohydride, sodium cyanoborohydride, sodium borohydride, zinc borohydride, diisodouthylaluminum hydride, etc.) in an organic solvent (tetrahydrofuran, diethyl ether, dichloroethane, dichloromethane, dimethylformamide, acetic acid, methanol, ethanol, a mixture thereof, etc.) or at the temperature of 0 to 200° C. in the presence of a catalyst (palladium-carbon, palladium black, hydroxide palladium, oxidation platinum, Raney Nickel, etc.) in an solvent (ethers (tetrahydrofuran, dioxane, dimethoxyethane, diethyl ether, etc.), alcohols (methanol, ethanol, etc.), benzenes (benzene, toluene, etc.), ketones (acetone, methylethylketone, etc.), nitriles (acetonitrile etc.), amides (dimethyl formamide etc.), water, ethyl acetate, acetate, or two or more mixed solvent thereof, etc.) under atmospheric or pressurized hydrogen atmosphere.

(c) A compound represented by formula (IA) also can be produced by subjecting a compound represented by formula (V)

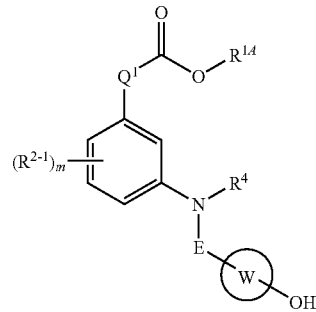

(V)

wherein all symbols have the same meanings as the aforementioned, and a compound represented by formula (VI)

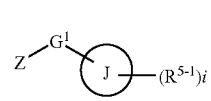

(VI)

wherein Z is a leaving group or hydroxyl and all other symbols have the same meanings as the aforementioned, to an etherification reaction, followed by subjecting to deprotection, if necessary.

The etherification reaction has been known and is carried out, for example, at 0° C. to a refluxing temperature in the presence of an alkaline metal hydroxide (sodium hydroxide, potassium hydroxide, lithium hydroxide, etc.), an alkaline earth metal hydroxide (barium hydroxide, calcium hydroxide, etc.), a carbonate (cesium carbonate, sodium carbonate, potassium carbonate, calcium carbonate, etc.), an alkaline metal hydride (sodium hydride, potassium hydride, etc.), potassium phosphate ($K_3PO_4$), or an solution thereof, or a mixture thereof in an organic solvent (dimethylformamide, dimethyl sulfoxide, chloroform, dichloromethane, diethyl ether, tetrahydrofuran, methyl tert-butyl ether, etc.) when the compound represented by formula (VI) in which Z is a leaving group is used. It is carried out, for example, at 0 to 60° C. in the presence of an azo compound (diethyl azodicarboxylate, diisopropyl azodicarboxylate, 1,1'-(azodicarbonyl)-dipiperidine, 1,1'-azobis(N,N-dimethylformamide, etc.) and a phosphine compound (triphenyl phosphine, tributyl phosphine, trimethyl phosphine, polymer-supported triphenyl phosphine, etc.) in an organic solvent (dichloromethane, diethyl ether, tetrahydrofuran, acetonitrile, benzene, toluene, etc.) when the compound represented by formula (VI) in which Z is hydroxyl is used.

(d) A compound in which $R^4$ is $R^{4-2}$ or, i.e., a compound represented by formula (IA-3)

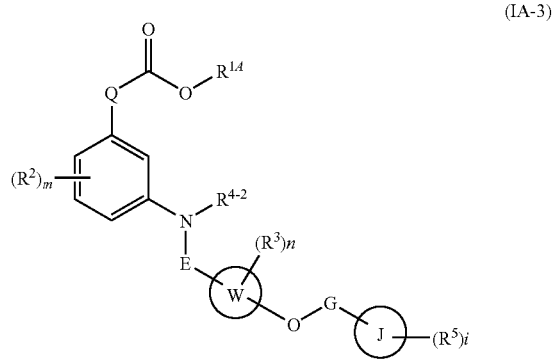

(IA-3)

wherein all symbols have the same meanings as the aforementioned, also can to be produced by subjecting a compound represented by formula (IA-4)

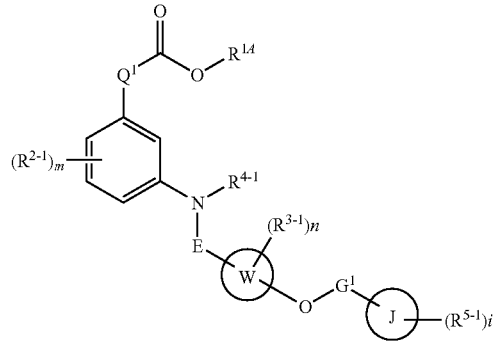

(IA-4)

wherein all symbols have the same meanings as the aforementioned to an N-alkylation reaction, followed by subjecting to deprotection, if necessary.

The N-alkylation reaction has been known and is carried out by the reaction of, for example, at 0 to 40° C. using an alkyl (C1-6) halide or a benzyl halide in the presence of a carbonate (cesium carbonate, sodium carbonate, potassium carbonate, etc.) in an organic solvent (dimethylformamide, dimethyl sulfoxide, chloroform, dichloromethane, diethyl ether, tetrahydrofuran, etc.).

In the case of a compound in which E in formula (IA-4) is $-SO_2-$, it also is carried out, for example, at 0 to 60° C. using a C1-6 alkyl alcohol or benzyl alcohol in the presence of an azo compound (diethyl azodicarboxylate, diisopropyl azodicarboxylate, 1,1'-(azodicarbonyl)dipiperidine, 1,1'-azobis(N,N-dimethylformamide), etc.) and a phosphine compound (triphenyl phosphine, tributyl phosphine, trimethyl phosphoine, polymer-supported triphenyl phosphine, etc.) in an organic solvent (dichloromethane, diethyl ether, tetrahydrofuran, acetonitrile, benzene, toluene, etc.).

II. A compound in which $R^1$ in formula (I) represents a hydrogen atom, i.e., a compound represented by formula (IB)

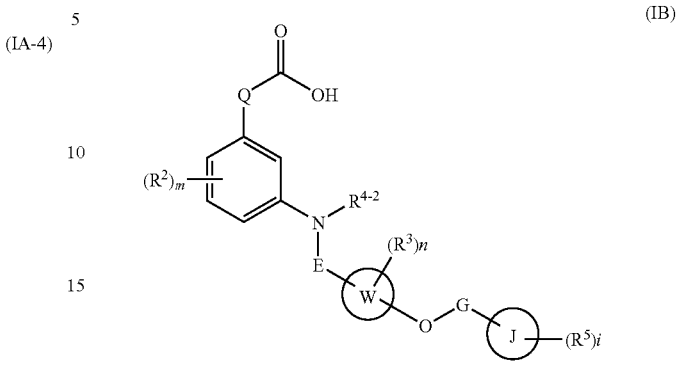

(IB)

wherein all symbols have the same meanings as the aforementioned, can be produced by subjecting a compound represented by formula (IA) to a deprotection reaction of a protective group for a carboxyl, followed by subjecting to a deprotection reaction of a protective group for hydroxyl, amino, a nitrogen atom, or thiol, if necessary.

The deprotection reaction of carboxyl can be carried out by the same methods as the aforementioned.

Though the persons skilled in the art can easily understand, the aimed compound of the present invention can be easily prepared by using these deprotection reactions properly.

The deprotection reaction of hydroxyl, amino, a nitrogen atom, or thiol can be carried out by the same methods as the aforementioned.

The compounds represented by formulae (II-1), (II-2), (III), (IV), (V), and (VI) have been known per se or can be easily produced by known methods.

For example, compounds in which $Q^1$ is methylene among the ones represented by formulae (II-1) and (II-2) can be produced by the process shown in the following reaction step formula 1.

In the reaction step formula 1, X represents a halogen atom, $R^{4-3}$ represents C1-5 alkyl or phenyl and other symbols have the same meanings as the aforementioned.

Reaction step formula 1

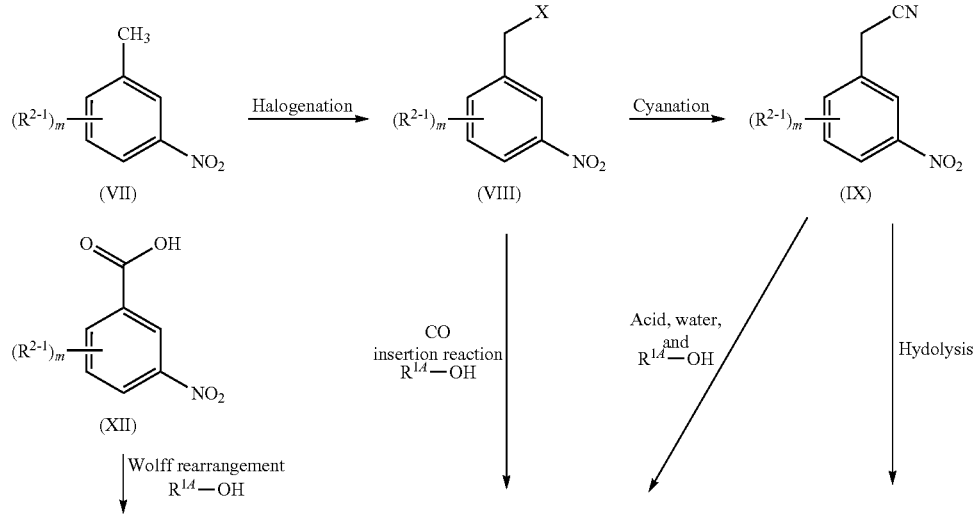

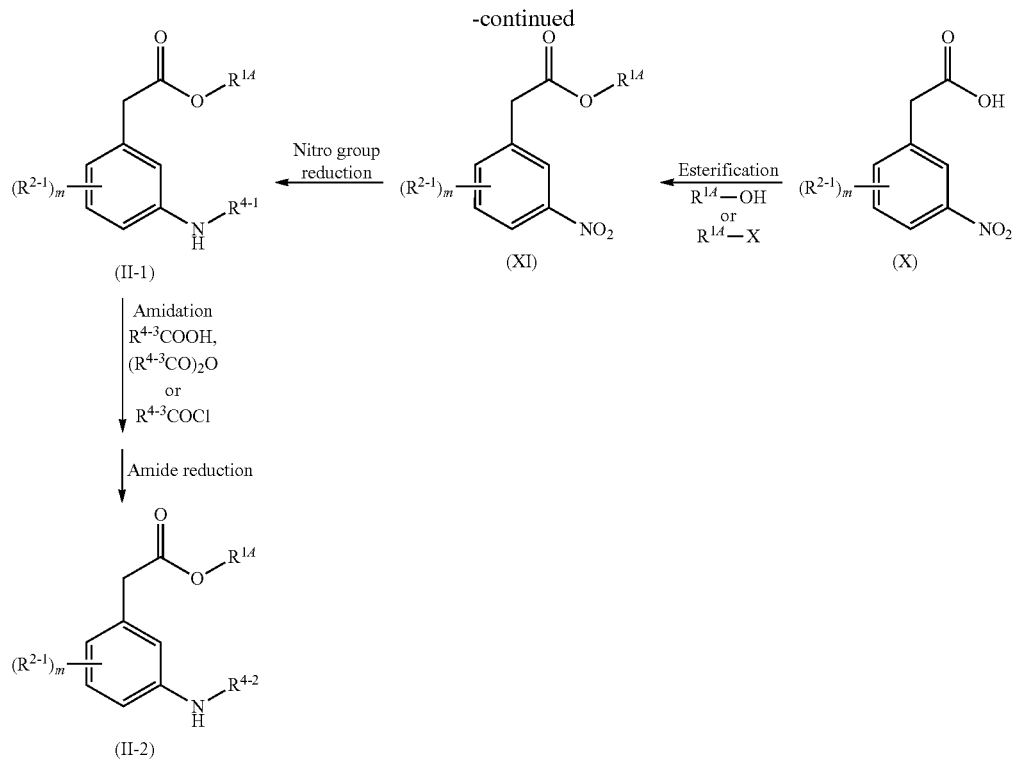

For example, compounds in which $Q^1$ is —$C(R^{12A})(R^{13A})$—($R^{12A}$ and $R^{13A}$ each independently represent C1-4 alkyl.) among the compounds represented by formula (II-1) can be produced by the process shown in the following reaction step formula 2.

In the reaction step formula 2, all symbols have the same meanings as the aforementioned.

Reaction step formula 2

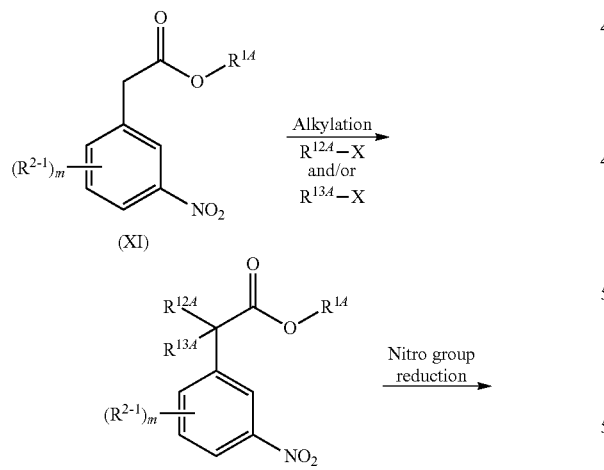

For example, compounds in which $Q^1$ is —$C(R^{12A})(R^{13A})$—($R^{12A}$ and $R^{13A}$ together represent C2-5 alkylene (the said C2-5 alkylene may be substituted by substituent(s).) in which the carbon atom may be replaced with an oxygen atom, a nitrogen atom, or a sulfur atom among the compounds represented by formula (II-1) can be produced by the process shown in the following reaction step formula 2-1.

In the reaction step formula 2-1, Y represents C2-5 alkylene (the said C2-5 alkylene may be substituted by substituent (s).) in which the carbon atom may replace an oxygen atom, a nitrogen atom, or a sulfur atom and other symbols have the same meanings as the aforementioned.

Reaction step formula 2-1

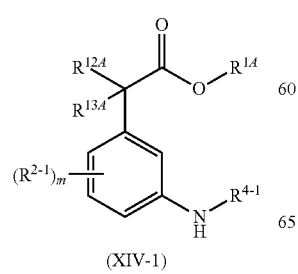

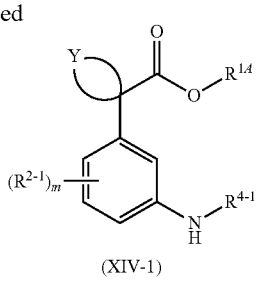

(XIV-1)

For example, compounds in which Q1 is difluoromethylene or keto among the compounds represented by formula (II-1) can be produced by the process shown in the following reaction step formula 3.

In the reaction step formula 3, all symbols have the same meanings as the aforementioned.

easily produced by a combination of the methods described in examples in the present specification and known methods, e.g., the methods described in "Comprehensive Organic Transformations: A Guide to Functional Group Preparations 2nd Edition (Richard C. Larock, John Wiley & Sons Inc, 1999)".

As be well known by the persons skilled in the art, a reaction with heating in each reaction of the present specification may be carried out by using bathe, oil bath, sand bath, or microwave.

In each reaction of the present specification, solid-phase supported reagents supported on high molecule polymer (e.g., polystyrene, polyacrylamide, polypropylene, polyethylene glycol, etc.) can be properly used.

In each reaction described in the present specification, the reaction product can be purified by conventional purification techniques, e.g., distillation under atmospheric or reduced pressure, high performance liquid chromatography, thin- Reaction step formula 3

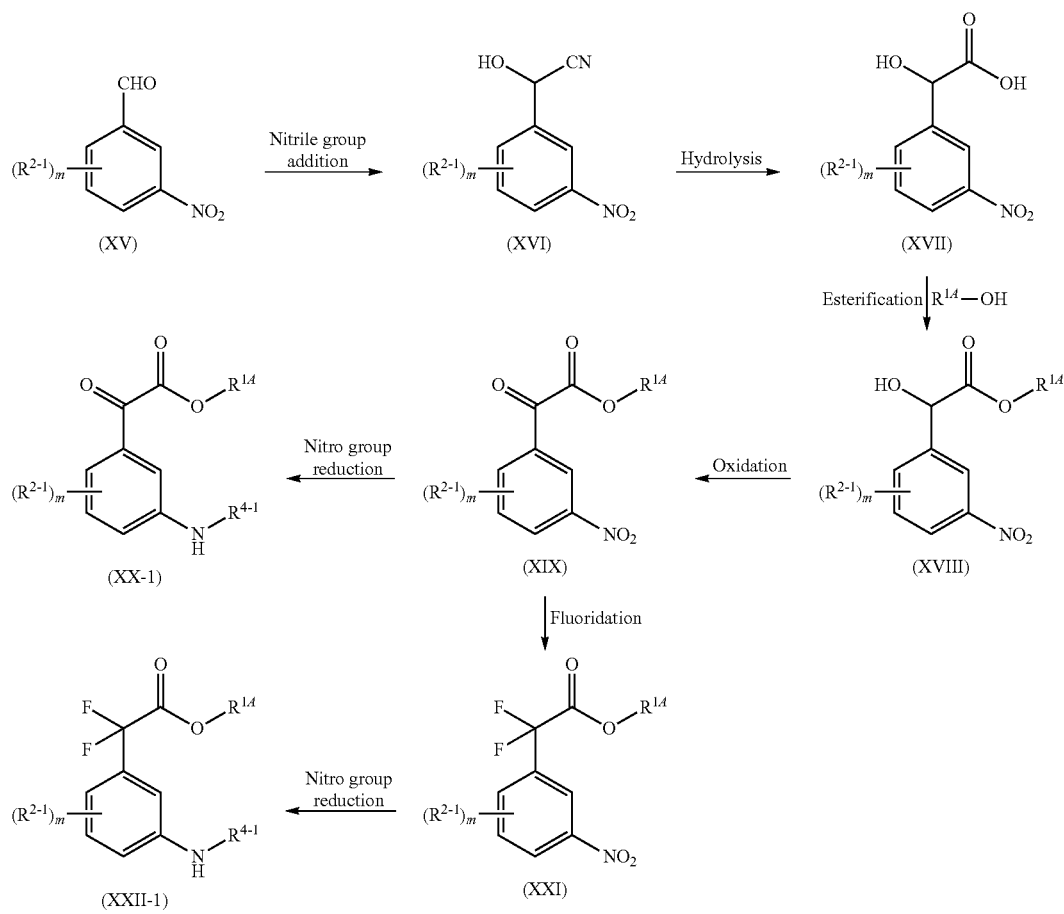

In the reaction step formula 1-3, the compounds represented by formulae (VII), (XII), and, (XV) used as starting materials have been known or can be easily produced by known methods, e.g., the method described in "Comprehensive Organic Transformations: A Guide to Functional Group Preparations 2nd Edition (Richard C. Larock, John Wiley & Sons Inc, 1999)".

Among the compounds of the present invention represented by formula (I), compounds expect for the above can be layer chromatography, or column chromatography using silica gel or magnesium silicate, washing, or recrystallization, etc. The purification may be carried out for each reaction or after some reactions.

Application to Pharmaceuticals

Since the compounds of the present invention represented by formula (I) bind and antagonize to DP receptors, it is considered that the compounds are useful for prevention and/or treatment of diseases mediated by DP receptors such as allergic disease (e.g., allergic rhinitis, allergic conjunctivitis, atopic dermatitis, bronchial asthma, food allergy, etc.), systemic mastocytosis, disorders accompanied by systemic mast cell activation, anaphylaxis shock, bronchoconstriction, urticaria, eczema, pimples, allergic bronchial pulmonary aspergillosis, sinusitis, migraine, nasal polypus, anaphylactic vasculitis, eosinophilic syndrome, contact dermatitis, diseases accompanied by itch (such as atopic dermatitis, urticaria, allergic conjunctivitis, allergic rhinitis and contact dermatitis), diseases (e.g., cataract, retinal detachment, inflammation, infection, sleeping disorders, etc.) which are generated secondarily as a result of behavior accompanied by itch (scratching, beating, etc.), inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis, irritable bowel syndrome, interstitial cystitis, muscular dystrophy, polymyositis and multiple sclerosis. Further, the compounds are considered to relate to sleeping and platelet aggregation and to be useful for these diseases.

Among the compounds of the present invention represented by formula (I), the compounds having a weak binding activity to receptors other than DP receptors would be used as a pharmaceutical having less side effects because it does not show other activity.

Toxicity

The toxicities of the compounds represented by formula (I) are very low so that the compounds are sufficiently safe for using as pharmaceuticals.

The compounds of the present invention represented by formula (I), pharmaceutically acceptable salts thereof, and solvents thereof may be administered as a combined preparation by combining with other pharmaceuticals for the purpose of; (1) supplementing and/or enhancing of prevention and/or treatment effect of the compounds, (2) improvement in pharmacokinetics and absorption and reduction of dose of the compounds and/or (3) reduction of side effects of the compounds.

The combined preparation with the compound of the present invention represented by formula (I) and other pharmaceutical may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of the present invention represented by formula (I) may be firstly administered followed by administering the other pharmaceutical or the other pharmaceutical may be administered firstly followed by administering the compound of the present invention represented by formula (I). Methods for each of the administration are the same or different.

The aforementioned other pharmaceuticals may be low molecular weight compounds, proteins, polypeptides, polynucleotides (DNA, RNA, and gene), antisenses, decoys, antibodies, or vaccines, etc. The dosages of other pharmaceuticals can be properly selected on the basis of the clinical dose. Further, the compounding ratio of other pharmaceutical and the pharmaceutical of the present invention can be properly selected on the basis of age and weight of a subject, medication method, administration period, disease, symptom, combination, etc. For example, 0.01 to 100 mass ratio of other pharmaceutical for 1 mass of the pharmaceutical of the present invention may be used. Two or more arbitrary other pharmaceuticals may be combinationally administered at a suitable rate. Other pharmaceuticals supplementing and/or enhancing of prevention and/or treatment effect of the pharmaceutical of the present invention include not only ones that were found up to the present, but also ones that will be found in the future.

There is no particular limitation for the diseases showing prevention and/or treatment effect by the aforementioned combined preparation, so far as it is a disease in which the prevention and/or treatment effect of the pharmaceutical of present invention are supplemented and/or enhanced.

Other pharmaceuticals for supplementing and/or enhancing the prevention and/or treatment effect of the compound of the present invention represented by formula (I) for allergic rhinitis include, e.g., antihistaminic agent, mediator release inhibitor, thromboxane synthetase inhibitor, thromboxane A2 receptor antagonist, leukotriene receptor antagonist, steroid, α-adrenaline receptor stimulator, xanthine derivative, cholinergic-blocking agent, nitrogen monoxide synthase inhibitor, etc.

Other pharmaceuticals for supplementing and/or enhancing the prevention and/or treatment effect of the compound of the present invention represented by formula (I) for allergic conjunctivitis include, e.g., leukotriene receptor antagonist, antihistaminic agent, mediator release inhibitor, non-steroid anti-inflammatory agent, prostaglandins, steroid, nitrogen monoxide synthase inhibitor, etc.

The antihistaminic agents include, e.g., ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK427, ZCR-2060, NIP-530, mometasone furoate, mizolastine, BP-294, andrast, auranofin, acrivastine, etc.

The mediator release inhibitors include, e.g., tranilast, sodium cromoglicate, amlexanox, repirinast, ibudilast, tazanolast, and pemirolast potassium etc. The thromboxane synthetase inhibitors include, e.g., ozagrel hydrochloride, imitrodast sodium, etc.

The thromboxane synthetase inhibitors include, e.g., ozagrel hydrochloride, imitrodast sodium.

The thromboxane A2 receptor antagonists include, e.g., seratrodast, ramatroban, domitroban calcium hydrate, KT-2-962, etc.

The leukotriene receptor antagonists include, e.g., pranlukast hydrate, montelukast, zafirlukast, MCC-847, KCA-757, CS-615, YM-158, L-740515, CP-195494, LM-1484, RS-635, A-93178, S-36496, BIIL-284, ONO4057, etc.

The steroid agents as its external application include, e.g., clobetasol propionate, diflorasone acetate, fluocinonide, mometasone furancarboxylate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate propionate, fluocinolone acetonide, beclomethasone propionate, triamcinolone acetonide, flumethasone pivalate, alclometasone propionate, clobetasone valerate, prednisolone, beclomethasone propionate, fludroxycortide, etc.

The internal medicines and injections include, e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, etc.

The inhalation agents include, e.g., beclomethasone propionate, fluticasone propionate, budesonide, flunisolide, triamcinolone, ST-126P, ciclesonide, dexamethasone palomithioate, mometasone furancarbonate, prasterone sulfonate, deflazacort, methylprednisolone suleptanate, methylprednisolone sodium succinate, etc.

The xanthine derivatives include, e.g., aminophylline, theophylline, doxophylline, cipamfylline, diprophylline, etc.

The anticholinergic agents include, e.g., ipratropium bromide, oxitropium bromide, flutropium bromide, cimetropium bromide, temiberin, tiotropium bromide, revatropate (UK-112166), etc.

The non-steroid anti-inflammatory agents include, e.g., sasapyrine, sodium salicylate, aspirin, aspirin dialuminate compounding, diflunisal, indomethacin, suprofen, ufenamate, dimethylisopropylazulene, bufexamac, felbinac, diclofenac, tolmetin sodium, clinoril, fenbufen, nabumetone, proglumetacin, indomethacin farnesyl, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, aluminoprofen, zaltoprofen, mefenamic acid, aluminum mefenamate, tolfenamic acid, floctafenine, ketophenylbutazone, oxyphenbutazone, piroxicam, tenoxicam, ampiroxicam, Napagelin ointment, epirizole, tiaramide hydrochloride, tinoridine hydrochloride, emorfazone, sulpyrine, migrenin, salidon, Sedes G. Amipylo-N, Solbon, pyrazolone-type remedy for common cold, acetaminophen, phenacetin, dimethothiazine mesylate, simetride-compounded agent, non-pyrazolone-type remedy for common cold, etc.

There is no particular limitation for the ratio by weight of the compound represented by formula (I) to other pharmaceutical.

Two or more of arbitrary other pharmaceuticals may be combinationally administered.

Other pharmaceuticals that supplement and/or enhance the prevention and/or treatment effect of the compound represented by formula (I) include not only one that has been already found but also one that will be found in future on the basis of the aforementioned mechanism.

When the compounds represented by formula (I) or non-toxic salts thereof used in the present invention or combined preparations of the compound represented by formula (I) and other pharmaceutical are used for the aforementioned purpose, they are systemically or topically administered in an oral or parenteral form usually.

The dose varies depending upon age, body weight, symptom, therapeutic effect, administering method, treating time and the like. Generally, 1 mg to 1,000 mg per an adult is orally administered once to several times per day, or 1 mg to 100 mg per an adult is parenterally administered (preferably, as a nasal agent, eye drops, or ointment) one to several times per day, or is continuously administered from vein for 1 to 24 hour(s) per day.

Since the dose changes depending on various conditions as described above, there are cases in which doses lower than or greater than the above ranges may be used.

The compounds represented by formula (I) or non-toxic salts thereof or a combined preparation of the compound represented by formula (I) and other pharmaceutical is used as a solid composition, liquid composition, and other composition for oral administration or as injection, external preparation, suppository, etc., for parenteral administration.

The solid composition for oral administration includes tablets, pills, capsules, diluted powder, granules, etc.

The capsules include hard capsules and soft capsules.

In such a solid composition, one or more active substance(s) is mixed with at least one inert diluent such as lactose, mannitol, glucose, hydroxypropyl cellulose, microcrystalline cellulose, starch, polyvinylpyrrolidone and magnesium metasilicate aluminate. The composition may contain an additive which is other than the inert diluent by a conventional method such as a lubricant such as magnesium stearate, a disintegrating agent such as calcium cellulose glycolate, a stabilizer such as lactose and a solubilizing agent such as glutamic acid and aspartic acid. Tablet or pill may, if necessary, be coated with film of an intragastrically soluble or enteric substance such as sugar, gelatin, hydroxypropyl cellulose and hydroxypropyl methylcellulose phthalate or may be coated with two or more layers. Capsule of a substance which can be absorbed such as gelatin is also included.

The liquid composition for oral administration includes pharmaceutically acceptable emulsion/suspension, solution, syrup, elixir, etc. In such a liquid composition, one or more active substance(s) is included in a commonly used inert diluent (such as pure water and ethanol). The composition may contain an adjuvant such as moisturizer and suspending agent, sweetener, flavor, aromatic agent and antiseptic agent besides the inert diluent.

Other composition for oral administration includes spray agent which contains one or more active substance(s) and is formulated by a known method per se. Besides the inert diluent, the composition may contain a stabilizer such as sodium hydrogen sulfite and a buffer giving isotonicity, e.g., isotonizing agent such as sodium chloride, sodium citrate, citric acid, etc. Method for the manufacture of spray agents is described, e.g., in U.S. Pat. No. 2,868,691 and No. 3,095,355 in detail.

Parenteral injection of the present invention includes aseptic aqueous and/or non-aqueous solution, suspension, and emulsion. Aqueous solution and suspension includes such as distilled water for injection and physiological saline solution. Non-aqueous solution and suspension includes such as propylene glycol, polyethylene glycol, vegetable oil such as olive oil, alcohol such as ethanol and Polysorbate 80 (Registered Trademark). It is also possible that aseptic and aqueous or non-aqueous solution, suspension and emulsion may be mixed and used. Such a composition may further contain adjuvants such as antiseptic, moisturizer, emulsifier, dispersing agent, stabilizer (such as lactose) and solubilizing agent (such as glutamic acid and aspartic acid). They are sterilized by, e.g., filtration passing through a bacteria-fixing filter, compounding of a disinfectant or irradiation. They may be also used in such a manner that, an aseptic solid composition is manufactured and, before using as a freeze-dried product for example, they are dissolved in sterilized or aseptic distilled water for injection or in other solvents.

An administration form of eye drop for parenteral administration includes eye drops, eye drops of a suspension type, eye drops of an emulsion type, eye drops which is dissolved upon actual use, and eye ointment.

Such eye drops may be manufactured according to a known method. For example, in the case of the eye drops, an isotonizing agent (sodium chloride, concentrated glycerol, etc.), a buffering agent (sodium phosphate, sodium acetate, etc.), a surfactant (Polysorbate 80 (trade name), polyoxyl stearate 40, polyoxyethylene hydrogenated castor oil, etc.), stabilizer (sodium citrate, sodium edentate, etc.), antiseptic agent (benzalkonium chloride, paraben, etc.), and the like are appropriately selected and prepared upon necessity. They are sterilized in the final step or prepared by an aseptic operation.

Inhalation agent for parenteral administration includes aerosol preparation, powder for inhalation and liquid for inhalation. The liquid for inhalation may be such a form that, the ingredient is dissolved or suspended in water or in other appropriate medium in actual use.

Those inhalation agents are prepared according to a known method. For example, in the case of liquid for inhalation, antiseptic agent (benzalkonium chloride, paraben, etc.), coloring agent, buffer (sodium phosphate, sodium acetate, etc.), isotonizing agent (sodium chloride, concentrated glycerol etc.), thickener (carboxyvinyl polymer, etc.), absorption promoter etc., are appropriately selected and prepared upon necessity.

In the case of powder for inhalation, lubricant (stearic acid, salt thereof, etc.), binder (starch, dextrin, etc.), excipient lactose, cellulose, etc.), coloring agent, antiseptic (benzalkonium chloride, paraben, etc.), absorption promoter, etc., are appropriately selected and prepared upon necessity.

In the administration of the liquid for inhalation, a spraying device (atomizer, nebulizer, etc.) are usually used and in the administration of the powder for inhalation, an administering device for inhalation of powdery pharmaceutical is usually used.

Other compositions for parenteral administration include outer solution, ointment, liniment, and suppository for intrarectal administration, and pessary for intravaginal administration etc., containing one or more active compound(s) which can be prepared by known methods.

Benefits of the Invention

Since the compounds of the present invention represented by formula (I) bind and antagonize to DP receptors, it is considered that the compounds are useful for prevention and/or treatment of diseases mediated by DP receptor such as allergic disease (e.g., allergic rhinitis, allergic conjunctivitis, atopic dermatitis, bronchial asthma, food allergy, etc.), systemic mastocytosis, disorders accompanied by systemic mast cell activation, anaphylaxis shock, bronchoconstriction, urticaria, eczema, pimples, allergic bronchial pulmonary aspergillosis, sinusitis, migraine, nasal polypus, anaphylactic vasculitis, eosinophilic syndrome, contact dermatitis, diseases accompanied by itch (such as atopic dermatitis, urticaria, allergic conjunctivitis, allergic rhinitis and contact dermatitis), diseases (e.g., cataract, retinal detachment, inflammation, infection, sleeping disorders, etc.) which are generated secondarily as a result of behavior accompanied by itch (scratching, beating, etc.), inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis, irritable bowel syndrome, interstitial cystitis, muscular dystrophy, polymyositis and multiple sclerosis. Further the compounds are considered to relate to sleeping and platelet aggregation and to be useful for these diseases.

BEST MODE FOR CARRYING OUT THE INVENTION

The following reference examples and examples illustrate the present invention, but do not limit the present invention.

The solvents in the parentheses show the developing or eluting solvents and the ratios of the solvents used are by volume in chromatographic separations or TLC. The solvents in the parentheses in NMR show the solvents for measurement.

The compound names represented in examples were named by ACD/Name (Version 6.00, Advanced Chemistry Development Inc.).

Example 1

4-methoxy-2,3-dimethylbenzoic acid 4-methoxy-2,3-dimethylbenzaldehyde(14.8 g) was dissolved in a mixed solvent of 2,2-dimethyl propanol (160 mL) and water (40 mL) and to the mixture, sodium dihydrogenphosphate dihydrate (15.5 g), 2-methyl-2-butene (43 mL), and sodium chlorite (28.5 g) were sequentially added, and the mixture was stirred for 2 hours at room temperature. Water and 1N hydrochloric acid were added to the reaction mixture, which was extracted with ethyl acetate. The organic layer was washed with saturated brine solution and was dried by anhydrous magnesium sulphate. The title compound (14.3 g) having the following physical data was obtained by allowing the residue obtained by removing the solvent to recrystallize from a mixed solvent of n-hexane and ethyl acetate.

TLC:Rf 0.52 (chloroform:methanol:acetate=9:1:0.1).

Example 2

4-hydroxy-2,3-dimethylbenzoic acid

Under argon atmosphere, to dichloromethane solution (50 mL) to which the compound (14.3 g) prepared in Example 1 was dissolved, boron tribromide dichloromethane solution (1M, 160 mL) was added, which was stirred overnight at room temperature. To the reaction mixture, water is added and the water layer of which the mixture was divided was extracted with ethyl acetate. To the extract, the organic layer was mixed and the mixture was washed with saturated brine solution and was dried by anhydrous magnesium sulphate. The title compound (13.2 g) having the following physical data was obtained by allowing the residue obtained by removing the solvent to recrystallize from the mixed solvent of n-hexane and ethyl acetate.

TLC:Rf 0.32 (chloroform:methanol:acetate=9:1:0.1).

Example 3 methyl 4-hydroxy-2,3-dimethylbenzoate

Under argon atmosphere, to anhydrous methanol (20 mL) to which thionylchloride (4.4 mL) was added at 0° C., a solution of the compound (5 g) prepared in Example 2 in anhydrous methanol (20 mL) was added. The reaction mixture was stirred for 2 hours at 65° C. and was cooled down to room temperature, which was concentrated. The title compound (2.36 g) having the following physical data was obtained by purifying the obtained residue by silica gel column chromatography (n-hexane:ethyl acetate=5:1).

TLC:Rf 0.29 (n-hexane:acetate=4:1).

Example 4

(2-fluorophenyl)methylamine

Under argon atmosphere, formate (6.1 mL) was dropped to acetic anhydride (15.5 mL) at 0° C., which was stirred for 2 hours at 50° C. After being cooled down to room temperature, the reaction mixture was diluted with tetrahydrofuran (THF; 10 mL). To the diluent, a solution of 2-fluoroaniline (5.56 g) in THF (20 mL) was added at room temperature and the mixture was stirred for 1 hour at room temperature. The obtained residue by which the reaction mixture was concentrated was dissolved to anhydrous THF (25 mL). Under argon atmosphere, to the anhydrous THF (25 mL) solution, borane tetrahydrofuran complex (1M THF solution; 125 mL) was added at 0° C. and the mixture was stirred for 2 hours at 50° C. After the reaction mixture was cooled down to room temperature, methanol (30 mL) and 4N hydrogen chloride dioxane solution (10 mL) were added on ice bath and the mixture was stirred for 1 hour at 60° C. The concentrated reaction mixture was added to 2N sodium hydroxide solution and was extracted with ethyl acetate. The organic layer was washed with saturated brine solution and was dried by anhydrous sodium sulfate. The solution was filtered with celite (trade name) and the filtrate was concentrated. To the residue, the mixed solvent (hexane:ethyl acetate=10:1) was added and was filtered on silicagel. The title compound (6.45 g) was obtained by concentrating the effluent.

Example 5

(2S)-3-((2-fluorophenyl)(methyl)amino)-1,2-propanediol

Under argon atmosphere, a mixture of the compound (1.24 g) prepared in Example 4, (R)-(+)-glycidol (1.11 g, aldrich, 98% ee), and ethanol (1 mL) was stirred for 12 hours at 50° C. The title compound having the following physical data was obtained by concentrating the reaction mixture. The obtained title compound was used for the following reaction in no purification.
TLC:Rf 0.40 (n-hexane:ethyl acetate=1:1).

Example 6

((2S)-4-methyl-3,4-dihydro-2H-1,4-benzoxazin-2-yl)methanol

To a solution of the compound prepared in Example 5 in anhydrous dimethylformamide (DMF; 10 mL), potassium t-butoxide (1.68 g) was added, and the mixture was stirred for 3 hours at 80° C. The reaction mixture was added to water, which was extracted with ethyl acetate. The organic layer was washed with saturated brine solution and was dried by anhydrous sodium sulfate. The solution was filtered with celite (trade name) and was concentrated. The title compound (1.55 g, 97.6% ee) having the following physical data was obtained by purifying the residue with silica gel column chromatography (hexane:ethyl acetate=3:1).
TLC:Rf 0.35 (n-hexane:ethyl acetate=2:1).
The optical purity of the title compound was decided by using high performance liquid chromatography (HPLC).
Column: CHIRALCEL OD (Daicel Chemical Industries, Ltd.), 0.46 cmφ×25 cm
Flow rate: 1 mL/minute
Solvent:hexane: 2-propanol=93:7
Detection wave-length: 254 nm
Retention time: 30.70 minutes
Temperature: 24° C.

Example 7

((2S)-4-methyl-3,4-dihydro-2H-1,4-benzoxazin-2-yl)methyl 4-methylbenzenesulfonate Under argon atmosphere, to a solution of the compound (3.06 g) prepared in Example 6 in tetrahydrofuran (9 mL), triethylamine (5 mL) was added. To the reaction solution, a solution of p-toluenesulfonic acid chloride (3.42 g) in tetrahydrofuran (9 mL) and N,N-dimethylaminopyridine (209 mg) were added and the mixture was stirred for 4 hours at room temperature. After adding water, the reaction solution was extracted by tert-butylmethyl ether. The extract was solidified by adding isopropyl alcohol to the residue obtained by concentrating the organic layer. The title compound (5.12 g) having the following physical data was obtained by washing the filtered solid with isopropyl alcohol and drying.
TLC:Rf 0.81 (n-hexane:ethyl acetate=1:1).

Example 8 methyl 2,3-dimethyl-4-(((2S)-4-methyl-3,4-dihydro-2H-1,4-benzoxazin-2-yl)methoxy)benzoate Under argon atmosphere, to anhydrous N,N-dimethylformamide (40 mL) solution to which the compound (2.05 g) prepared in Example 3 was dissolved, cesium carbonate (7.82 g) and the compound (4.0 g) prepared in Example 7 was sequentially added. The reaction mixture was stirred for 4 hours at 75° C. After being cooled down to room temperature, water was added to the reaction mixture, which was extracted with ethyl acetate. The organic layer was washed with water and saturated brine solution and was dried by anhydrous magnesium sulphate. The title compound (3.89 g) having the following physical data was obtained by purifying the residue obtained by removing the solvent by silica gel column chromatography (n-hexane:ethyl acetate=4:1).
TLC:Rf 0.73 (n-hexane:ethyl acetate=2:1).

Example 9

2,3-dimethyl-4-(((2S)-4-methyl-3,4-dihydro-2H-1,4-benzoxazin-2-yl)methoxy)benzoic acid To the compound (3.85 g) prepared in Example 8, 1,2-dimethoxyethane (40 mL), methanol (40 mL), and 1N sodium hydroxide solution (30 mL) were added. The reaction mixture was carbonized overnight at 67° C. After being cooled down to room temperature, methyl tert-butyl ether was added to the reaction mixture. After being extracted by 1N sodium hydroxide solution, the water layer was neutralized with 5N hydrochloric acid. The water layer was extracted with ethyl acetate and the organic layer was washed with water and saturated brine solution and was dried by anhydrous magnesium sulphate. The title compound (3.70 g) having the following physical data was obtained by allowing the residue obtained by removing the solvent to recrystallize from the mixed solvent of n-hexane and ethyl acetate.
TLC:Rf 0.24 (n-hexane:ethyl acetate=2:1).

Example 10

2,3-dimethyl-4-(((2S)-4-methyl-3,4-dihydro-2H-1,4-benzoxazin-2-yl)methoxy)benzoylchloride Under argon atmosphere, the compound (400 mg) prepared in Example 9 was dissolved to 1,2-dimethoxyethane (6.0 mL). Anhydrous N,N-dimethylformamide (one drop) and oxalyl chloride (0.22 mL) were added to the reaction mixture, which was stirred for 30 minutes at 40° C. The title compound was obtained by concentrating the reaction mixture.

Example 11 methyl(3-amino-4-fluorophenyl)acetate

A mixture of 4-fluoro-2-nitrobenzoic acid (23.1 g), oxalyl chloride (16 mL), N,N-dimethylformamide (0.10 mL), and 1,2-dimethoxyethane (250 mL) was stirred for 1 hour at room temperature. The acid chloride was obtained by concentrating the reaction mixture.

To a solution (2.0 M, 75 mL) of trimethylsilyldiazomethane in n-hexane and a solution of triethylamine (35 mL) in tetrahydrofuran (100 mL), a solution of the previous acid chloride in tetrahydrofuran (250 mL) was dropped and was stirred for 1 hour at room temperature. The reaction mixture was diluted with ethyl acetate and the extracted solid was separated. Water was added to the filtrate, which was extracted with ethyl acetate. The organic layer was washed with water and saturated brine solution and was dried by anhydrous magnesium sulphate. The diazoketone was obtained by removing the solvent.

To a solution (250 mL) of the diazo ketone and triethylamine (15.7 mL) in ethanol, silver acetate (2.09 g) was added at room temperature, the mixture was stirred during for 30 minutes at room temperature and for 30 minutes at 66° C. In addition, silver acetate (2.09 g) was added and was stirred for 30 minutes at 66° C. After being cooled down to room temperature, ethyl acetate and water were added to the reaction mixture, which was filtered with celite (trade name). The organic layer that was separated from the filtrate was washed with water and saturated brine solution and was dried by anhydrous magnesium sulphate.

Ethyl ester (15.3 g) was obtained by purifying the residue obtained by removing the solvent by silica gel column chromatography (n-hexane:ethyl acetate=8:1→ethyl acetate). A solution (135 mL) of the ethyl ester and iron (18.8 g) in acetic acid was stirred for 1 hour half at 60° C. The reaction mixture was diluted with the toluene and was filtered with celite (trade name). The filtrate was washed with water and saturated brine solution, and was dried by anhydrous magnesium sulphate. The title compound (10.4 g) having the following physical data was obtained by removing the solvent.

TLC:Rf 0.69 (n-hexane:ethyl acetate=2:1).

Example 12 methyl(3-((2,3-dimethyl-4-(((2S)-4-methyl-3,4-dihydro-2H-1,4-benzoxazin-2-yl)methoxy)benzoyl)amino)-4-fluorophenyl)acetate To a solution (1.0 mL) of the compound (135 mg) prepared in Example 11 in dichloromethane, pyridine (0.10 mL) and a solution (1.5 mL) of the compound (210 mg) prepared in Example 10 in dichloromethane were sequentially added. The reaction mixture was stirred for 30 minutes at room temperature. 1N hydrochloric acid (3.0 mL) and water were added to the reaction mixture, which was extracted with ethyl acetate. The organic layer was washed with water and saturated brine solution and was dried by anhydrous magnesium sulphate. The title compound (250 mg) having the following physical data was obtained by purifying the residue obtained by removing the solvent by silica gel column chromatography (n-hexane:ethyl acetate=3:1).

TLC:Rf 0.44 (n-hexane:ethyl acetate=2:1).

Example 13

(3-((2,3-dimethyl-4-(((2S)-4-methyl-3,4-dihydro-2H-1,4-benzoxazin-2-yl)methoxy)benzoyl)amino)-4-fluorophenyl)acetic acid

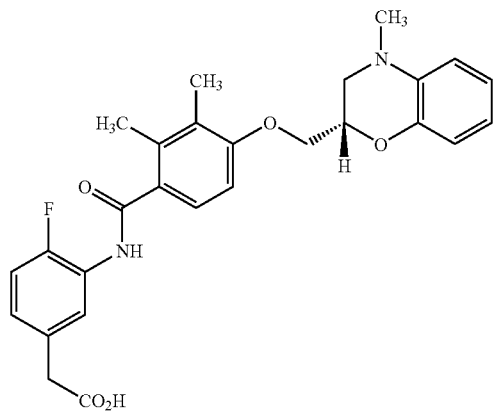

To a mixture of the compound (240 mg) prepared in Example 12, 1,2-dimethoxyethane (5.0 mL), and methanol (5.0 mL), 1N sodium hydroxide solution (3.0 mL) was added, and the mixture was stirred for 1 hour at room temperature. Methyl tert-butylmethyl ether was added to the reaction mixture, which was extracted by 1N sodium hydroxide solution. The water layer was neutralized by adding 5N hydrochloric acid and was extracted with ethyl acetate. The organic layer was washed with water and saturated brine solution, and was dried by anhydrous magnesium sulphate. The compound (208 mg) of the present invention having the following physical data was obtained by allowing the residue obtained by removing the solvent to recrystallize from a mixed solvent of n-hexane, ethyl acetate, and tetrahydrofuran.

Property: crystal;

TLC:Rf 0.53 (chloroform:methanol:acetate=9:1:0.1);

$^1$H-NMR: (DMSO-$d_6$) δ 2.16, 2.29, 2.85, 3.22, 3.40, 3.57, 4.22, 4.60, 6.59, 6.76, 6.94, 7.10, 7.19, 7.29, 7.57, 9.88, 12.35.

Example 13(1)-Example 13(31)

The compounds of the present invention having the following physical data were obtained by the same procedures as Example 12→Example 13 using a corresponding acid chloride instead of the compound prepared in Example 10, or using a corresponding amine instead of the compound prepared in Example 11.

Example 13(1)

(4-chloro-3-(2,3-dimethyl-4-(((2S)-4-methyl-3,4-dihydro-2H-1,4-benzoxazin-2-yl)methoxy)benzoyl)amino)phenyl)acetic acid Property: crystal;

TLC:Rf 0.40 (n-hexane:ethyl acetate:acetic acid=50:50:1);

$^1$H-NMR: (CDCl$_3$) δ 2.23, 2.43, 2.92, 3.29, 3.42, 3.70, 4.16, 4.27, 4.67, 6.69, 6.85, 7.02, 7.36, 7.94, 8.52.

Example 13(2)

(4-chloro-3-((2,6-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.54 (chloroform:methanol=9:1);
$^1$H-NMR: (CDCl$_3$) δ 2.38, 2.91, 3.24, 3.39, 3.72, 4.12, 4.24, 4.63, 6.69, 6.86, 7.05, 7.37, 7.74, 8.50.

Example 13(3)

(4-chloro-3-((5-chloro-2-fluoro-4-(((2S)-4-methyl-3,4-dihydro-2H-1,4-benzoxazin-2-yl)methoxy)benzoyl)amino)phenyl)acetic acid TLC:Rf 0.54 (chloroform:methanol:acetic acid=9:1:0.1);
$^1$H-NMR: (DMSO-d$_6$) δ 2.84, 3.22, 3.39, 3.61, 4.41, 4.63, 6.59, 6.77, 7.16, 7.37, 7.48, 7.71, 7.84, 9.82, 12.42.

Example 13(4)

(4-chloro-3-((2,5-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.29 (chloroform:methanol=9:1);
$^1$H-NMR: (DMSO-d$_6$) δ 2.18, 2.42, 2.85, 3.22, 3.38, 3.58, 4.22, 4.59, 6.58, 6.70, 6.78, 6.87, 7.12, 7.38, 7.41, 7.54, 9.61, 12.36.

Example 13(5)

(4-chloro-3-((2-fluoro-5-methyl-4-(((2S)-4-methyl-3,4-dihydro-2H-1,4-benzoxazin-2-yl)methoxy)benzoyl)amino)phenyl)acetic acid Property: crystal;
TLC:Rf 0.49 (chloroform:methanol:acetic acid=9:1:0.1);
$^1$H-NMR: (DMSO-d$_6$) δ 2.18, 2.85, 3.21, 3.41, 3.60, 4.30, 4.61, 6.60, 6.76, 7.11, 7.47, 7.64, 7.81, 9.57.

Example 13(6)

(4-chloro-3-((2,5-difluoro-4-(((2S)-4-methyl-3,4-dihydro-2H-1,4-benzoxazin-2-yl)methoxy)benzoyl)amino)phenyl)acetic acid Property: crystal;
TLC:Rf 0.44 (chloroform:methanol:acetic acid=9:1:0.1);
$^1$H-NMR: (DMSO-d$_6$) δ 2.84, 3.17, 3.38, 3.61, 4.38, 4.62, 6.60, 6.76, 7.15, 7.39, 7.48, 7.65, 7.74, 9.75, 12.42.

Example 13(7)

(3-((2,3-dimethyl-4-(((2S)-4-methyl-3,4-dihydro-2H-1,4-benzoxazin-2-yl)methoxy)benzoyl)amino)-4-methylphenyl)acetic acid Property: crystal;
TLC:Rf 0.43 (chloroform:methanol:acetic acid=9:1:0.1);
$^1$H-NMR: (DMSO-d$_6$) δ 2.16, 2.22, 2.32, 2.85, 3.22, 3.40, 3.52, 4.21, 4.60, 6.59, 6.77, 6.99, 7.17, 7.30, 9.59, 12.28.

Example 13(8)

(3-((2,3-dimethyl-4-(((2S)-4-methyl-3,4-dihydro-2H-1,4-benzoxazin-2-yl)methoxy)benzoyl)amino)-5-methylphenyl)acetic acid Property: crystal;
TLC:Rf 0.55 (chloroform:methanol:acetic acid=9:1:0.1);
$^1$H-NMR: (DMSO-d$_6$) δ 2.15, 2.26, 2.84, 3.22, 3.40, 3.47, 4.21, 4.59, 6.59, 6.76, 6.93, 7.23, 7.44, 10.08, 12.29.

Example 13(9)

(3-((2,3-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.42 (chloroform:methanol:acetic acid=9:1:0.1);
$^1$H-NMR: (DMSO-d$_6$) δ 2.16, 2.26, 2.84, 3.22, 3.40, 3.52, 4.22, 4.59, 6.59, 6.76, 6.95, 7.25, 7.56, 7.68, 10.15, 12.30.

Example 13(10)

(3-((2,6-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.53 (chloroform:methanol:acetic acid=9:1:0.1);
$^1$H-NMR: (DMSO-d$_6$) δ 2.24, 2.83, 3.16, 3.35, 3.53, 4.18, 4.56, 6.59, 6.76, 6.96, 7.25, 7.55, 7.67, 10.25, 12.31.

Example 13(11)

(3-((2,6-dimethyl-4-(((2S)-4-methyl-3,4-dihydro-2H-1,4-benzoxazin-2-yl)methoxy)benzoyl)amino)-5-methylphenyl)acetic acid Property: crystal;
TLC:Rf 0.33 (chloroform:methanol:acetic acid=9:1:0.1);
$^1$H-NMR: (DMSO-d$_6$) δ 2.24, 2.83, 3.16, 3.36, 3.47, 4.17, 4.55, 6.59, 6.75, 7.43, 10.17, 12.28.

Example 13(12)

(5-((2,6-dimethyl-4-(((2S)-4-methyl-3,4-dihydro-2H-1,4-benzoxazin-2-yl)methoxy)benzoyl)amino)-2-fluorophenyl)acetic acid Property: crystal;
TLC:Rf 0.55 (chloroform:methanol:acetic acid=9:1:0.1);
$^1$H-NMR: (DMSO-d$_6$) δ 2.23, 2.83, 3.16, 3.36, 3.58, 4.18, 4.55, 6.59, 6.75, 7.13, 7.56, 7.72, 10.29.

Example 13(13)

(5-(2,5-dimethyl-4-(((2S)-4-methyl-3,4-dihydro-2H-1,4-benzoxazin-2-yl)methoxy)benzoyl)amino)-2-methylphenyl)acetic acid Property: crystal;
TLC:Rf 0.36 (n-hexane:ethyl acetate:acetic acid=50:50:1);
$^1$H-NMR: (DMSO-d$_6$) δ 2.17, 2.19, 2.35, 2.84, 3.21, 3.39, 3.52, 4.23, 4.59, 6.59, 6.72, 6.79, 6.90, 7.09, 7.28, 7.47, 7.56, 9.99.

Example 13(14)

(5-((2,5-dimethyl-4-(((2S)-4-methyl-3,4-dihydro-2H-1,4-benzoxazin-2-yl)methoxy)benzoyl)amino)-2-fluorophenyl)acetic acid Property: crystal;
TLC:Rf 0.37 (n-hexane:ethyl acetate:acetic acid=50:50:1);
$^1$H-NMR: (DMSO-d$_6$) δ 2.18, 2.36, 2.84, 3.21, 3.39, 3.57, 4.23, 4.59, 6.59, 6.72, 6.79, 6.91, 7.12, 7.30, 7.58, 7.71, 10.12.

Example 13(15)

(3-((2,5-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.60 (chloroform:methanol=9:1);
$^1$H-NMR: (DMSO-d$_6$) δ 2.18, 2.36, 2.84, 3.21, 3.39, 3.51, 4.23, 4.59, 6.59, 6.72, 6.79, 6.94, 7.24, 7.29, 7.57, 7.66, 10.08.

Example 13(16)

(5-((2,3-dimethyl-4-(((2S)-4-methyl-3,4-dihydro-2H-1,4-benzoxazin-2-yl)methoxy)benzoyl)amino)-2-fluorophenyl)acetic acid Property: crystal;
TLC:Rf 0.41 (chloroform:methanol:acetic acid=9:1:0.1);
$^1$H-NMR: (DMSO-d$_6$) δ 2.16, 2.26, 2.84, 3.22, 3.40, 3.59, 4.21, 4.59, 6.59, 6.76, 6.94, 7.13, 7.25, 7.57, 7.73, 10.20, 12.46.

Example 13(17)

(5-((2,3-dimethyl-4-(((2S)-4-methyl-3,4-dihydro-2H-1,4-benzoxazin-2-yl)methoxy)benzoyl)amino)-2-methylphenyl)acetic acid Property: crystal;
TLC:Rf 0.50 (chloroform:methanol:acetic acid=9:1:0.1);
$^1$H-NMR: (DMSO-d$_6$) δ 2.15, 2.18, 2.26, 2.84, 3.21, 3.40, 3.52, 4.21, 4.59, 6.59, 6.77, 6.93, 7.09, 7.23, 7.47, 7.57, 10.06.

Example 13(18)

(5-((2,6-dimethyl-4-(((2S)-4-methyl-3,4-dihydro-2H-1,4-benzoxazin-2-yl)methoxy)benzoyl)amino)-2-methylphenyl)acetic acid Property: crystal;
TLC:Rf 0.50 (chloroform:methanol:acetic acid=9:1:0.1);
$^1$H-NMR: (DMSO-d$_6$) δ 2.18, 2.23, 2.83, 3.16, 3.36, 3.52, 4.17, 4.55, 6.59, 6.76, 7.09, 7.46, 7.56, 10.14.

Example 13(19)

(3-((2,6-dimethyl-4-(((2S)-4-methyl-3,4-dihydro-2H-1,4-benzoxazin-2-yl)methoxy)benzoyl)amino)-4-methylphenyl)acetic acid Property: crystal;
TLC:Rf 0.46 (chloroform:methanol:acetic acid=9:1:0.1);
$^1$H-NMR: (DMSO-d$_6$) δ 2.24, 2.32, 2.84, 3.16, 3.36, 3.52, 4.18, 4.56, 6.59, 6.76, 7.02, 7.17, 7.28, 9.71.

Example 13(20)

(3-((2,6-dimethyl-4-(((2S)-4-methyl-3,4-dihydro-2H-1,4-benzoxazin-2-yl)methoxy)benzoyl)amino)-4-fluorophenyl)acetic acid Property: crystal;
TLC:Rf 0.43 (chloroform:methanol:acetic acid=9:1:0.1);
$^1$H-NMR: (DMSO-d$_6$) δ 2.28, 2.83, 3.16, 3.36, 3.56, 4.18, 4.56, 6.59, 6.76, 7.14, 7.54, 10.02.

Example 13(21)

(3-((2,5-dimethyl-4-(((2S)-4-methyl-3,4-dihydro-2H-1,4-benzoxazin-2-yl)methoxy)benzoyl)amino)-4-fluorophenyl)acetic acid Property: crystal;
TLC:Rf 0.47 (chloroform:methanol=9:1);
$^1$H-NMR: (DMSO-d$_6$) δ 2.17, 2.38, 2.84, 3.21, 3.39, 3.56, 4.23, 4.59, 6.59, 6.72, 6.79, 6.91, 7.09, 7.18, 7.35, 7.54, 9.81.

Example 13(22)

(3-((2,5-dimethyl-4-(((2S)-4-methyl-3,4-dihydro-2H-1,4-benzoxazin-2-yl)methoxy)benzoyl)amino)-4-methylphenyl)acetic acid Property: crystal;
TLC:Rf 0.62 (chloroform:methanol=9:1);
$^1$H-NMR: (DMSO-d$_6$) δ 2.18, 2.21, 2.40, 2.84, 3.21, 3.39, 3.51, 4.23, 4.59, 6.60, 6.72, 6.79, 6.91, 7.01, 7.16, 7.25, 7.35, 9.55.

Example 13(23)

(3-((2,5-dimethyl-4-(((2S)-4-methyl-3,4-dihydro-2H-1,4-benzoxazin-2-yl)methoxy)benzoyl)amino)-5-methylphenyl)acetic acid Property: crystal;
TLC:Rf 0.47 (chloroform:methanol=9:1);
$^1$H-NMR: (DMSO-d$_6$) δ 2.17, 2.26, 2.35, 2.84, 3.21, 3.39, 3.46, 4.23, 4.59, 6.61, 6.76, 6.91, 7.28, 7.43, 10.00.

Example 13(24)

(4-chloro-3-((4-((2R)-2,3-dihydro-1,4-benzodioxin-2-ylmethoxy)-2,6-dimethylbenzoyl)amino)phenyl)acetic acid Property: crystal;
TLC:Rf 0.46 (chloroform:methanol=9:1);
$^1$H-NMR: (CDCl$_3$) δ 2.39, 3.73, 4.21, 4.40, 4.57, 6.66, 6.88, 7.06, 7.37, 7.73, 8.51.

Example 13(25)

(2-chloro-5-((2,3-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.46 (chloroform:methanol:acetic acid=9:1:0.1);
$^1$H-NMR: (DMSO-d$_6$) δ 2.16, 2.26, 2.84, 3.22, 3.40, 3.67, 4.22, 4.59, 6.59, 6.76, 6.95, 7.26, 7.37, 7.61, 7.80, 10.29, 12.46.

Example 13(26)

(2-chloro-5-((2,6-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.39 (n-hexane:ethyl acetate:acetic acid=66:33:1);
$^1$H-NMR: (DMSO-d$_6$) δ 2.23, 2.83, 3.16, 3.36, 3.67, 4.18, 4.55, 6.59, 6.75, 7.38, 7.60, 7.79, 10.39.

Example 13(27)

(2-chloro-5-((2,5-dimethyl-4-(((2S)-4-methyl-3,4-dihydro-2H-1,4-benzoxazin-2-yl)methoxy)benzoyl)amino)phenyl)acetic acid Property: crystal;
TLC:Rf 0.42 (n-hexane:ethyl acetate:acetic acid=66:33:1);
$^1$H-NMR: (DMSO-d$_6$) δ 2.18, 2.36, 2.84, 3.21, 3.39, 3.66, 4.24, 4.59, 6.59, 6.72, 6.79, 6.92, 7.31, 7.37, 7.61, 7.79, 10.21.

Example 13(28)

(4-chloro-3-((4-((3R)-2,3-dihydro-1-benzofuran-3-ylmethoxy)-2,6-dimethylbenzoyl)amino)phenyl)acetic acid Property: crystal;
TLC:Rf 0.39 (chloroform:methanol=9:1);
$^1$H-NMR: (CDCl$_3$) δ 2.38, 3.72, 3.92, 4.02, 4.16, 4.51, 4.71, 6.63, 6.84, 6.89, 7.05, 7.18, 7.30, 7.37, 7.73, 8.51.

Example 13(29)

(4-chloro-3-((2,6-dimethyl-4-(((3R)-5-methyl-2,3-dihydro-1-benzofuran-3-yl)methoxy)benzoyl)amino)phenyl)acetic acid Property: crystal;
TLC:Rf 0.39 (chloroform:methanol=9:1);
$^1$H-NMR: (CDCl$_3$) δ 2.30, 2.38, 3.73, 3.88, 3.99, 4.16, 4.50, 4.69, 6.63, 6.73, 6.98, 7.05, 7.09, 7.37, 7.73, 8.52.

Example 13(30)

(4-chloro-3-((4-((2S)-2,3-dihydro-1-benzofuran-2-ylmethoxy)-2,6-dimethylbenzoyl)amino)phenyl)acetic acid Property: crystal;
TLC:Rf 0.40 (chloroform:methanol=9:1);
$^1$H-NMR: (CDCl$_3$) δ 2.38, 3.13, 3.40, 3.73, 4.10, 4.22, 5.15, 6.65, 6.85, 7.05, 7.17, 7.37, 7.73, 8.51.

Example 13(31)

(3-((4-(1,3-benzodioxol-2-ylmethoxy)-2,6-dimethylbenzoyl)amino)-4-chlorophenyl)acetic acid Property: crystal;
TLC:Rf 0.39 (chloroform:methanol=9:1);
$^1$H-NMR: (CDCl$_3$) δ 2.38, 3.72, 4.27, 6.44, 6.66, 6.85, 7.05, 7.37, 7.73, 8.50.

Example 14 methyl 2-(4-chloro-3-nitrophenyl)propanoate

Under argon atmosphere, to a solution (14 mL) of methyl (4-chloro-3-nitrophenyl)acetate (300 mg) in tetrahydrofuran, methyl iodide (0.26 mL), lithium N,N-diisopropyl amidocyclohexane solution (1.5M, 2.32 mL) were dropped at −78° C. The reaction mixture was stirred for 2 hours with rising temperature up to room temperature. Water was added to the reaction mixture, which was extracted with ethyl acetate. The organic layer was sequentially washed with diluted hydrochloric acid, water, and saturated brine solution, and was dried by anhydrous magnesium sulphate. The title compound (245 mg) having the following physical data was obtained by purifying the residue obtained by removing the solvent by silica gel column chromatography (n-hexane:ethyl acetate=5:1).
TLC:Rf 0.37 (n-hexane:ethyl acetate=4:1).

Example 15 methyl 2-(4-chloro-3-nitrophenyl)-2-methylpropanoate

Under argon atmosphere, to a solution (5 mL) of the compound prepared in Example 14 in tetrahydrofuran, methyl iodide (0.01 mL) and lithium N,N-diisopropyl amidocyclohexane solution (1.5M, 0.83 mL) were dropped at −78° C. The reaction mixture was stirred for 2 hours with rising temperature up to room temperature. Water was added to the reaction mixture, which was extracted with ethyl acetate. The organic layer was sequentially washed with diluted hydrochloric acid, water, and saturated brine solution, and was dried by anhydrous magnesium sulphate. The title compound (118 mg) having the following physical data was obtained by purifying the residue obtained by removing the solvent by silica gel column chromatography (n-hexane:ethyl acetate=8:1).
TLC:Rf 0.42 (n-hexane:ethyl acetate=4:1).

Example 16 methyl 2-(3-amino-4-chlorophenyl)-2-methylpropanoate

The compound (116 mg) prepared in Example 15 was dissolved to a mixed solvent of acetate (2.5 mL) and water (0.5 mL). Iron filings (133 mg) was added to the reaction mixture that was warmed up to 80° C., which was stirred for 30 minutes. Water was added to the reaction mixture, which was extracted with ethyl acetate. The organic layer was sequentially washed with saturated sodium hydrogencarbonate solution, water, and saturated brine solution, and was dried by anhydrous magnesium sulphate. The title compound (102 mg) having the following physical data was obtained by removing the solvent.
TLC:Rf 0.26 (n-hexane:ethyl acetate=4:1).

Example 17

2-chloro-4-(((2S)-4-methyl-3,4-dihydro-2H-1,4-benzoxazin-2-yl)methoxy)benzoylchloride Under argon atmosphere, oxalylchloride (0.3 mL) and N,N-dimethylformamide (1 drop) were added to a solution (4.5 mL) of 2-chloro-4-(((2S)-4-methyl-3,4-dihydro-2H-1,4- benzoxazin-2-yl)methoxy)benzoic acid (488 mg: the compound produced by the same procedures as a series of Example 8→Example 9→Example 10 using methyl 4-hydroxy-2-chlorobenzoate instead of the compound produced in Example 3.) in 1,2-dimethoxyethane, which was stirred for 1 hour at 40° C. The title compound was obtained by concentrating the reaction mixture.

Example 18 methyl 2-(4-chloro-3-((2-chloro-4-(((2S)-4-methyl-3,4-dihydro-2H-1,4-benzoxazin-2-yl)methoxy)benzoyl)amino)phenyl)-2-methylpropanoate A solution of the compound prepared in Example 17 in dichloromethane (1.8 mL) was dropped to a solution of the compound (100 mg) prepared in Example 16 in dichloromethane (1.8 mL). Pyridine (0.057 mL) was added to the reaction mixture, which was stirred for 1 hour at room temperature. The reaction mixture dissolved to water was extracted with ethyl acetate. The organic layer was sequentially washed with diluted hydrochloric acid, saturated sodium hydrogencarbonate solution, and saturated brine solution and was dried by anhydrous magnesium sulphate. The title compound (164 mg) having the following physical data was obtained by purifying the residue obtained by removing the solvent by silica gel column chromatography (n-hexane:ethyl acetate=4:1).
TLC:Rf0.41 (n-hexane:ethyl acetate=2:1).

Example 19

2-(4-chloro-3-((2-chloro-4-(((2S)-4-methyl-3,4-dihydro-2H-1,4-benzoxazin-2-yl)methoxy)benzoyl)amino)phenyl)-2-methylpropanoic acid

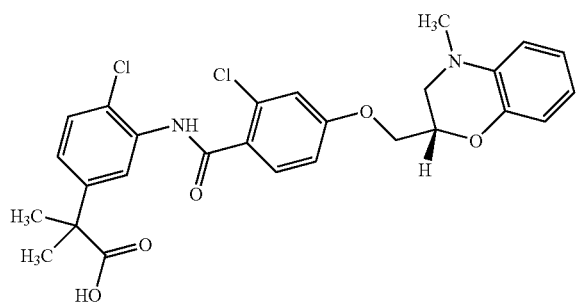

To a mixture of the compound (162 mg) prepared in Example 18, tetrahydrofuran (1.5 mL), and methanol (1.5 mL), 1N sodium hydroxide solution (0.6 mL) was added, and the mixture was stirred for 4 hours at 50° C. In addition, 2N sodium hydroxide solution (0.6 mL) was added to it, which was stirred for 3 hours at 50° C. The reaction mixture was neutralized by adding 2N hydrochloric acid (0.6 mL) and was extracted with ethyl acetate after adding water. The organic layer was washed with saturated brine solution and was dried by anhydrous magnesium sulphate. The compound (124 mg) of the present invention having the following physical data was obtained by purifying the residue obtained by removing the solvent by silica gel column chromatography (methylene chloride:ethyl acetate=9:1→4:1).
Property: amorphous;
TLC:Rf 0.26 (n-hexane:ethyl acetate=1:1);
$^1$H-NMR: (CDCl$_3$) δ1.64, 2.91, 3.25, 3.38, 4.18, 4.27, 4.66, 6.71, 6.87, 6.96, 7.04, 7.11, 7.36, 7.88, 8.71.

Example 20

(4-chloro-3-nitrophenyl)((trimethylsilyl)oxy)acetonitrile

To a mixture of 4-chloro-3-nitrobenzaldehyde (3.71 g), zinc iodide (128 mg), and dichloromethane (50 mL), trimethylsilylcyanide (2.9 mL) was added at ice-cold temperature and the mixture was stirred for 1 hour at the same temperature. 1N hydrochloric acid was added to the reaction mixture, which was extracted with ethyl acetate. The organic layer was washed with water and saturated brine solution and was dried by anhydrous magnesium sulphate. The title compound (5.95 g) having the following physical data was obtained by removing the solvent.
TLC:Rf 0.55 (n-hexane:ethyl acetate=4:1).

Example 21

(4-chloro-3-nitrophenyl)(hydroxy)acetic acid

Concentrated hydrochloric acid (30 mL) was added to a solution of the compound (5.95 g) prepared in Example 20 in acetate (30 mL), which was stirred overnight at 90° C. The reaction mixture was soaked in ice after being cooled and was extracted with ethyl acetate. The organic layer was washed with water and saturated brine solution and was dried by anhydrous magnesium sulphate. The title compound (4.48 g) having the following physical data was obtained by removing the solvent.
TLC:Rf 0.14 (n-hexane:ethyl acetate=1:1).

Example 22 ethyl(4-chloro-3-nitrophenyl)(hydroxy)acetate

P-toluenesulfonic acid (367 mg) was added to a solution (50 mL) of the compound (4.48 g) prepared in Example 21 in ethanol, which was stirred for 4 hours at 70° C. The reaction mixture was cooled and was extracted with ethyl acetate after adding water. The organic layer was washed with water and saturated brine solution and was dried by anhydrous magnesium sulphate. The title compound (4.83 g) having the following physical data was obtained by removing the solvent.
TLC:Rf 0.37 (n-hexane:ethyl acetate=2:1).

Example 23 ethyl(4-chloro-3-nitrophenyl)(oxo)acetate

To a solution (10 mL) of the compound (1.59 g) prepared in Example 22 in acetic acid, 10% sodium hypochlorite solution (6.78 g) was added at ice-cold temperature, and was stirred for 1 hour at the same temperature. Acetate (10 mL) and 10% sodium hypochlorite solution (6.78 g) were added to the reaction mixture, and further acetate (10 mL) and 10% sodium hypochlorite solution (6.78 g) were added, and the mixture was stirred for 2 hours. Water was added to the reaction mixture, which was extracted with ethyl acetate. The organic layer was washed with water and saturated brine solution and was dried by anhydrous magnesium sulphate. The title compound (414 mg) having the following physical data was obtained by purifying the residue obtained by removing the solvent by silica gel column chromatography (n-hexane:ethyl acetate=4:1).

TLC:Rf 0.59 (n-hexane:ethyl acetate=2:1).

Example 24 ethyl(4-chloro-3-nitrophenyl)(difluoro)acetate

Under argon atmosphere, diethylaminosulfatrifluoride (DAST)(311 mg) was added to a solution (5 mL) of the compound (414 mg) prepared in Example 23 in dichloromethane at ice-cold temperature, which was stirred for 2 hours at room temperature and then for 2 hours at 45° C. Water was added to the reaction mixture, which was extracted with ethyl acetate. The organic layer was sequentially washed with saturated sodium hydrogencarbonate solution, water, and saturated brine solution and was dried by anhydrous magnesium sulphate. The title compound (278 mg) having the following physical data was obtained by purifying by (n-hexane:ethyl acetate=9:7).

TLC:Rf 0.57 (n-hexane:ethyl acetate=4:1).

Example 25 ethyl(3-amino-4-chloro)(difluoro)acetate

The compound (253 mg) prepared in Example 24 was dissolved to the mixed solvent of acetate (3 mL) and water (0.3 mL). Iron filings (253 mg) was added to the reaction mixture at 80° C., which was stirred for 30 minutes at the same temperature. The reaction mixture was soaked in ice and was extracted with mixed solvent (1:1) of n-hexane and ethyl acetate. The organic layer was washed with water and saturated brine solution and was dried by anhydrous magnesium sulphate. The title compound (194 mg) having the following physical data was obtained by removing the solvent.

TLC:Rf 0.48 (n-hexane:ethyl acetate=4:1).

Example 26 ethyl(4-chloro-3-((2-chloro-4-(((2S)-4-methyl-3,4-dihydro-2H-1,4-benzoxazin-2-yl)methoxy)benzoyl)amino)phenyl)(difluoro)acetate Under argon atmosphere, to a mixture of the compound (180 mg) prepared in Example 25, pyridine (0.5 mL), and dichloromethane (1 mL), a solution (4 mL) of the compound (303 mg) prepared in Example 17 in dichloromethane was dropped at ice-cold temperature, and the mixture was stirred overnight at room temperature. 1N hydrochloric acid was added to the reaction mixture, which was extracted with ethyl acetate. The organic layer was washed with water and saturated brine solution and was dried by anhydrous magnesium sulphate. The title compound (207 mg) having the following physical data was obtained by purifying the residue obtained by removing the solvent by silica gel column chromatography (n-hexane:ethyl acetate=4:1→3:1).

TLC:Rf 0.55 (n-hexane:ethyl acetate=2:1).

Example 27

(4-chloro-3-((2-chloro-4-(((2S)-4-methyl-3,4-dihydro-2H-1,4-benzoxazin-2-yl)methoxy)benzoyl)amino)phenyl)(difluoro)acetate

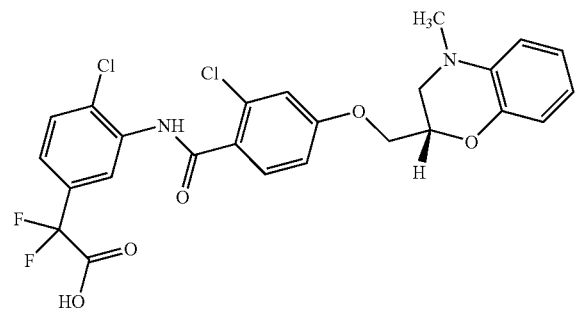

To a mixture of the compound (207 mg) prepared in Example 26, ethanol (4 mL), and tetrahydrofuran (2 mL), 1N sodium hydroxide solution (1 mL) was added and the mixture was stirred for 2 hours at room temperature. After being neutralized by adding 1N hydrochloric acid, the reaction mixture was extracted with ethyl acetate. The organic layer was washed with water and saturated brine solution and was dried by anhydrous magnesium sulphate. The residue obtained by removing the solvent was purified by silica gel column chromatography (n-hexane:ethyl acetate=2:1→methylene chloride:methanol=9:1). The compound (135 mg) of the present invention having the following physical data was obtained by washing the obtained solid by methyl tert-butyl ether.

Property: amorphous;
TLC:Rf 0.50 (dichloromethane:methanol:water=80:20:1);
$^{1}$H-NMR: (DMSO-$d_6$) δ 2.84, 3.17, 3.37, 4.28, 4.57, 6.59, 6.76, 7.09, 7.21, 7.40, 7.58, 7.80, 10.12.

Example 28 ethyl(acetyloxy)(4-chloro-3-nitrophenyl)acetate

To a solution (6 mL) of the compound (1.46 g) prepared in Example 22 in pyridine, acetic anhydride (2 mL) was added, and the mixture was stirred for 1 hour at room temperature. The title compound (135 mg) having the following physical data was obtained by concentrating the reaction mixture and azeotroping in toluene.

TLC:Rf 0.56 (n-hexane:ethyl acetate=2:1).

Example 29 ethyl(acetyloxy)(3-amino-4-chlorophenyl)acetate

The compound (1.94 mg) prepared in Example 28 was dissolved to a mixed solvent of acetate (10 mL) and water (1 mL). Iron filings (1.57 mg) was added to the reaction mixture at 80° C., which was stirred for 30 minutes at the same temperature. The reaction mixture was soaked in ice and was extracted with a mixed solvent (1:1) of n-hexane and ethyl acetate. The organic layer was washed with water and saturated brine solution and was dried by anhydrous magnesium sulphate. The title compound (1.53 g) having the following physical data was obtained by removing the solvent.

TLC:Rf 0.47 (n-hexane:ethyl acetate=4:1).

Example 30 ethyl(acetyloxy)(4-chloro-3-((2-chloro-4-(((2S)-4-methyl-3,4-dihydro-2H-1,4-benzoxazin-2-yl)methoxy)benzoyl)amino)phenyl)acetate Under argon atmosphere, to a mixture of the compound (196 mg) prepared in Example 29, pyridine (0.5 mL), and dichloromethane (1 mL), a solution (4 mL) of the compound (303 mg) prepared in Example 17 in dichloromethane was dropped at ice-cold temperature, and the mixture was stirred overnight at room temperature. 1N hydrochloric acid was added to the reaction mixture, which was extracted with ethyl acetate. The organic layer was washed with water and saturated brine solution and was dried by anhydrous magnesium sulphate. The title compound (207 mg) having the following physical data was obtained by purifying the residue obtained by removing the solvent by silica gel column chromatography (n-hexane:ethyl acetate=4:1→2:1).

TLC:Rf 0.39 (n-hexane:ethyl acetate=2:1).

Example 31 ethyl(4-chloro-3-((2-chloro-4-(((2S)-4-methyl-3,4-dihydro-2H-1,4-benzoxazin-2-yl)methoxy)benzoyl)amino)phenyl)(hydroxy)acetate To a solution in which the compound (207 mg) prepared in Example 30 was dissolved to a mixed solvent of ethanol and tetrahydrofuran (6 mL and 2:1), potassium carbonate (138 mg) was added, and the mixture was stirred for 2 hours at 50° C. Water was added to the cooled reaction mixture, which was extracted with ethyl acetate. The organic layer was washed with water and saturated brine solution and was dried by anhydrous magnesium sulphate. The title compound (169 mg) having the following physical data was obtained by removing the solvent.

TLC:Rf 0.38 (n-hexane:ethyl acetate=1:1).

Example 32 ethyl(4-chloro-3-((2-chloro-4-(((2S)-4-methyl-3,4-dihydro-2H-1,4-benzoxazin-2-yl)methoxy)benzoyl)amino)phenyl)(oxo)acetate Under argon atmosphere, to a mixture of the compound (159 mg) prepared in Example 31, diisopropylethylamine (0.30 mL), dimethylsulfoxide (2 mL), and ethyl acetate (4 mL), sulfur trioxide pyridine complex (139 mg) were added at ice-cold temperature, and the mixture was stirred for 1 hour at the same temperature. Water was added to the reaction mixture, which was extracted with ethyl acetate. The organic layer was washed with water and saturated brine solution and was dried by anhydrous magnesium sulphate. The title compound (104 mg) having the following physical data was obtained by purifying the residue obtained by removing the solvent by silica gel column chromatography (n-hexane:ethyl acetate=3:1→2:1).

Example 33 ethyl(4-chloro-3-((2-chloro-4-(((2S)-4-methyl-3,4-dihydro-2H-1,4-benzoxazin-2-yl)methoxy)benzoyl)amino)phenyl)(oxo)acetic acid

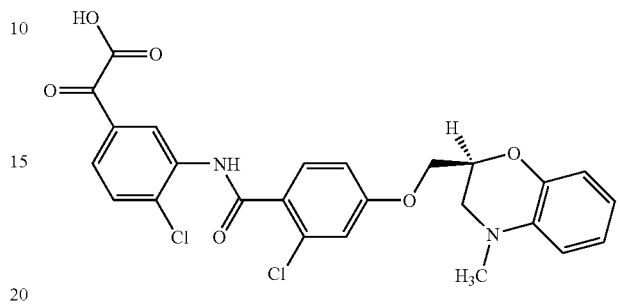

To a mixture of the compound (104 mg) prepared in Example 32, ethanol (2 mL), and tetrahydrofuran (2 mL), 1N sodium hydroxide solution (0.5 mL) was added and the mixture was stirred for 2 hours at room temperature. After being neutralized by adding 1N hydrochloric acid, the reaction mixture was extracted with ethyl acetate. The organic layer was washed with water and saturated brine solution and was dried by anhydrous magnesium sulphate. The compound (37 mg) of the present invention having the following physical data was obtained by purifying the residue obtained by removing the solvent by silica gel column chromatography (n-hexane:ethyl acetate=2:1→methylene chloride:methanol=9:1).

Property: amorphous;

TLC:Rf 0.45 (dichloromethane:methanol:water=80:20:1);

$^1$H-NMR: (DMSO-$d_6$) δ 2.84, 3.17, 3.37, 4.30, 4.58, 6.60, 6.76, 7.09, 7.21, 7.67, 8.10, 10.19.

Example 34

2-(4-chloro-3-((2,6-dimethyl-4-(((2S)-4-methyl-3,4-dihydro-2H-1,4-benzoxazin-2-yl)methoxy)benzoyl)amino)phenyl)-2-methylpropanoic acid

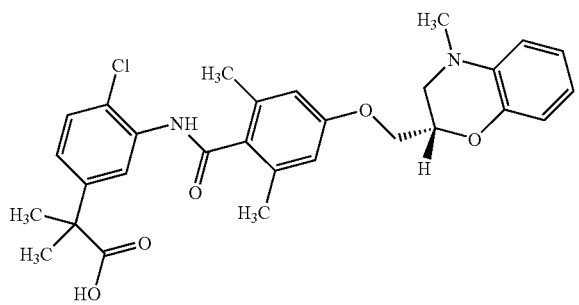

By the same procedures as a series of Example 18 and Example 19 using the compound (121 mg) prepared in Example 16 and 2,6-dimethyl-4-(((2S)-4-methyl-3,4-dihydro-2H-1,4-benzoxazin-2-yl)methoxy)benzoylchloride (211 mg) (the compound prepared by the same procedures as a series of Example 8→Example 9→Example 10 using methyl 4-hydroxy-2,6-dimethylbenzoate.), the title compound (132 mg) having the following physical data was obtained.
Property: crystal;
TLC:Rf0.17 (hexane:ethyl acetate=2:1);
$^1$H-NMR: (DMSO-d$_6$) δ 1.47, 2.32, 2.84, 3.16, 3.36, 4.18, 4.55, 6.59, 6.75, 7.24, 7.48, 7.55, 9.94.

Example 34(1)

2-(4-chloro-3-((2,5-dimethyl-4-(((2S)-4-methyl-3,4-dihydro-2H-1,4-benzoxazin-2-yl)methoxy)benzoyl)amino)phenyl)-2-methylpropanoic acid By the same procedures as a series of Example 18 and Example 19 using the compound (139 mg) prepared in Example 16 and 2,5-dimethyl-4-(((2S)-4-methyl-3,4-dihydro-2H-1,4-benzoxazin-2-yl)methoxy)benzoylchloride (211 mg) (the compound prepared by the same procedures as a series of Example 8→Example 9→Example 10 using methyl 4-hydroxy-2,5-dimethylbenzoate.), the title compound (211 mg) having the following physical data was obtained.
Property: amorphous;
TLC:Rf 0.18 (hexane:ethyl acetate=2:1);
$^1$H-NMR: (DMSO-d$_6$) δ 1.47, 2.18, 2.42, 2.84, 3.21, 3.39, 4.24, 4.60, 6.59, 6.72, 6.79, 6.91, 7.22, 7.41, 7.47, 7.57, 9.69.

Example 35

2-(3-((2,5-dimethyl-4-(((2S)-4-methyl-3,4-dihydro-2H-1,4-benzoxazin-2-yl)methoxy)benzoyl)amino)-4-methylphenyl)-2-methylpropanoic acid By the same procedures as a series of Example 18 and Example 19 using methyl 2-(3-amino-4-methylphenyl)-2-methylpropanoate (132 mg)(the compound prepared by the same procedures as Example 16) and 2,5-dimethyl-4-(((2S)-4-methyl-3,4-dihydro-2H-1,4-benzoxazin-2-yl)methoxy)benzoylchloride (210 mg)(the compound prepared by the same procedures as a series of Example 8→Example 9→Example 10 using methyl 4-hydroxy-2,5-dimethylbenzoate.), the title compound (202 mg) having the following physical data was obtained.
Property: crystal;
TLC:Rf 0.43 (chloroform:methanol:ethyl acetate=9:1:0.1);
$^1$H-NMR: (DMSO-d$_6$) δ 1.45, 2.18, 2.20, 2.40, 2.84, 3.21, 3.39, 4.23, 4.59, 6.60, 6.75, 6.91, 7.10, 7.19, 7.32, 7.37, 9.56, 12.29.

Example 36 methyl 2-(4-chloro-3-nitrophenyl)cyclopropanoate

To a solution of methyl 2-(4-chloro-3-nitrophenyl)acetate (2.0 g) and dibromoethane (3.8 mL) in N-methyl-2-pyrolidone(58 mL), sodium hydride (766 mg) was added at room temperature. Then, the mixture was stirred for 1 hour at room temperature, for 1 hour at 40° C., and then for 1 hour at 60° C. Further, sodium hydride (766 mg) was added to it, which was stirred for 20 minutes. 1N hydrochloric acid was added to the reaction solution at ice-cold temperature, which was extracted with hexane-ethyl acetate (1:1). The extract was dried by anhydrous magnesium sulphate after being washed with saturated brine solution. The title compound (762 mg) having the following physical data was obtained by filtering, concentrating, and purifying by silica gel column chromatography (n-hexane:ethyl acetate=6:1).
TLC:Rf 0.62 (n-hexane:ethyl acetate=2:1).

Example 37 methyl 2-(4-chloro-3-aminophenyl)cyclopropanoate

The title compound (769 mg) having the following physical data was obtained by the same procedures as Example 16 using the compound (899 mg) prepared in Example 36.
TLC:Rf 0.58 (n-hexane:ethyl acetate=2:1).

Example 38

1-(4-chloro-3-((2,6-dimethyl-4-(((2S)-4-methyl-3,4-dihydro-2H-1,4-benzoxazin-2-yl)methoxy)benzoyl)amino)phenyl)cyclopropanecarboxylic acid

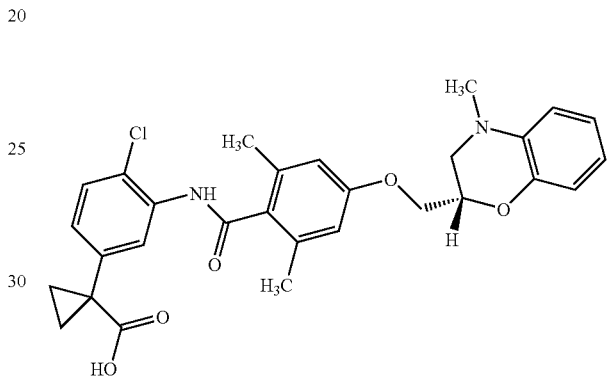

By the same procedures as a series of Example 18 and Example 19 using the compound (138 mg) prepared in Example 37 and 2,6-dimethyl-4-(((2S)-4-methyl-3,4-dihydro-2H-1,4-benzoxazin-2-yl)methoxy)benzoylchloride (211 mg) (the compound prepared by the same procedures as a series of Example 8→Example 9→Example 10 using methyl 4-hydroxy-2,6-dimethylbenzoate.), the title compound (79 mg) having the following physical data was obtained.
Property: crystal;
TLC:Rf 0.59 (chloroform:methanol=9:1);
$^1$H-NMR: (DMSO-d$_6$) δ 1.13, 1.47, 2.32, 2.84, 3.16, 3.36, 4.18, 4.56, 6.59, 6.76, 7.21, 7.43, 7.54, 9.93.

Example 38(1)

1-(4-chloro-3-((2,5-dimethyl-4-(((2S)-4-methyl-3,4-dihydro-2H-1,4-benzoxazin-2-yl)methoxy)benzoyl)amino)phenyl)cyclopropanecarboxylic acid By the same procedures as a series of reactions of Example 18 and Example 19 using the compound (138 mg) prepared in Example 37 and 2,5-dimethyl-4-(((2S)-4-methyl-3,4-dihydro-2H-1,4-benzoxazin-2-yl)methoxy)benzoylchloride (211 mg) (the compound prepared by the same procedures as a series of Example 8→Example 9→Example 10 using methyl 4-hydroxy-2,5-dimethylbenzoate.), the title compound (79 mg) having the following physical data was obtained.
Property: amorphous;
TLC:Rf 0.59 (chloroform:methanol=9:1);
$^1$H-NMR: (DMSO-d$_6$) δ 1.13, 1.46, 2.18, 2.42, 2.84, 3.21, 3.39, 4.24, 4.60, 6.59, 6.72, 6.79, 6.91, 7.20, 7.42, 7.56, 9.67.

Example 38(2)

1-(4-chloro-3-((2-ethyl-4-(((2S)-4-methyl-3,4-dihydro-2H-1,4-benzoxazin-2-yl)methoxy)benzoyl)amino)phenyl)cyclopropanecarboxylic acid By the same procedures as a series of reactions of Example 18 and Example 19 using the compound (207 mg) prepared in Example 37 and 2-ethyl-4-(((2S)-4-methyl-3,4-dihydro-2H-1,4-benzoxazin-2-yl)methoxy)benzoylchloride (211 mg) (the compound prepared by the same procedures as a series of Example 8→Example 9→Example 10 using methyl 4-hydroxy-2-ethylbenzoate.), the title compound (330 mg) having the following physical data was obtained.

Property: amorphous;
TLC:Rf 0.60 (chloroform:methanol=9:1);
$^1$H-NMR (CDCl$_3$) δ 1.27, 1.34, 1.71, 2.93, 2.93, 3.28, 3.42, 4.17, 4.29, 4.67, 6.73, 6.86, 7.10, 7.34, 7.49, 7.94, 8.56.

Example 39

Ligand Binding Using Cells Expressing the Prostanoid DP Receptor

Chinese hamster ovary (CHO) cells expressing the human DP receptor were cultivated and, according to a common method, membrane fraction was prepared. The membrane fraction (50 μL) (protein content: 42.65 μg), 100 μL of an assay buffer (25 mmol/L HEPES-NaOH containing 1 mmol/L EDTA, 5 mmol/L Mg$^{2+}$ and 10 mmol/L Mn$^{2+}$; pH7.4), 1 μL of a vehicle (dimethyl sulfoxide; DMSO) or the compound of the present invention (final concentration of DMSO: 0.5%) and 50 μL of 10 nmol/L [$^3$H]-PGD$_2$ (final concentration: 2.5 nmol/L) were added to a polyethylene tube, and an incubation mixture was incubated at the room temperature. In a non-specific binding group, 2 mmol/L PGD$_2$ was added instead of the vehicle (final concentration of PGD$_2$: 10 μmol/L). Twenty minutes later, 1 mL of ice-cold wash buffer (10 mmol/L Tris-HCl buffer containing 0.01% bovine serum albumin (BSA) and 100 mmol/L NaCl; pH7.4) was added to the tube to terminate the reaction. Immediately, the membrane fraction was collected on a glass fiber filter (GF/B) by filtration under reduced pressure. The membrane fraction on the glass fiber filter was washed once with approximately 2 mL of wash buffer and the glass fiber filter was dried. The dried glass fiber filter was place in a glass vial, a liquid scintillation cocktail was added thereto and radioactivity was measured by a liquid scintillation counter.

A specific binding of [$^3$H]-PGD$_2$ to the DP receptor was calculated by subtracting the radioactivity in the non-specific binding group from those in the groups other than the non-specific binding group. An inhibition by the compound of the present invention was calculated base on the specific binding of [$^3$H]-PGD$_2$ in the vehicle and the present invention groups. The Ki value (dissociation constant of the compound of the present invention) was calculated according to the following formula using the estimated IC$_{50}$ value (concentration of the compound of the present invention required to inhibit the specific binding in the vehicle group by 50%).

Ki=IC50/(1+([L]*/Kd))
[L]*: Concentration of [$^3$H]-PGD$_2$ (2.5 nmol/L)
Kd: Dissociation constant of [$^3$H]-PGD$_2$ The Kd value of [$^3$H]-PGD$_2$ was estimated from a non-linear regression analysis after calculating the specific bindings of [$^3$H]-PGD$_2$ upon addition of various concentrations of [$^3$H]-PGD$_2$ in accordance with the above-mentioned method.

From the results of the above measurement, it was found that the compounds of the present invention strongly bound to the DP receptor at the Ki values of not more than 10 μmol/L.

Example 40

Measurement of Antagonistic Activity Against the DP Receptor Using Cells Expressing the Prostanoid DP Receptor CHO cells stably expressing the human DP receptor was constructed; seeded on a 24-well culture plate at a cell density of 1×10$^5$ cells/well and incubated at 37° C. for 2 days in 5% CO$_2$. Each well was washed with 500 μL of MEM (minimum essential medium) and the cells were incubated at 37° C. for 10 minutes after adding 500 μL of MEM containing 2 μmol/L of diclofenac. After removal of the supernatant by aspiration, 450 μL of an MEM containing 1 mmol/L 3-isobutyl-1-methylxanthine, 2 μmol/L diclofenac and 1% BSA (assay medium) was added, followed by incubation at 37° C. for 10 minutes. Reaction was initiated by addition of 50 μL of an assay medium containing PGD$_2$ and vehicle or an assay medium containing PGD$_2$ and the compound of the present invention (final concentration of PGD$_2$: 10 nmol/L), followed by incubation at 37° C. Ten minutes later, 500 μL of ice-cold trichloroacetic acid (TCA, 10% w/v) was added to terminate the reaction. After freezing (−80° C.) and thawing the reaction mixture once, the cells were detached therefrom using a cell scraper followed by centrifugation at 13,000 rpm for 3 minutes. The resultant supernatant was collected and cAMP concentration in the supernatant was determined by a radioimmunoassay using a cAMP assay kit (manufactured by Amersham). Thus, a buffer from the [$^{125}$I]cAMP assay kit was added to a 125 μL aliquot of the above-prepared supernatant to be the volume of 500 μL and the resultant solution was mixed with 1 mL of 0.5 mol/L tri-n-octylamine in chloroform. After extraction of TCA into a chloroform layer, the amount of cAMP in an aqueous layer was quantified according to the procedure mentioned in the [$^{125}$I]cAMP assay kit.

Potency of the antagonistic activity of the compound of the present invention for the DP receptor was expressed was calculated as IC$_{50}$ value (a concentration of the compound of the present invention which is necessary to suppress the cAMP production in the absence of the compound of the present invention by 50%) from inhibitory percentage to the cAMP production at 10 nmol/L, wherein PGD$_2$ elicited a submaximum cAMP production.

From the above-mentioned measuring results, it was found that the compounds of the present invention strongly antagonized the DP receptor at the IC$_{50}$ values of not more than 10 μmol/L.

Formulation Example 1

The following components were admixed in conventional method and were punched out to obtain 10,000 tablets each containing 10 mg of active ingredient.

| | |
|---|---|
| (3-((2,3-dimethyl-4-(((2S)-4-methyl-3,4-dihydro-2H-1,4-benzoxazin-2-yl)methoxy)benzoyl)amino)-4-fluorophenyl)acetic acid | 100 g |
| Carboxymethyl Cellulose calcium(Disintegrator) | 20 g |
| Magnesium stearate(Lubricant) | 10 g |
| Microcrystalline cellulose | 870 g |

Formulation Example 2

The following components were admixed in a conventional method, in which the mixture was filtered with dust removal filter and was placed at 5 ml into ampoules. The ampoules were heat-sterilized by autoclave to thereby obtain 10,000 ampoules each containing 20 mg of the active ingredient.

| | |
|---|---:|
| (3-((2,3-dimethyl-4-(((2S)-4-methyl-3,4-dihydro-2H-1,4-benzoxazin-2-yl)methoxy)benzoyl)amino)-4-fluorophenyl)acetic acid | 200 g |
| Mannitol | 20 g |
| Distilled water | 50 L |

INDUSTRIAL APPLICABILITY

Since the compounds of the present invention represented by formula (I) bind and antagonize to DP receptors, it is considered that the compounds are useful for prevention and/or treatment of diseases mediated by DP receptors such as allergic disease (e.g., allergic rhinitis, allergic conjunctivitis, atopic dermatitis, bronchial asthma, food allergy, etc.), systemic mastocytosis, disorders accompanied by systemic mast cell activation, anaphylaxis shock, bronchoconstriction, urticaria, eczema, pimples, allergic bronchial pulmonary aspergillosis, sinusitis, migraine, nasal polypus, anaphylactic vasculitis, eosinophilic syndrome, contact dermatitis, diseases accompanied by itch (such as atopic dermatitis, urticaria, allergic conjunctivitis, allergic rhinitis and contact dermatitis), diseases (e.g., cataract, retinal detachment, inflammation, infection, sleeping disorders, etc.) which are generated secondarily as a result of behavior accompanied by itch (scratching, beating, etc.), inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis and irritable bowel syndrome. Further the compounds are considered to relate to sleeping and platelet aggregation and to be useful for these diseases.

The invention claimed is:

1. A method for treatment of allergic diseases, which comprises administering to a mammal an effective amount of the compound represented by formula (I)

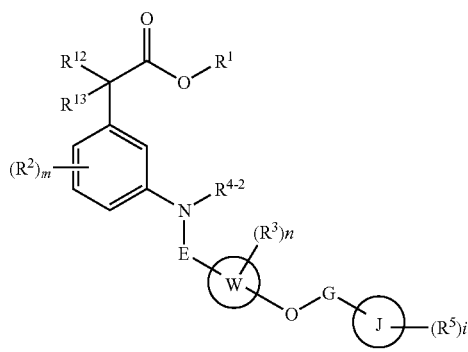

(I)

wherein $R^1$ represents (1) a hydrogen atom, (2) C1-4 alkyl, (3) C2-4 alkenyl, or (4) benzyl;

E represents —CO— or —SO$_2$—;

$R^2$ represents (1) a halogen atom, (2) C1-6 alkyl, (3) C1-6 alkoxy, (4) hydroxyl, (5) trihalomethyl, (6) cyano, (7) phenyl, (8) pyridyl, (9) nitro, (10) —NR$^6$R$^7$, or (11) C1-4 alkyl substituted with —OR$^8$, (12) oxidized C1-6 alkyl, (13) —SO$_2$R$^{11}$, (14) —SOR$^{11}$, or (15) —SR$^{11}$, or two $R^2$'s substituting for the adjacent carbon atom are taken together to represent (1) C2-5 alkylene which may be substituted by a substituent wherein one carbon atom thereof may be replaced with an oxygen atom, a nitrogen atom, or a sulfur atom which may be oxidized, or (2) C2-5 alkenylene which may be substituted by a substituent, wherein one carbon atom thereof may be replaced with an oxygen atom, a nitrogen atom, or a sulfur atom;

$R^3$ represents (1) a halogen atom, (2) C1-6 alkyl, (3) C1-6 alkoxy, (4) hydroxyl, (5) trihalomethyl, (6) cyano, (7) phenyl, (8) pyridyl, (9) nitro, (10) —NR$^6$R$^7$ or (11) C1-4 alkyl substituted with —OR$^8$, (12) oxidized C1-6 alkyl, (13) —SO$_2$R$^{11}$, (14) —SOR$^{11}$, or (15) —SR$^{11}$;

$R^6$ and $R^7$ each independently represent a hydrogen atom or C1-4 alkyl;

$R^8$ represents C1-4 alkyl, phenyl, or pyridyl;

$R^4$ represents (1) a hydrogen atom, (2) C1-6 alkyl, (3) benzyl, or (4) oxidized C1-6 alkyl;

$R^5$ represents (1) C1-6 alkyl, (2) C1-10 alkoxy, (3) C1-6 alkyl substituted with C1-6 alkoxy, (4) a halogen atom, (5) hydroxyl, (6) trihalomethyl, (7) nitro, (8) —NR$^9$R$^{10}$, (9) phenyl, (10) phenoxy, (11) oxo, (12) C2-6 acyl, (13) cyano or (14) —SO$_2$R$^{11}$, (15) —SOR$^{11}$, (16) —SR$^{11}$, (12) oxidized C1-6 alkyl;

$R^9$ and $R^{10}$ each independently represent a hydrogen atom or C1-4 alkyl; and $R^{11}$ represents C1-6 alkyl or phenyl which may be substituted;

wherein $R^6$'s to $R^{11}$'s in $R^2$'s to $R^5$'s may be the same or each independently different;

represents a C5-12 monocyclic or bicyclic carbocyclic ring or a 5- to 12-membered monocyclic or bicyclic heterocycle;

G represents (1) C1-6 alkylene having 0 to 2 hetero atoms selected from a nitrogen atom, an oxygen atom, and a sulfur atom, (2) C2-6 alkenylene having 0 to 2 hetero atoms selected from a nitrogen atom, an oxygen atom, and a sulfur atom, or (3) C2-6 alkynylene having 0 to 2 hetero atoms selected from a nitrogen atom, an oxygen atom, and a sulfur atom;

represents a C5-12 monocyclic or bicyclic carbocyclic ring or a 5- to 12-membered monocyclic or bicyclic heterocycle;

m represents 0 or an integer of 1 to 4, n represents 0 or an integer of 1 to 4, and represents 0 or an integer of 1 to 11, wherein $R^2$'s may be the same or different when m is 2 or more, $R^3$'s may be the same or different when n is 2 or more, and $R^5$'s may be the same or different when i is 2 or more; and $R^{12}$ and $R^{13}$ each independently represent (1) C1-4 alkyl which may be oxidized, (2) a halogen atom, (3) trihalomethyl, (4) hydroxyl which may be protected, (5) amino which may be protected, (6) phenyl which may be substituted, (7) pyridyl which may be substituted, or (8) a hydrogen atom, or $R^{12}$ and $R^{13}$ are taken together to represent (1) oxo, (2) C2-5 alkylene which may be substituted by a substituent, wherein one carbon atom thereof may be replaced with an oxygen atom, a nitrogen atom, or a sulfur atom, or (3) C1-6 alkylidene which may be substituted, and wherein when $R^{12}$ and $R^{13}$ each simultaneously represent a hydrogen atom, the carboxylic acid compound represented by formula (I) represents a compound selected from the group consisting of the following compounds (1)-(32);

(1) (3-((2,3-dimethyl-4-(((2S)-4-methyl-3,4-dihydro-2H-1,4-benzoxazin-2-yl)methoxy)benzoyl)amino)-4-fluorophenyl)acetic acid,
(2) (4-chloro-3-((2,3-dimethyl-4-(((2S)-4-methyl-3,4-dihydro-2H-1,4-benzoxazin-2-yl)methoxy)benzoyl)amino)phenyl)acetic acid,
(3) (4-chloro-3-((2,6-dimethyl-4-(((2S)-4-methyl-3,4-dihydro-2H-1,4-benzoxazin-2-yl)methoxy)benzoyl)amino)phenyl)acetic acid,
(4) (4-chloro-3-((5-chloro-2-fluoro-4-(((2S)-4-methyl-3,4-dihydro-2H-1,4-benzoxazin-2-yl)methoxy)benzoyl)amino)phenyl)acetic acid,
(5) (4-chloro-3-((2,5-dimethyl-4-(((2S)-4-methyl-3,4-dihydro-2H-1,4-benzoxazin-2-yl)methoxy)benzoyl)amino)phenyl)acetic acid,
(6) (4-chloro-3-((2-fluoro-5-methyl-4-(((2S)-4-methyl-3,4-dihydro-2H-1,4-benzoxazin-2-yl)methoxy)benzoyl)amino)phenyl)acetic acid,
(7) (4-chloro-3-((2,5-difluoro-4-(((2S)-4-methyl-3,4-dihydro-2H-1,4-benzoxazin-2-yl)methoxy)benzoyl)amino)phenyl)acetic acid,
(8) (3-((2,3-dimethyl-4-(((2S)-4-methyl-3,4-dihydro-2H-1,4-benzoxazin-2-yl)methoxy)benzoyl)amino)-4-methylphenyl)acetic acid,
(9) (3-((2,3-dimethyl-4-(((2S)-4-methyl-3,4-dihydro-2H-1,4-benzoxazin-2-yl)methoxy)benzoyl)amino)-5-methylphenyl)acetic acid,
(10) (3-((2,3-dimethyl-4-(((2S)-4-methyl-3,4-dihydro-2H-1,4-benzoxazin-2-yl)methoxy)benzoyl)amino)phenyl)acetic acid,
(11) (3-((2,6-dimethyl-4-(((2S)-4-methyl-3,4-dihydro-2H-1,4-benzoxazin-2-yl)methoxy)benzoyl)amino)phenyl)acetic acid,
(12) (3-((2,6-dimethyl-4-(((2S)-4-methyl-3,4-dihydro-2H-1,4-benzoxazin-2-yl)methoxy)benzoyl)amino)-5-methylphenyl)acetic acid,
(13) (5-((2,6-dimethyl-4-(((2S)-4-methyl-3,4-dihydro-2H-1,4-benzoxazin-2-yl)methoxy)benzoyl)amino)-2-fluorophenyl)acetic acid,
(14) (5-((2,5-dimethyl-4-(((2S)-4-methyl-3,4-dihydro-2H-1,4-benzoxazin-2-yl)methoxy)benzoyl)amino)-2-methylphenyl)acetic acid,
(15) (5-((2,5-dimethyl-4-(((2S)-4-methyl-3,4-dihydro-2H-1,4-benzoxazin-2-yl)methoxy)benzoyl)amino)-2-fluorophenyl)acetic acid,
(16) (3-((2,5-dimethyl-4-(((2S)-4-methyl-3,4-dihydro-2H-1,4-benzoxazin-2-yl)methoxy)benzoyl)amino)phenyl)acetic acid,
(17) (5-((2,3-dimethyl-4-(((2S)-4-methyl-3,4-dihydro-2H-1,4-benzoxazin-2-yl)methoxy)benzoyl)amino)-2-fluorophenyl)acetic acid,
(18) (5-((2,3-dimethyl-4-(((2S)-4-methyl-3,4-dihydro-2H-1,4-benzoxazin-2-yl)methoxy)benzoyl)amino)-2-methylphenyl)acetic acid,
(19) (5-((2,6-dimethyl-4-(((2S)-4-methyl-3,4-dihydro-2H-1,4-benzoxazin-2-yl)methoxy)benzoyl)amino)-2-methylphenyl)acetic acid,
(20) (3-((2,6-dimethyl-4-(((2S)-4-methyl-3,4-dihydro-2H-1,4-benzoxazin-2-yl)methoxy)benzoyl)amino)-4-methylphenyl)acetic acid,
(21) (3-((2,6-dimethyl-4-(((2S)-4-methyl-3,4-dihydro-2H-1,4-benzoxazin-2-yl)methoxy)benzoyl)amino)-4-fluorophenyl)acetic acid,
(22) (3-((2,5-dimethyl-4-(((2S)-4-methyl-3,4-dihydro-2H-1,4-benzoxazin-2-yl)methoxy)benzoyl)amino)-4-fluorophenyl)acetic acid,
(23) (3-((2,5-dimethyl-4-(((2S)-4-methyl-3,4-dihydro-2H-1,4-benzoxazin-2-yl)methoxy)benzoyl)amino)-4-methylphenyl)acetic acid,
(24) (3-((2,5-dimethyl-4-(((2S)-4-methyl-3,4-dihydro-2H-1,4-benzoxazin-2-yl)methoxy)benzoyl)amino)-5-methylphenyl)acetic acid,
(25) (4-chloro-3-((4-((2R)-2,3-dihydro-1,4-benzodioxin-2-ylmethoxy)-2,6-dimethylbenzoyl)amino)phenyl)acetic acid,
(26) (2-chloro-5-((2,3-dimethyl-4-(((2S)-4-methyl-3,4-dihydro-2H-1,4-benzoxazin-2-yl)methoxy)benzoyl)amino)phenyl)acetic acid,
(27) (2-chloro-5-((2,6-dimethyl-4-(((2S)-4-methyl-3,4-dihydro-2H-1,4-benzoxazin-2-yl)methoxy)benzoyl)amino)phenyl)acetic acid,
(28) (2-chloro-5-((2,5-dimethyl-4-(((2S)-4-methyl-3,4-dihydro-2H-1,4-benzoxazin-2-yl)methoxy)benzoyl)amino)phenyl)acetic acid,
(29) (4-chloro-3-((4-((3R)-2,3-dihydro-1-benzofuran-3-ylmethoxy)-2,6-dimethylbenzoyl)amino)phenyl)acetic acid,
(30) (4-chloro-3-((2,6-dimethyl-4-(((3R)-5-methyl-2,3-dihydro-1-benzofuran-3-yl)methoxy)benzoyl)amino)phenyl)acetic acid,
(31) (4-chloro-3-((4-((2S)-2,3-dihydro-1-benzofuran-2-ylmethoxy)-2,6-dimethylbenzoyl)amino)phenyl)acetic acid, and
(32) (3-((4-(1,3-benzodioxol-2-ylmethoxy)-2,6-dimethylbenzoylamino)-4-chlorophenyl)acetic acid, a salt thereof, a solvate thereof, wherein the allergic disease is allergic rhinitis, allergic conjunctivitis, or bronchial asthma.

2. A method according to claim 1, wherein the compound represented by formula (I) is selected from the group consisting of the following compounds;

(1) 2-(4-chloro-3-((2-chloro-4-(((2S)-4-methyl-3,4-dihydro-2H-1,4-benzoxazin-2-yl)methoxy)benzoyl)amino)phenyl)-2-methylpropanoic acid,
(2) (4-chloro-3-((2-chloro-4-(((2S)-4-methyl-3,4-dihydro-2H-1,4-benzoxazin-2-yl)methoxy)benzoyl)amino)phenyl)(difluoro)acetic acid, and
(3) (4-chloro-3-((2-chloro-4-(((2S)-4-methyl-3,4-dihydro-2H-1,4-benzoxazin-2-yl)methoxy)benzoyl)amino)phenyl)(oxo)acetic acid.

* * * * *